US012533128B1

(12) United States Patent
Bakos et al.

(10) Patent No.: US 12,533,128 B1
(45) Date of Patent: Jan. 27, 2026

(54) METHOD FOR PRE-BENDING STAPLE TIPS USING AN ARBOR PLATE

(71) Applicant: Cilag GmbH International, Zug (CH)

(72) Inventors: Gregory J. Bakos, Mason, OH (US); Brian D. Schings, Maineville, OH (US); Nicholas Fanelli, Morrow, OH (US); Jason Rector, Maineville, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/781,545

(22) Filed: Jul. 23, 2024

(51) Int. Cl.

| | |
|---|---|
| ***A61B 17/072*** | (2006.01) |
| ***A61B 17/064*** | (2006.01) |
| ***A61B 17/115*** | (2006.01) |

(52) U.S. Cl.
CPC ...... *A61B 17/07207* (2013.01); *A61B 17/064* (2013.01); *A61B 17/1155* (2013.01); *A61B 2017/0645* (2013.01); *A61B 2017/07271* (2013.01)

(58) Field of Classification Search
CPC .......... A61B 17/07207; A61B 17/0643; A61B 34/30
See application file for complete search history.

(56) References Cited

U.S. PATENT DOCUMENTS 5,205,459 A 4/1993 Brinkerhoff
5,242,457 A * 9/1993 Akopov .............. A61B 17/1114 606/220
5,292,053 A 3/1994 Bilotti
5,333,773 A 8/1994 Main
5,350,104 A 9/1994 Main
5,533,661 A 7/1996 Main
8,210,411 B2 7/2012 Yates et al.
8,910,847 B2 12/2014 Nalagatla
9,186,142 B2 11/2015 Fanelli et al.
9,517,065 B2 12/2016 Simms et al.
9,622,746 B2 4/2017 Simms et al.
9,713,469 B2 7/2017 Leimbach
9,717,497 B2 8/2017 Zerkle et al.
9,795,379 B2 10/2017 Leimbach et al.
9,808,248 B2 11/2017 Hoffman
9,839,421 B2 12/2017 Zerkle et al.
9,907,552 B2 3/2018 Measamer
9,936,949 B2 4/2018 Measamer
(Continued)

OTHER PUBLICATIONS

U.S. Appl. No. 63/459,739, filed May 19, 2023.
(Continued)

*Primary Examiner* — Nathaniel C Chukwurah
(74) *Attorney, Agent, or Firm* — Lempia Summerfield Katz LLC

(57) ABSTRACT

A method of forming staples between opposing jaws of a stapling device, the method including positioning a set of guide surfaces over each of a plurality of staples loaded in openings of a staple cartridge of a first jaw of the opposing jaws of the stapling device, where each staple includes a crown with staple legs extending therefrom, and where ends of the staple legs opposite the crown exit through the openings. The method further including bending the ends of the staple legs with the guide surfaces, where the guide surfaces are further configured to cause the staple legs to continue bending as the staples exit the openings.

20 Claims, 66 Drawing Sheets

(56) References Cited

U.S. PATENT DOCUMENTS

| | | | |
|---|---|---|---|
| 10,092,292 | B2 | 10/2018 | Boudreaux et al. |
| 10,182,813 | B2 | 1/2019 | Leimbach et al. |
| 10,363,031 | B2 | 7/2019 | Alexander, III et al. |
| 10,709,452 | B2 | 7/2020 | Dinardo |
| 10,966,722 | B2 | 4/2021 | Shelton, IV |
| 11,304,697 | B2 | 4/2022 | Fanelli et al. |
| 11,317,912 | B2 | 5/2022 | Jenkins et al. |
| 11,406,379 | B2 | 8/2022 | Hess |
| 11,439,391 | B2 | 9/2022 | Bruns et al. |
| 12,004,744 | B2 | 6/2024 | Schings |
| 2011/0087276 | A1* | 4/2011 | Bedi ................ A61B 17/07207 227/175.1 |
| 2011/0226837 | A1* | 9/2011 | Baxter, III ........... A61B 17/064 227/175.1 |
| 2015/0083772 | A1 | 3/2015 | Miller |
| 2018/0132849 | A1 | 5/2018 | Miller |
| 2023/0301674 | A1 | 9/2023 | Rector |

OTHER PUBLICATIONS

U.S. Appl. No. 63/467,469, filed May 19, 2023.
U.S. Appl. No. 63/467,615, filed May 19, 2023.
U.S. Appl. No. 63/467,622, filed May 19, 2023.
U.S. Appl. No. 63/467,623, filed May 19, 2023.
U.S. Appl. No. 63/467,648, filed May 19, 2023.
U.S. Appl. No. 63/467,656, filed May 19, 2023.

* cited by examiner

METHOD FOR PRE-BENDING STAPLE TIPS USING AN ARBOR PLATE

BACKGROUND

Open surgery (e.g., traditional surgery, conventional surgery, open or non-endoscopic procedures, and the like) involves creating a single large incision in the body to access the affected area. During open surgery, a surgeon may work directly with their hands and may have a broader view of the surgical site. In some instances, such as in the case of transplants, large incisions are necessary to remove the damaged organ and replace it with a healthy one. This type of surgery is also used in a variety of treatments, such as the removal of kidney stones.

Surgical staplers are frequently used in surgical procedures for suturing body tissues such as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forcibly against the anvil.

More particularly, surgical staplers, also referred to as endocutters or stapler cutters, typically include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of wedges which, when driven distally, pass through openings in the staple cartridge and engage drivers supporting the staples to affect the firing of the staples toward the anvil.

One such frequently used type of surgical stapler is the open linear stapler, which is a device that enables the surgeon to simultaneously place one or more rows of surgical staples in body tissue or organs. By way of example, a typical procedure is a pneumonectomy, which is a removal of a portion of the patient's lungs. The linear stapler can be used several times during this procedure, including for the occlusion of the pulmonary artery prior to its resection. For this later use, the surgeon first clamps the jaws of the stapler across the artery, then forms the staple and before reopening the stapler jaws, cuts the artery with a scalpel using the edge of the staple jaws as a guide.

In some settings, endoscopic or laparoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path.

It may be desirable to sever and staple tissue of various thicknesses. A thin layer of tissue may result in staples that only form loosely, perhaps requiring the need for bolstering material. A thick layer of tissue may result in formed staples that exert a strong compressive force on the captured tissue, perhaps resulting in necrosis, bleeding or poor staple formation/retention. Rather than limiting the range of tissue thicknesses that are appropriate for a given surgical stapling and severing instrument, it would be desirable to accommodate a wider range of tissue thickness with the same surgical stapling and severing instrument.

In certain types of surgical procedures the use of surgical staples has become the preferred method of joining tissue, and, specially configured surgical staplers have been developed for these applications. For example, intra-luminal or circular staplers have been developed for use in a surgical procedure known as an anastomosis. Circular staplers useful to perform an anastomosis are disclosed, for example, in U.S. Pat. Nos. 5,205,459 and 10,709,452 which are each herein incorporated by reference.

An anastomosis is a surgical procedure wherein sections of intestine are joined together after a connecting section has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches.

The development of circular staplers has greatly simplified the anastomosis procedure and also decreased the time required to perform an anastomosis.

In general, a conventional circular stapler typically consists of an elongated shaft having a proximal actuating mechanism and a distal stapling mechanism mounted to the shaft. The distal stapling mechanism typically consists of a fixed stapling cartridge containing a plurality of staples configured in a concentric circular array. A round cutting knife is concentrically mounted in the cartridge interior to the staples. The knife is movable in an axial, distal direction. Extending axially from the center of the cartridge is a trocar shaft. The trocar shaft is movable, axially, with respect to the cartridge and elongated shaft. An anvil member is mounted to the trocar shaft. The anvil member has a conventional staple anvil mounted to it for forming the ends of the staples. The distance between the distal face of the staple cartridge and the staple anvil is controlled by an adjustment mechanism mounted to the proximal end of the stapler shaft. Tissue contained between the staple cartridge and the staple anvil is simultaneously stapled and cut when the actuating mechanism is engaged by the surgeon.

When performing an anastomosis using a circular stapler, typically, the intestine is stapled using a conventional surgical stapler with double rows of staples being emplaced on either side of a target section (i.e., specimen) of intestine. The target section is typically simultaneously cut as the section is stapled. Next, after removing the specimen, the surgeon typically inserts the anvil into the proximal end of the lumen, proximal of the staple line. This is done by inserting the anvil head into an entry port cut into the proximal lumen by the surgeon.

On occasion, the anvil can be placed transanally, by placing the anvil head on the distal end of the stapler and inserting the instrument through the rectum. Typically the distal end of the stapler is inserted transanally. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby engaging the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, a concentric circular blade is driven through the intestinal tissue ends, cutting the ends adjacent to the inner row of staples. The surgeon then withdraws the stapler from the intestine and the anastomosis is complete.

Staple forming requires high loads to initiate buckling of the staple legs, particularly when the staple legs buckle multiple times, and a very high load is typically generated when firing in a traditional way against staple forming pockets of an anvil. These high loads may result in poorly formed staples and high firing loads. Curling staple legs using staple forming anvil pockets also requires precise anvil pocket alignment in order to properly form the staples. Further, staple formation using staple forming pockets on the anvil may be negatively impacted by tissue conditions or misalignment between staples and pockets, which also may lead to poorly formed staples.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
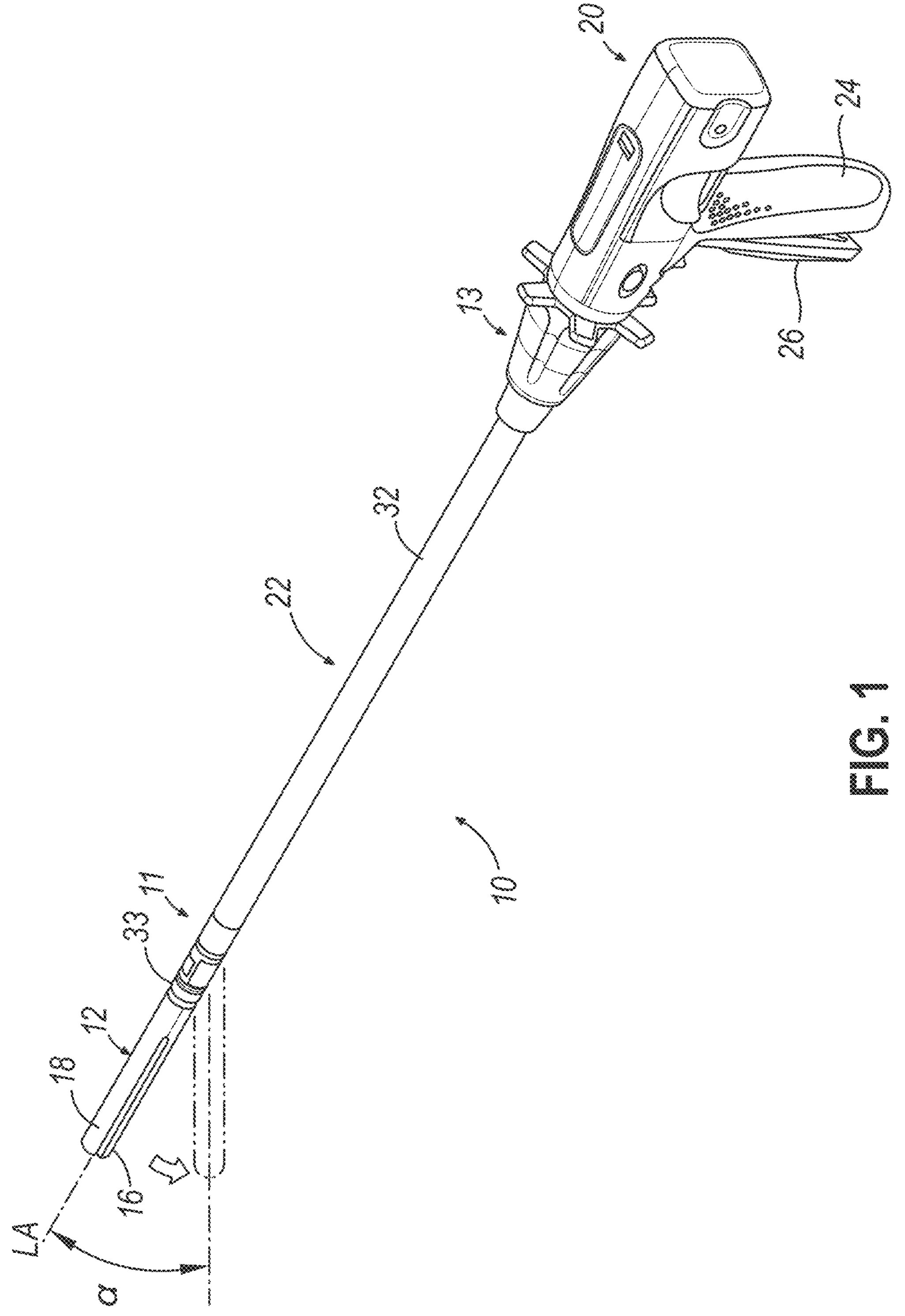
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

Applicant of the present application also owns the following U.S. Patent Applications that were filed on Jul. 23, 2024 and which are each herein incorporated by reference in their respective entireties:

- U.S. patent application Ser. No. 18/781,551, entitled "Staple Cartridge Containing Forming Surfaces That Bend Staple Legs Upon Exiting";

- U.S. patent application Ser. No. 18/781,555, entitled "Stapler Device That Forms Staples From Various Cartridges Having Different Row Patterns";
- U.S. patent application Ser. No. 18/781,558, entitled "Staple Shape Control Using Selective Bending Segments Of Staples";
- U.S. patent application Ser. No. 18/781,566, entitled "Staple Cartridge With Static Angled Arbors To Form Three-Dimensional (3D) Staples";
- U.S. patent application Ser. No. 18/781,573, entitled "Staple Cartridge With Dynamic Arbors That Produce Non-Constant Curl Radius";
- U.S. patent application Ser. No. 18/781,578, entitled "Deployable Arbor Sets That Break Away From Staple Cartridge"; and
- U.S. patent application Ser. No. 18/781,583, entitled "Multi-Part Staple With Separate Legs And Crown To Facilitate Staple Release From Arbors."

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

Spatial and functional relationships between elements are described using various terms, including "connected," "engaged," "interfaced," "on," and "coupled." Unless explicitly described as being "direct," when a relationship between first and second elements is described in the present disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, on, or coupled to another element, there are no intervening elements present. Other words used to describe the relationship between elements should be interpreted in a like fashion (e.g., "between," versus "directly between," "adjacent," versus "directly adjacent," and the like.).

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. ILLUSTRATIVE SURGICAL STAPLERS

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (a). End effector 12 of the present example includes a lower jaw 16 (also referred to herein as a cartridge jaw) that includes a staple cartridge 37, and an upper jaw in the form of a pivotable anvil jaw 18.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongated slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
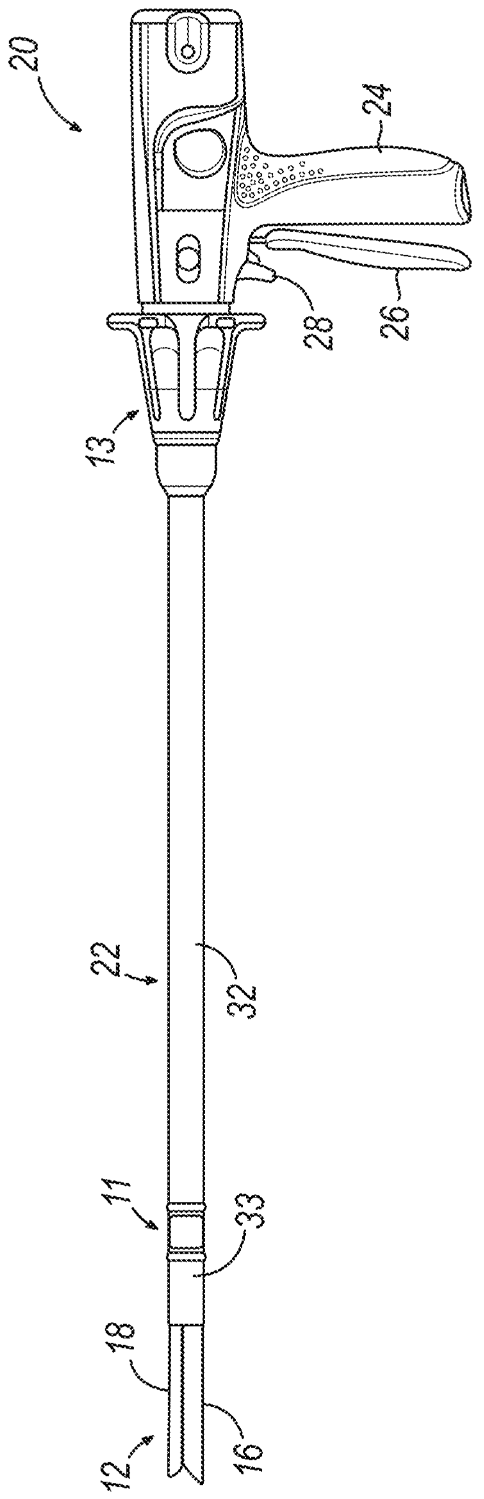
FIG. 2 depicts a side view of the instrument of FIG. 1.

As shown in FIG. 2, handle portion 20 also includes a firing trigger 28. An elongate member (not shown) longitudinally extends through shaft 22 and communicates a longitudinal firing motion from handle portion 20 to a firing beam 14 in response to actuation of firing trigger 28. This distal translation of firing beam 14 causes the stapling and severing of clamped tissue in end effector 12, as will be described in greater detail below.

FIGS. 3-6 depict end effector 12 employing an E-beam form of firing beam 14 to perform a number of functions. It should be understood that an E-beam form is just a merely illustrative example. Firing beam 14 may take any other suitable form, including but not limited to non-E-beam forms. As shown in FIGS. 3-6, end effector 12 employs a firing beam 14 that includes a transversely oriented upper pin 38, a firing beam cap 44, a transversely oriented middle pin 46, and a distally presented cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44. Thereby, firing beam 14 affirmatively spaces end effector 12 during firing.

Some non-E-beam forms of firing beam 14 may lack upper pin 38, middle pin 46 and/or firing beam cap 44. Some such versions of instrument 10 may simply rely on closure ring 33 or some other feature to pivot anvil 18 to a closed position and hold anvil 18 in the closed position while firing beam 14 advances to the distal position. Other suitable forms that firing beam 14 may take should be apparent to those of ordinary skill in the art in view of the teachings herein.

Figure 3:
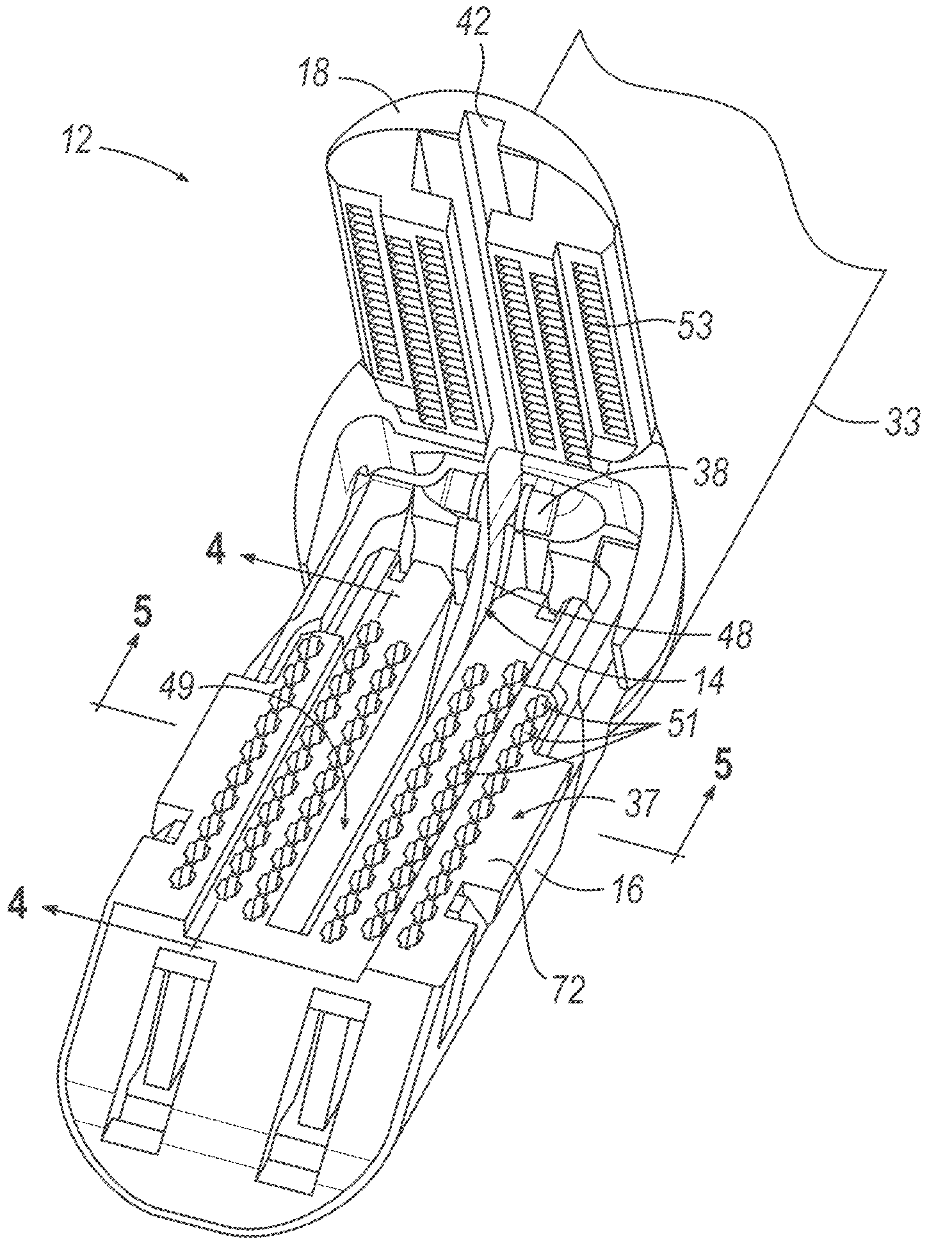
FIG. 3 depicts a perspective view of an opened end effector of the instrument of FIG. 1.
Figure 4A:
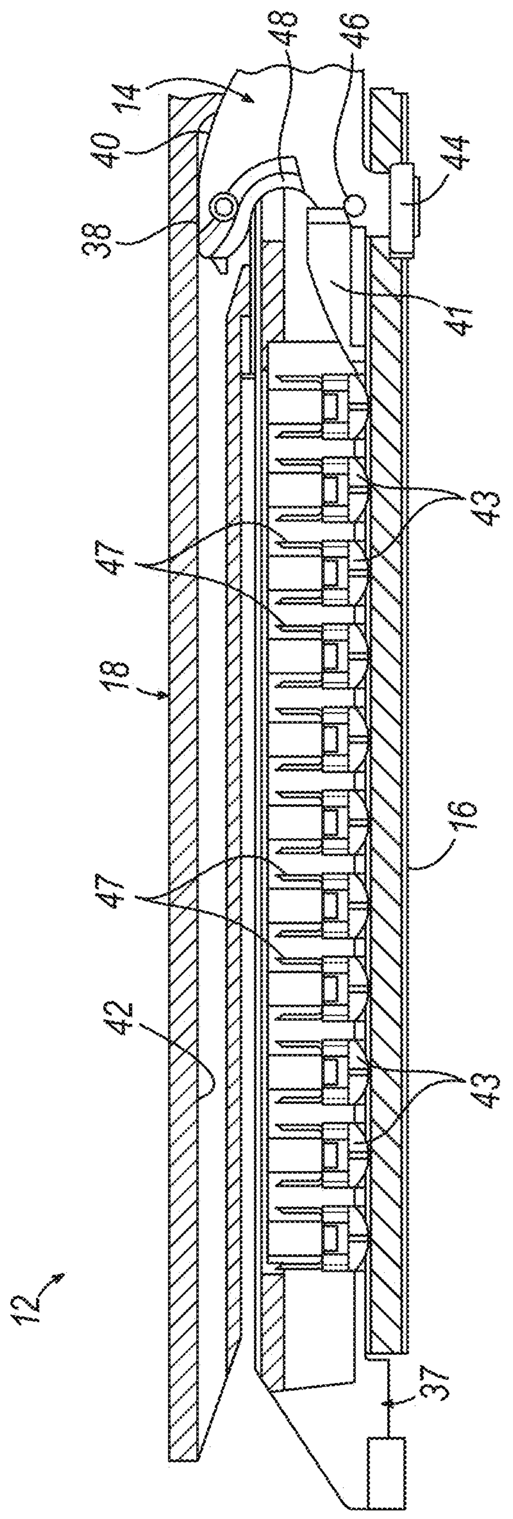
FIG. 4A depicts a side cross-sectional view of the end effector of FIG. 3, taken along line 4-4 of FIG. 3, with the firing beam in a proximal position.
Figure 4B:
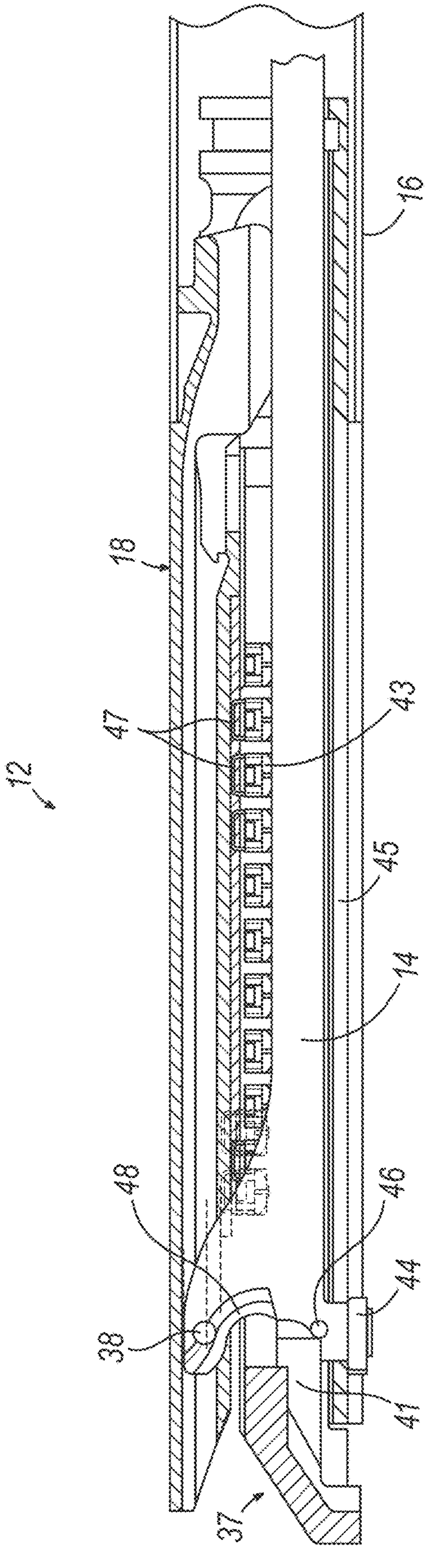
FIG. 4B depicts a side cross-sectional view of the end effector of FIG. 3, taken along line 4-4 of FIG. 3, with the firing beam in a distal position.
Figure 5:
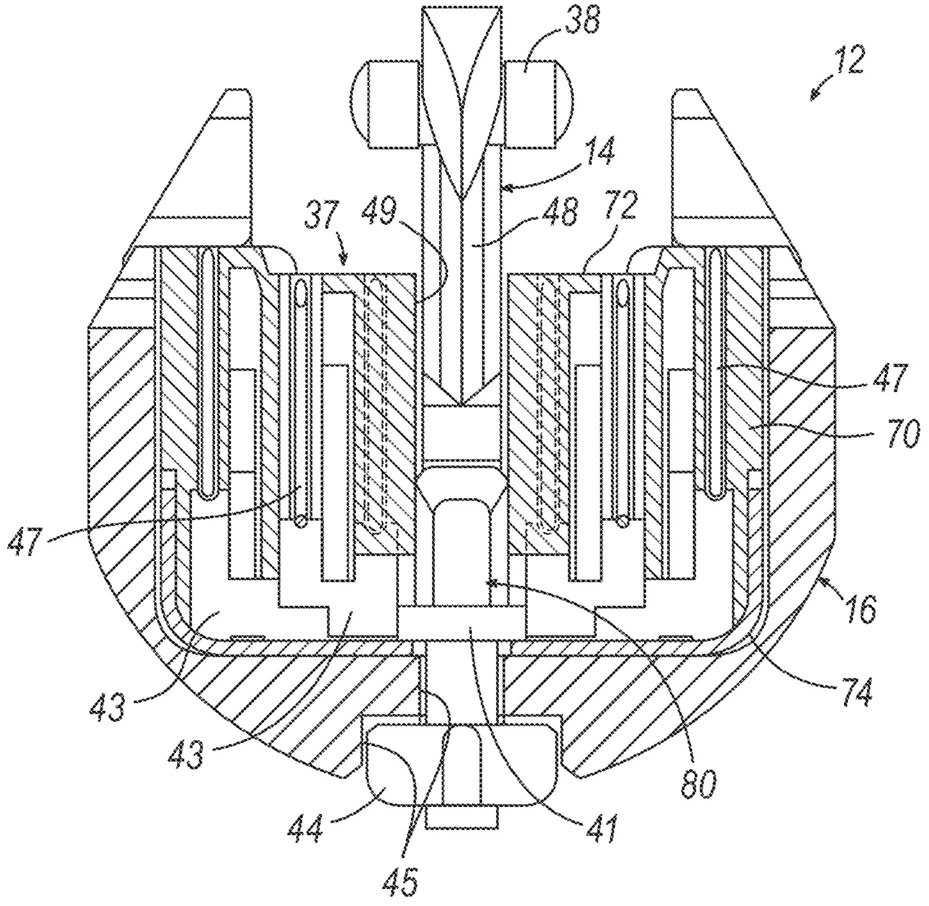
FIG. 5 depicts an end cross-sectional view of the end effector of FIG. 3, taken along line 5-5 of FIG. 3.
Figure 6:
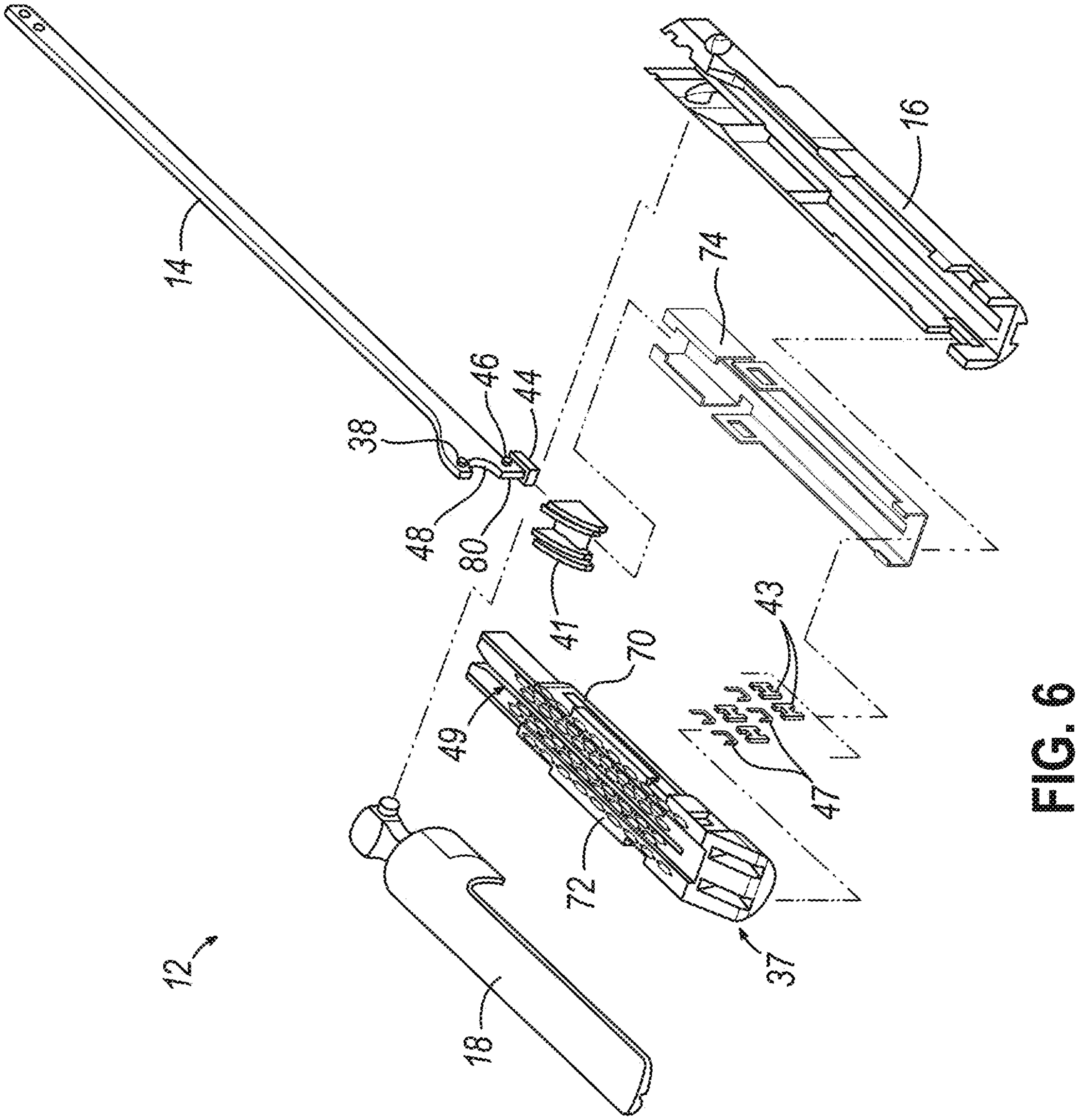
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
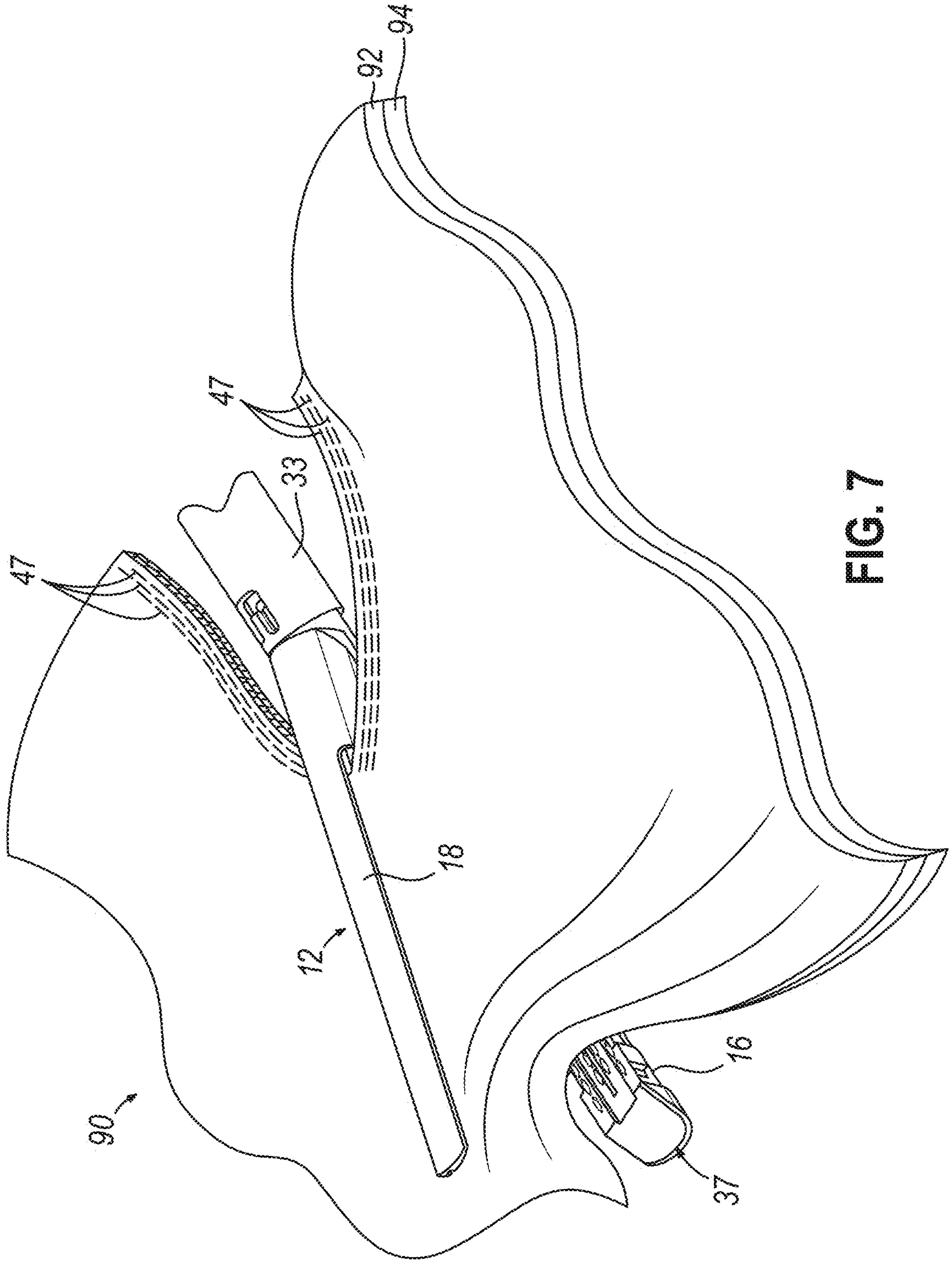
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

It should be understood that cutting edge 48 may sever tissue substantially contemporaneously with staples 47 being driven through tissue during each actuation stroke. In the present example, cutting edge 48 just slightly lags behind driving of staples 47, such that a staple 47 is driven through the tissue just before cutting edge 48 passes through the same region of tissue, though it should be understood that this order may be reversed or that cutting edge 48 may be directly synchronized with adjacent staples. While FIG. 7 shows end effector 12 being actuated in two layers 92, 94 of tissue 90, it should be understood that end effector 12 may be actuated through a single layer of tissue 90 or more than two layers 92, 94 of tissue. It should also be understood that the formation and positioning of staples 47 adjacent to the cut line produced by cutting edge 48 may substantially seal the tissue at the cut line, thereby reducing or preventing bleeding and/or leaking of other bodily fluids at the cut line. Furthermore, while FIG. 7 shows end effector 12 being actuated in two substantially flat, apposed planar layers 92, 94 of tissue, it should be understood that end effector 12 may also be actuated across a tubular structure such as a blood vessel, a section of the gastrointestinal tract, etc. FIG. 7 should therefore not be viewed as demonstrating any limitation on the contemplated uses for end effector 12. Various suitable settings and procedures in which instrument 10 may be used should be apparent to those of ordinary skill in the art in view of the teachings herein.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

Figure 8:
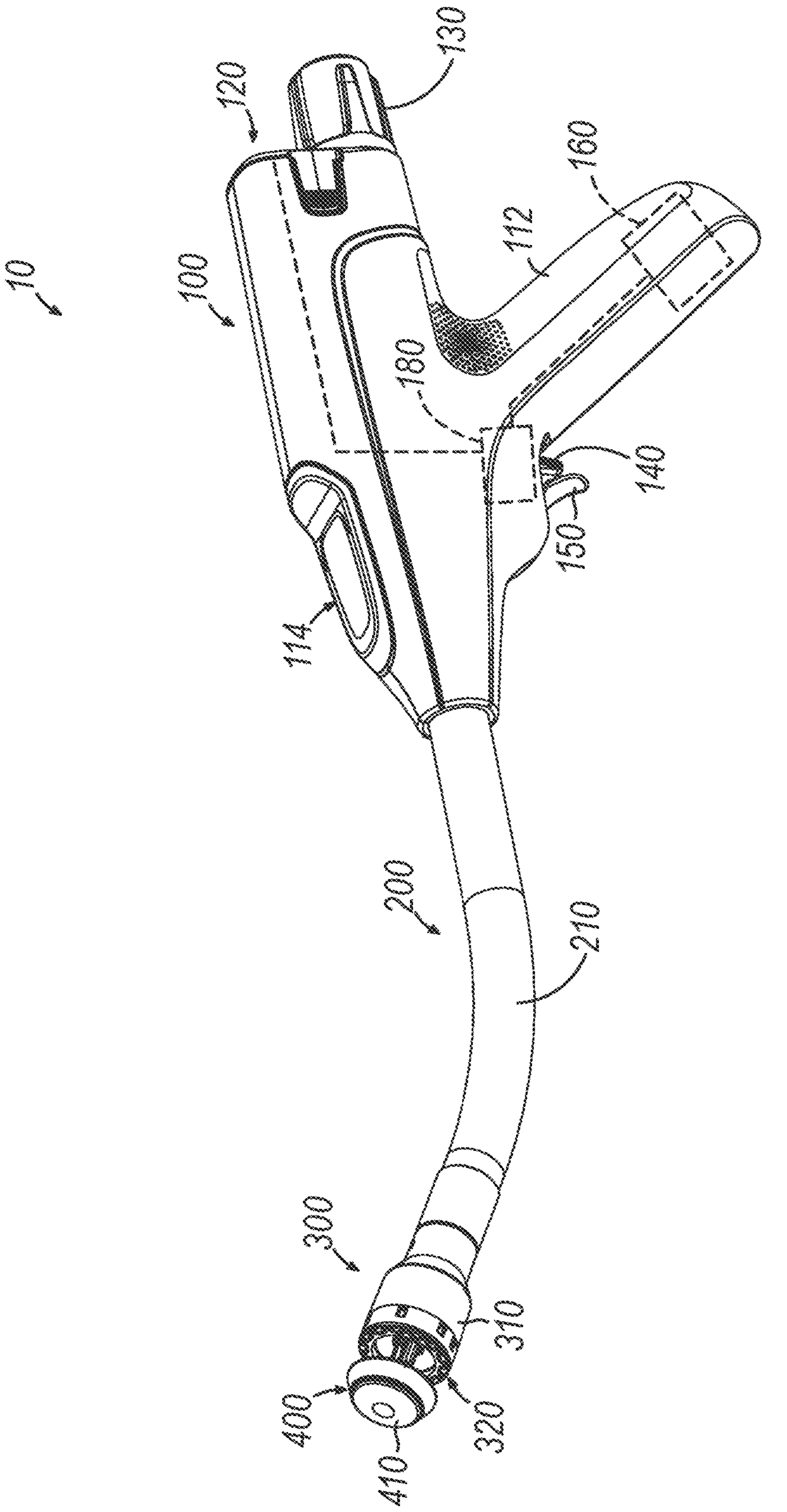
FIG. 8 depicts a perspective view of an example surgical instrument in the form of a circular surgical stapler that includes a handle assembly, a shaft assembly, and an end effector having a stapling head and an anvil.
Figure 9:
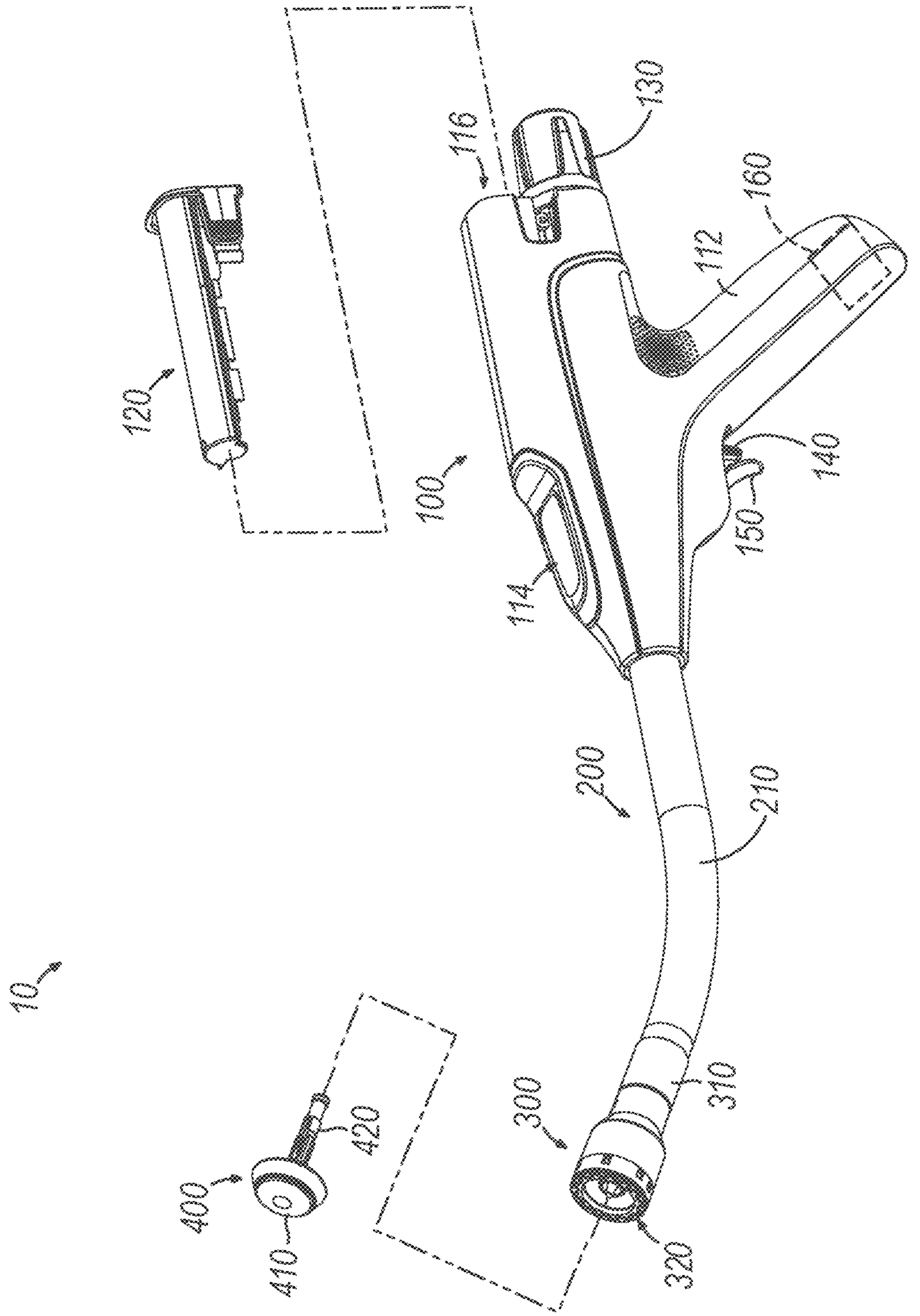
FIG. 9 depicts a perspective view of the surgical instrument of FIG. 8, with a battery pack removed from the handle portion and the anvil separated from the stapling head assembly.

FIGS. 8-9 depict an example surgical instrument 10 that may be used to provide an end-to-end, side-to-side, or end-to-side anastomosis between two sections of an anatomical lumen such as a portion of a patient's digestive tract. Surgical instrument 10 of this example is a circular surgical stapler and includes a body assembly in the form of an actuator such as a manually operated handle portion 100, a shaft 200 extending distally from handle portion 100, an end effector in the form of a stapling head 300 at a distal end of shaft 200 and an anvil 400 configured to releasably couple and cooperate with stapling head 300 to clamp, staple, and cut tissue. Instrument 10 further includes a removable battery pack 120 operable to provide electrical power to a motor 160 housed within handle 100, as described in greater detail below.

As shown in FIGS. 8-9, and as described in greater detail below, anvil 400 is configured to removably couple with shaft 200, adjacent to stapling head 300. As also described in greater detail below, anvil 400 and stapling head 300 are configured to cooperate to manipulate tissue in three ways, including clamping the tissue, cutting the tissue, and stapling the tissue. A rotatable knob 130 at the proximal end of handle 100 is rotatable to provide precise clamping of the tissue between anvil 400 and stapling head 300. When a safety trigger 140 of handle 100 is pivoted away from a firing trigger 150 of handle 100, firing trigger 150 may be actuated to thereby provide cutting and stapling of the clamped tissue.

Figure 10:
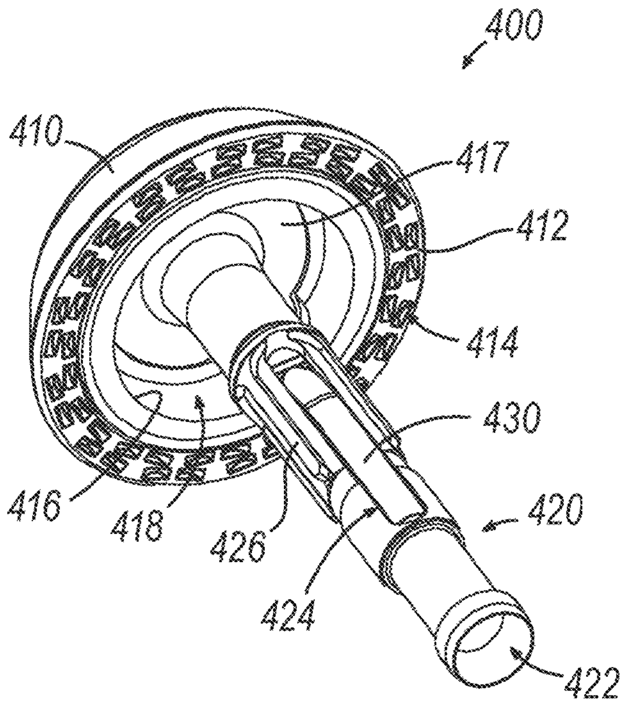
FIG. 10 depicts a perspective view of the anvil of the surgical instrument of FIG. 8.

As best seen in FIG. 10, anvil 400 of the present example comprises a head 410 and a shank 420. Head 410 includes a proximal stapling surface 412 that defines a plurality of staple forming pockets 414. Staple forming pockets 414 are arranged in two concentric annular arrays in the present example. Staple forming pockets 414 are configured to deform staples as the staples are driven into staple forming pockets 414. Proximal stapling surface 412 terminates at an inner edge 416, which defines an outer boundary of an annular recess 418 surrounding shank 420. A breakable washer 417 is positioned within annular recess 418 and is configured to provide the operator with a tactile and audible indication that a distal firing stroke has been completed, in addition to serving as a cutting board, as described in greater detail below.

Shank 420 defines a bore 422 and includes a pair of pivoting latch members 430. Latch members 430 are positioned within bore 422 such that distal ends 434 are positioned at the proximal ends of lateral openings 424, which are formed through the sidewall of shank 420. Latch members 430 thus act as retaining clips. This allows anvil 400 to be removably secured to an actuatable closure member in the form of a trocar 330 of stapling head 300, as will be described in greater detail below. Shank 420 of anvil 400 and trocar 330 of stapling head 300 thus cooperate with one another as coupling members.

Figure 11:
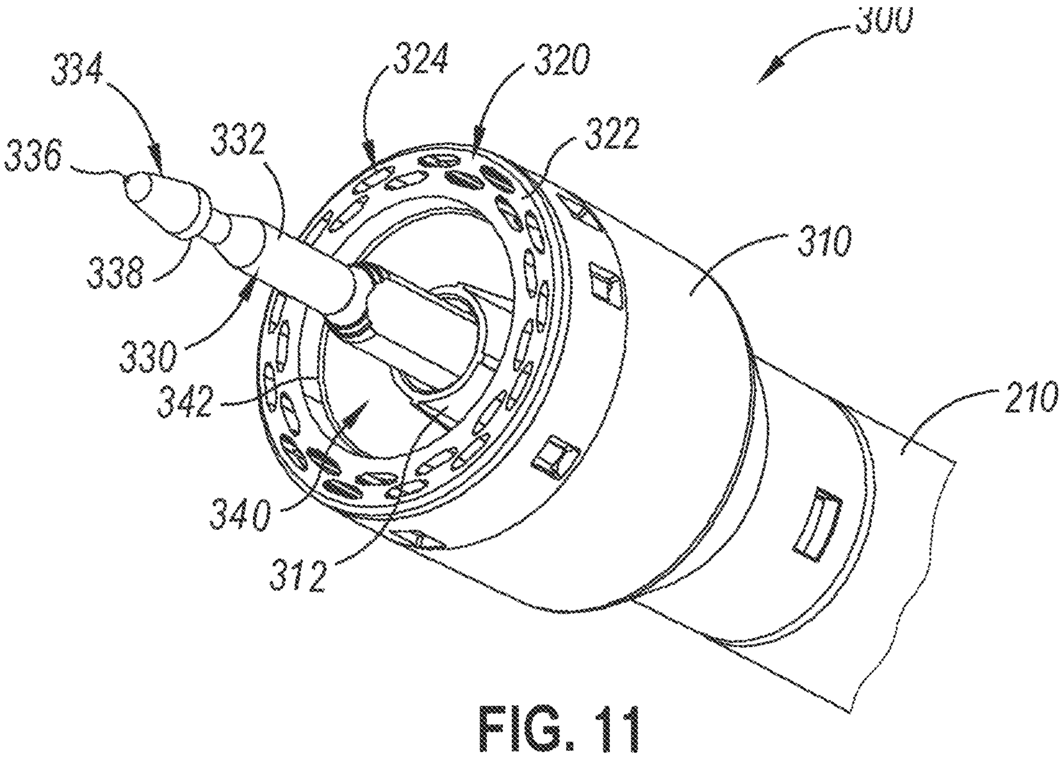
FIG. 11 depicts a perspective view of the stapling head of the surgical instrument of FIG. 8.
Figure 12:
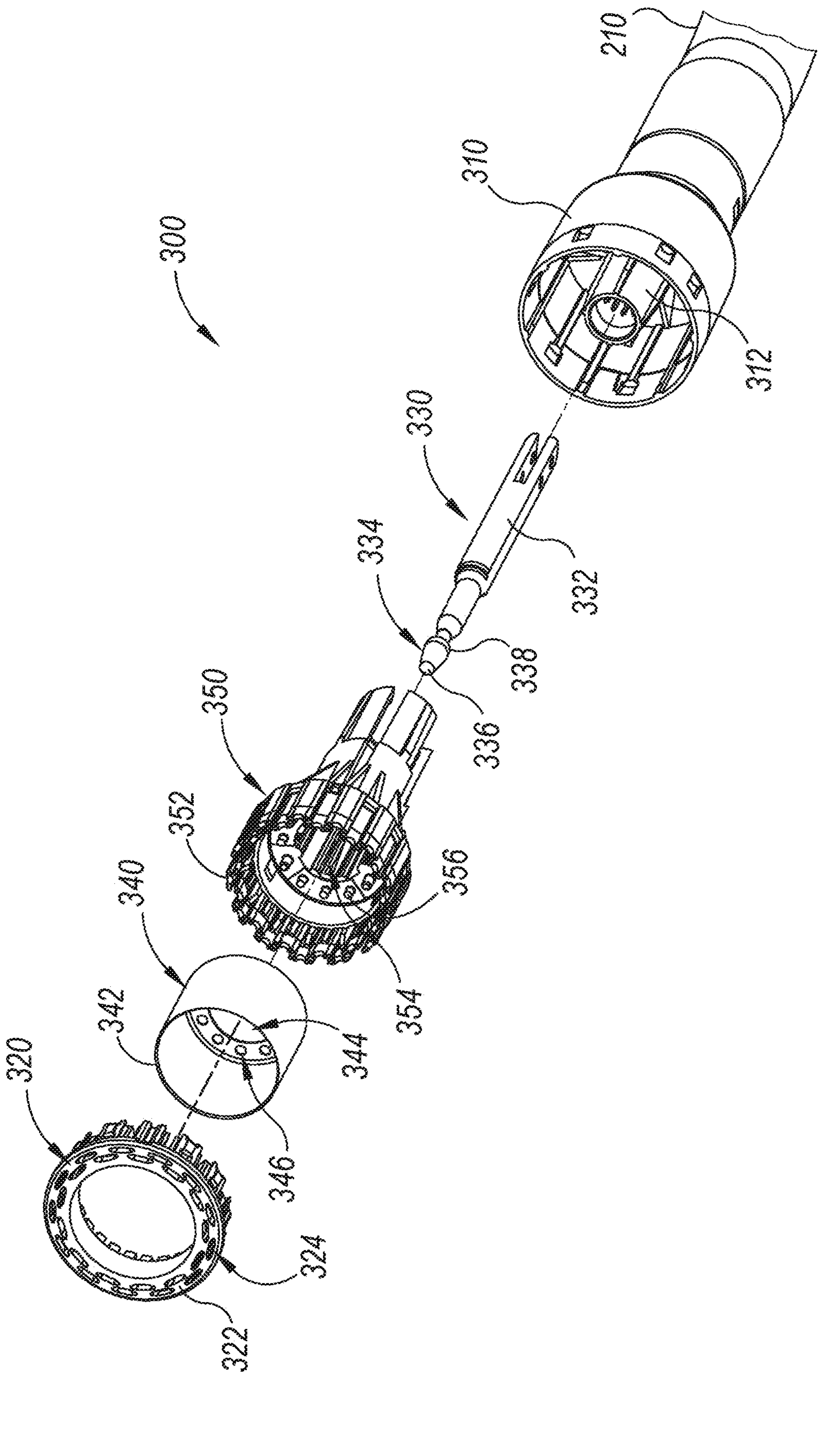
FIG. 12 depicts an exploded perspective view of the stapling head of FIG. 11.

As best seen in FIGS. 11 and 12, stapling head 300 of the present example is coupled to a distal end of shaft 200 and comprises a tubular body member 310 and a staple driver member 350 slidably housed therein. Body member 310 includes a distally extending cylindraceous inner core member 312 positioned coaxially therein. Body member 310 is fixedly secured to an outer sheath 210 of shaft 200, and body member 310 and outer sheath 210 thus serve together as a mechanical ground for stapling head 300.

Trocar 330 is positioned coaxially within inner core member 312 of body member 310. As described in greater detail below, trocar 330 is operable to translate distally and proximally relative to body member 310 in response to rotation of knob 130 relative to casing 110 of handle portion 100. Trocar 330 comprises a shaft 332 and a head 334. Head 334 includes a pointed tip 336 and a radially inwardly extending proximal surface 338. Head 334 and the distal portion of shaft 332 are configured for insertion into bore 422 of anvil 400. Proximal surface 338 and latch shelves 436 have complementary positions and configurations such that latch shelves 436 engage proximal surface 338 when shank 420 of anvil 400 is fully seated on trocar 330. Anvil 400 is thus secured to trocar 330 through a snap fit provided by latch members 430.

Staple driver member 350 is operable to actuate longitudinally within body member 310 in response to activation of motor 160 as described in greater detail below. As shown best in FIG. 12, staple driver member 350 of the present example includes two distally presented concentric annular arrays of staple drivers 352. Staple drivers 352 are arranged to correspond with the arrangement of staple forming pockets 414 of anvil 400. Thus, each staple driver 352 is configured to drive a corresponding staple distally into a corresponding staple forming pocket 414 when stapling head 300 is actuated (or "fired"). Staple driver member 350 also defines a bore 354 that is configured to coaxially and slidably receive core member 312 of body member 310. An annular array of studs 356 project distally from a distally presented surface surrounding bore 354.

A cylindraceous knife member 340 is coaxially positioned within a distally-opening central recess of staple driver member 350 that communicates with bore 354. Knife member 340 includes a distally presented, sharp circular cutting edge 342. Knife member 340 is sized such that knife member 340 defines an outer diameter that is just smaller than the diameter defined by the radially inner-most surfaces of the inner annular array of staple drivers 352. Knife member 340 also defines a central opening that is configured to coaxially receive core member 312 of body member 310. An annular array of openings 346 formed in knife member 340 is configured to mate with the annular array of studs 356 of staple driver member 350, such that knife member 340 is fixedly secured to staple driver member 350 via studs 356 and openings 346.

An annular deck member 320 is fixedly secured to a distal end of body member 310. Deck member 320 includes a distally presented stapling surface in the form of a deck surface 322 having two concentric annular arrays of staple openings 324. Staple openings 324 are arranged to align with the arrangement of staple drivers 352 of staple driver member 350 and staple forming pockets 414 of anvil 400 described above. Each staple opening 324 is configured to slidably receive and provide a pathway for a corresponding staple driver 352 to drive a corresponding staple distally through deck member 320 and into a corresponding staple forming pocket 414 when stapling head 300 is actuated. As best seen in FIG. 12, deck member 320 has a central opening that defines an inner diameter that is just slightly larger than the outer diameter defined by knife member 340. Deck member 320 is thus configured to permit knife member 340 to translate longitudinally through the central opening concurrently with longitudinal translation of staple driver member 350. In particular, knife member 340 is configured to actuate relative to deck member 340 between a proximal retracted position and a distal extended position, where cutting edge 342 is proximal to deck surface 322 in the proximal retracted position and distal to deck surface 322 in the distal extended position.

Figure 13:
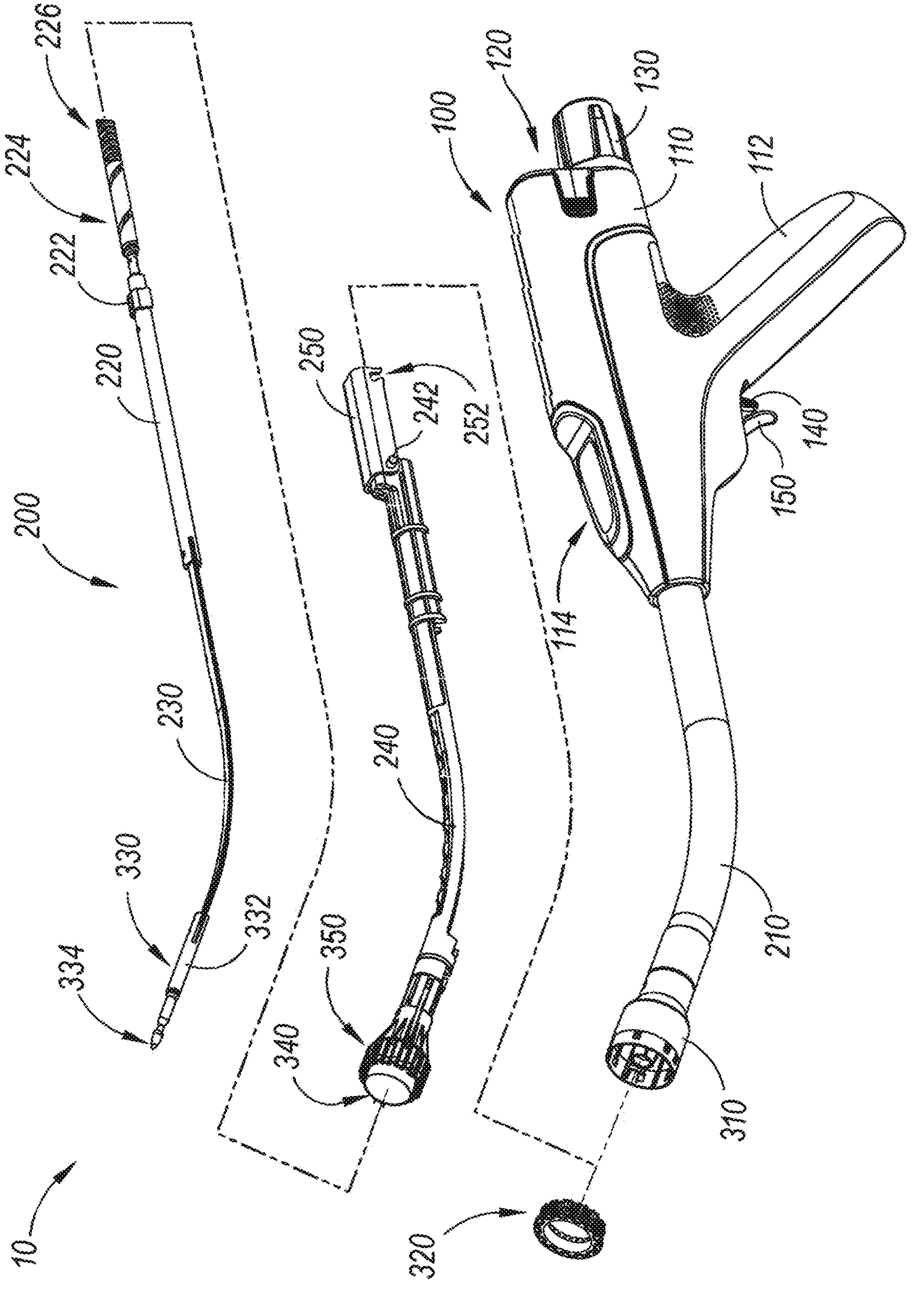
FIG. 13 depicts an exploded perspective view of the surgical instrument of FIG. 8, with portions of the shaft shown separated from each other.

FIG. 13 shows various components of shaft 200, which operatively couple components of stapling head 300 with components of handle 100. In particular, and as noted above, shaft 200 includes an outer sheath 210 that extends between handle 100 and body member 310 and includes a medial portion that extends along a curved path.

Shaft 200 further includes a trocar actuation rod 220 having a proximal end operatively coupled with rotatable knob 130 and a distal end coupled with a flexible trocar actuation band assembly 230, the assembly of which is slidably housed within outer sheath 210. The distal end of trocar actuation band assembly 230 is fixedly secured to the proximal end of trocar shaft 332, such that trocar 330 will translate longitudinally relative to outer sheath 210 in response to translation of trocar actuation band assembly 230 and trocar actuation rod 220 relative to outer sheath 210, which occurs in response to rotation of rotatable knob 130. A clip 222 is fixedly secured to trocar actuation rod 220 and is configured to cooperate with complementary features within handle portion 100 to prevent trocar actuation rod 220 from rotating within handle portion 100 while still permitting trocar actuation rod 220 to translate longitudinally within handle portion 100. Trocar actuation rod 220 further includes a section of coarse helical threading 224 and a section of fine helical threading 226 proximal to coarse helical threading 224, which are configured to control a rate of longitudinal advancement of trocar actuation rod 220, as described in greater detail below.

Shaft 200 further includes a stapling head driver 240 that is slidably housed within outer sheath 210 and about the combination of trocar actuation rod 220 and trocar actuation band assembly 230. Stapling head driver 240 includes a distal end that is fixedly secured to the proximal end of staple driver member 350, a proximal end secured to a drive bracket 250 via a pin 242, and a flexible section disposed therebetween. It should therefore be understood that staple driver member 350 will translate longitudinally relative to outer sheath 210 in response to translation of stapling head driver 240 and drive bracket 250 relative to outer sheath 210.

As shown in FIG. 8, handle portion 100 includes a casing 110 having a lower portion that defines an obliquely oriented pistol grip 112 and an upper portion that supports a user interface feature 114 and releasably receives a battery pack 120, as described in greater detail below. Handle portion 100 further includes several features that are operable to actuate anvil 400 and stapling head 300. In particular, handle portion 100 includes a rotatable knob 130, a safety trigger 140, a firing trigger 150, a motor 160, and a motor activation module 180. Knob 130 is coupled with trocar actuation rod 220 via a nut (not shown), such that coarse helical threading 224 will selectively engage a thread engagement feature within the interior of the nut; and such that fine helical threading 226 will selectively engage a thread engagement feature within the interior of knob 130. These complementary structures are configured such that trocar actuation rod 220 will first translate proximally at a relatively slow rate, and then translate proximally at a relatively fast rate, in response to rotation of knob 130.

It should be understood that when anvil 400 is coupled with trocar 330, rotation of knob 130 will provide corresponding translation of anvil 400 relative to stapling head 300. It should also be understood that knob 130 may be rotated in a first angular direction (e.g., clockwise) to retract anvil 400 proximally toward stapling head 300; and in a second angular direction (e.g., counterclockwise) to extend anvil 400 distally away from stapling head 300. Knob 130 may thus be used to adjust a gap distance (d) between opposing stapling surfaces 412, 322 of anvil 400 and stapling head 300 until a suitable gap distance has been achieved, for example as shown in FIG. 14C described below.

Firing trigger 150 is operable to activate motor 160 to thereby actuate stapling head 300 to staple and cut tissue clamped between anvil 400 and stapling head 300. Safety trigger 140 is operable to selectively block actuation of firing trigger 150 based on the longitudinal position of anvil 400 in relation to stapling head 300. Handle portion 100 also includes components that are operable to selectively lock out both triggers 140, 150 based on the position of anvil 400 relative to stapling head 300. For instance, safety trigger 140 may be blocked from rotating from an engaged position to a disengaged position until the position of anvil 400 relative to stapling head 300 is within a predefined range. Accordingly, until the anvil position is within the predefined range, actuation of firing trigger 150 is blocked by safety trigger 140, thereby inhibiting firing of stapling head 300.

Firing trigger 150 is operable to actuate a switch of motor activation module 180 (FIG. 8) when firing trigger 150 is pivoted proximally to a fired position. Motor activation module 180 is in communication with battery pack 120 and motor 160, such that motor activation module 180 is configured to provide activation of motor 160 with electrical power from battery pack 120 in response to firing trigger 150 actuating the switch of motor activation module 180. Thus, motor 160 will be activated when firing trigger 150 is pivoted. This activation of motor 160 will actuate stapling head 300 via drive bracket 250, as described in greater detail below.

FIGS. 14A-14E show instrument 10 being used to form an anastomosis 70 between two tubular anatomical structures 202, 402. By way of example only, the tubular anatomical structures 202, 402 may comprise sections of a patient's esophagus, colon, or other portions of the patient's digestive tract, or any other tubular anatomical structures.

Figure 14A:
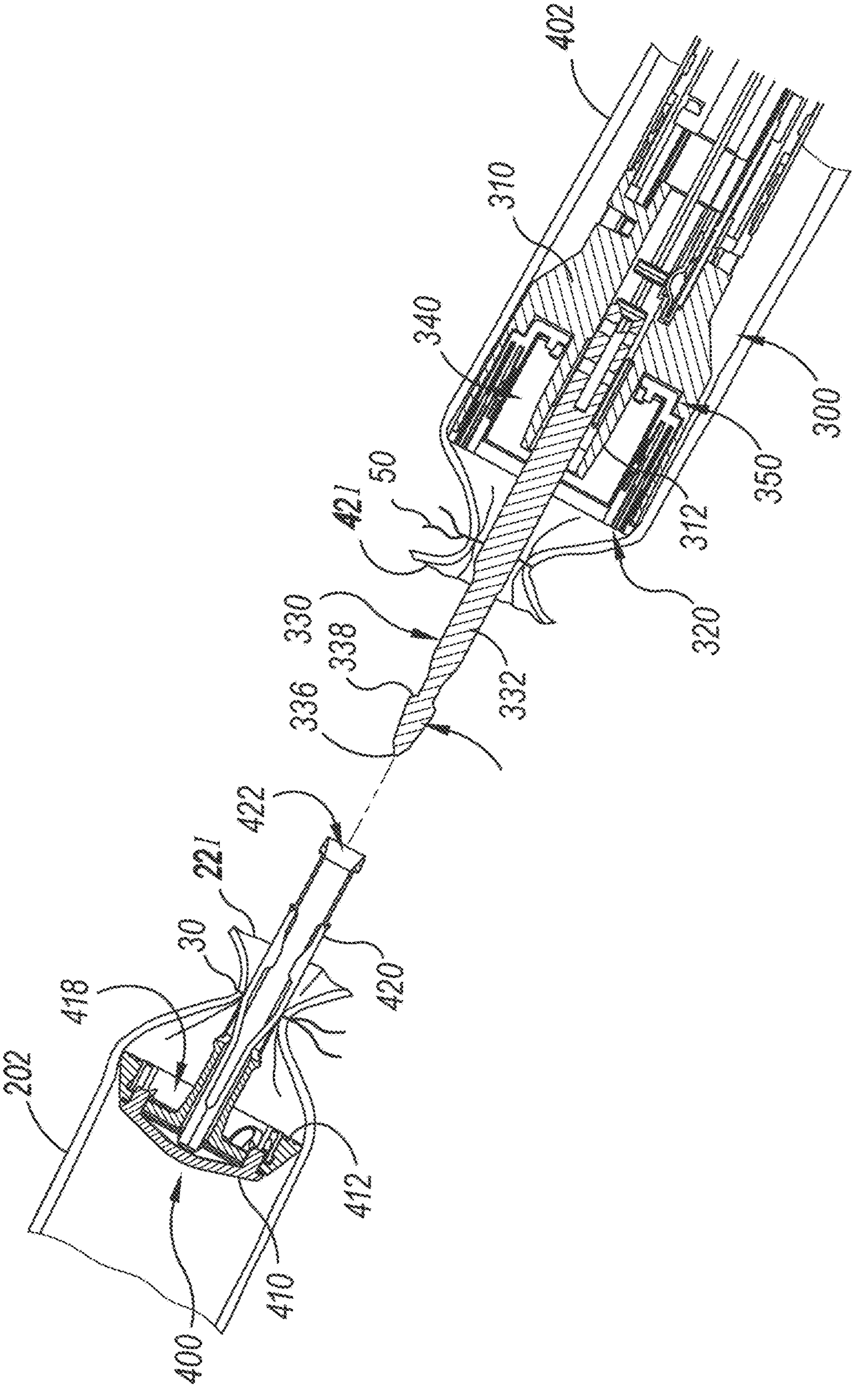
FIG. 14A depicts a cross-sectional side view of the anvil of FIG. 10 positioned within a first section of a digestive tract and the stapling head of FIG. 11 positioned within a separate second section of the digestive tract, with the anvil separated from the stapling head assembly.

As shown in FIG. 14A, anvil 400 is positioned in one tubular anatomical structure 202 and stapling head 300 is positioned in another tubular anatomical structure 402. As shown in FIG. 14A, anvil 400 is positioned in tubular anatomical structure 202 such that shank 420 protrudes from the open severed end 221 of tubular anatomical structure 202. In the present example, a purse-string suture 30 is provided about a mid-region of shank 420 to generally secure the position of anvil 400 in tubular anatomical structure 202. Stapling head 300 is positioned in tubular anatomical structure 402 such that trocar 330 protrudes from the open severed end 421 of tubular anatomical structure 402. A purse-string suture 50 is provided about a mid-region of trocar shaft 332 to generally secure the position of stapling head 300 in tubular anatomical structure 402. Stapling head 300 is then urged distally to ensure that stapling head 300 is fully seated at the distal end of tubular anatomical structure 402.

Figure 14B:
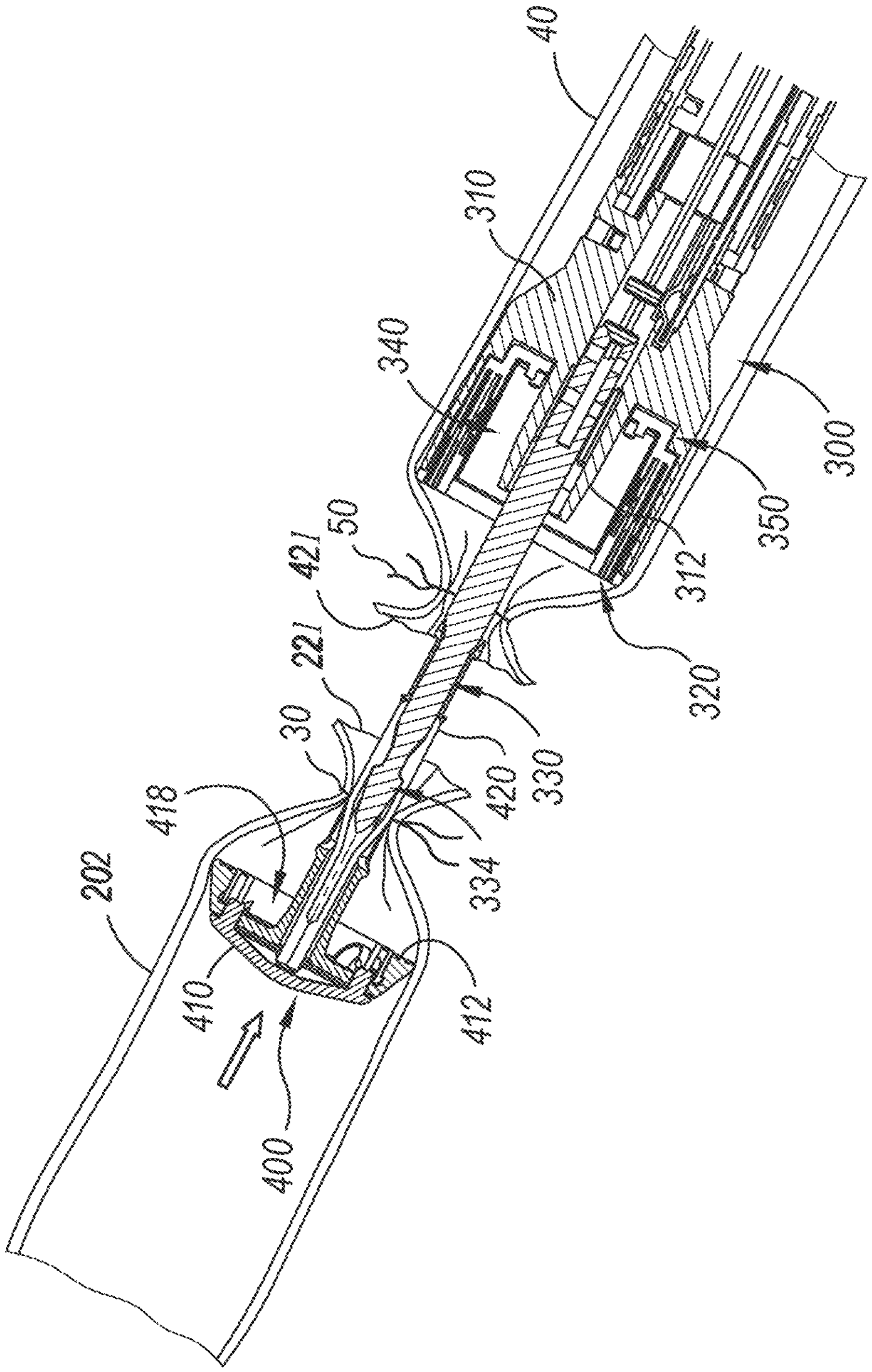
FIG. 14B depicts a cross-sectional side view of the anvil of FIG. 10 positioned within the first section of the digestive tract and the stapling head of FIG. 11 positioned within the separate second section of the digestive tract, with the anvil secured to the stapling head assembly.
Figure 14C:
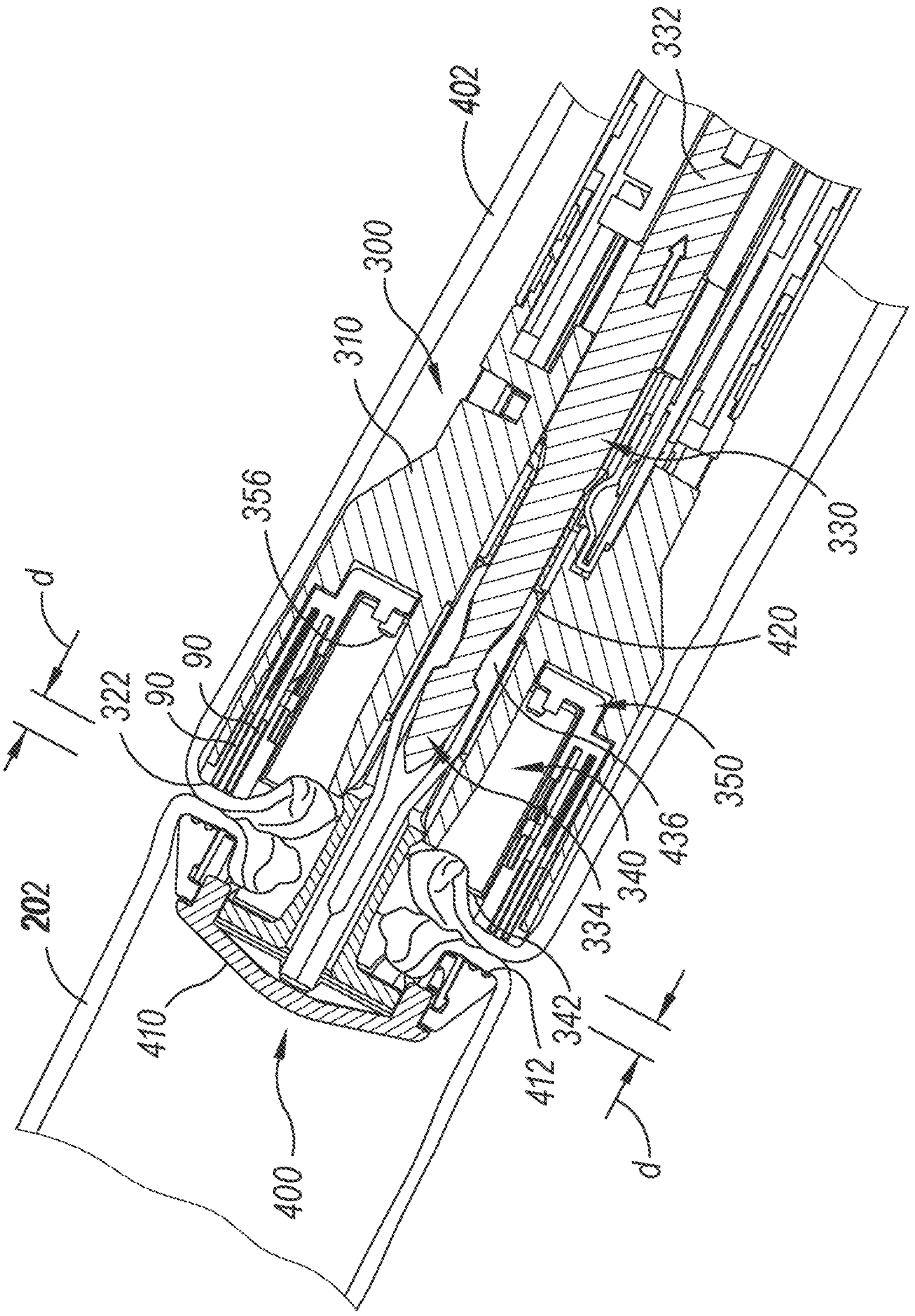
FIG. 14C depicts a cross-sectional side view of the anvil of FIG. 10 positioned within the first section of the digestive tract and the stapling head of FIG. 11 positioned within the separate second section of the digestive tract, with the anvil retracted toward the stapling head to thereby clamp tissue between the anvil and the stapling head assembly.

Next, anvil 400 is secured to trocar 330 by inserting trocar 330 into bore 422 as shown in FIG. 14B. Latch members 430 of anvil 400 engage head 334 of trocar 330, thereby providing a secure fit between anvil 400 and trocar 330. The operator then rotates knob 130 while holding casing 110 stationary via pistol grip 112. This rotation of knob 130 causes trocar 330 and anvil 400 to retract proximally. As shown in FIG. 14C, this proximal retraction of trocar 330 and anvil 400 compresses the tissue of tubular anatomical structures 202, 402 between surfaces 412, 322 of anvil 400 and stapling head 300. As this occurs, the operator may observe the tactile resistance or feedback via knob 130 while turning knob 130, with such tactile resistance or feedback indicating that the tissue is being compressed. As the tissue is being compressed, the operator may visually observe the position of an indicator needle (not shown) within user interface feature 114 of handle portion 100 to determine whether the gap distance (d) between opposing surfaces 412, 322 of anvil 400 and stapling head 300 is appropriate; and make any necessary adjustments via knob 130.

Once the operator has appropriately set the gap distance (d) via knob 130, the operator pivots safety trigger 140 toward pistol grip 112 to enable actuation of firing trigger 150. The operator then pivots firing trigger 150 toward pistol grip 112, thus causing firing trigger 150 to actuate the switch of motor activation module 180 and thereby activate motor 160 to rotate. This rotation of motor 160 causes actuation (or "firing") of stapling head 300 by actuating drive bracket 250 distally to thereby drive knife member 340 and staple driver member 350 distally together, as shown in FIG. 14D.

As knife member 340 translates distally, cutting edge 342 of knife member 340 cuts excess tissue that is positioned within annular recess 418 of anvil 400 and the interior of knife member 340. Additionally, washer 417 positioned within annular recess 418 of anvil 400 is broken by knife member 340 when the knife member 340 completes a full distal range of motion from the position shown in FIG. 14C to the position shown in FIG. 14D. It should be understood that washer 417 may also serve as a cutting board for knife member 340 to assist in cutting of tissue.

Figure 14D:
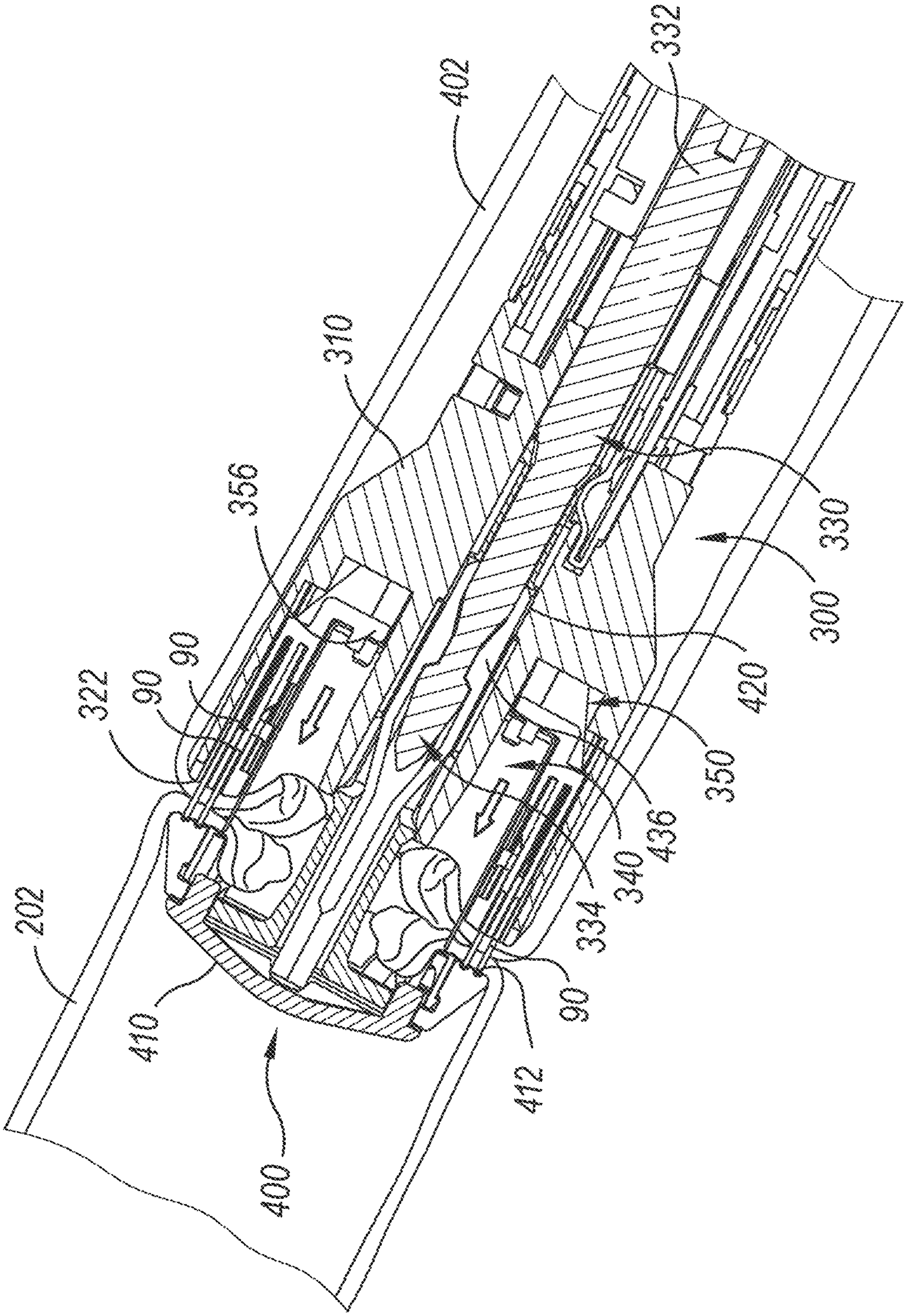
FIG. 14D depicts a cross-sectional side view of the anvil of FIG. 10 positioned within the first section of the digestive tract and the stapling head of FIG. 11 positioned within the second section of the digestive tract, with the stapling head actuated to sever and staple the clamped tissue and thereby joining the first and second sections of the digestive tract.

As staple driver member 350 translates distally from the position shown in FIG. 14C to the position shown in FIG. 14D, staple driver member 350 drives staples 90 through the tissue of tubular anatomical structures 202, 402 and into staple forming pockets 414 of anvil 400. Staple forming pockets 414 deform the driven staples 90 into a "B" shape or a three-dimensional shape, for example, such that the formed staples 90 secure the ends of tissue together, thereby coupling tubular anatomical structure 202 with tubular anatomical structure 402.

After the operator has actuated (or "fired") stapling head 300 as shown in FIG. 14D, the operator rotates knob 130 to drive anvil 400 distally away from stapling head 300, thereby increasing the gap distance (d) to facilitate release of the tissue between surfaces 412, 322. The operator then removes instrument 10 from the patient, with anvil 400 still secured to trocar.

Figure 14E:
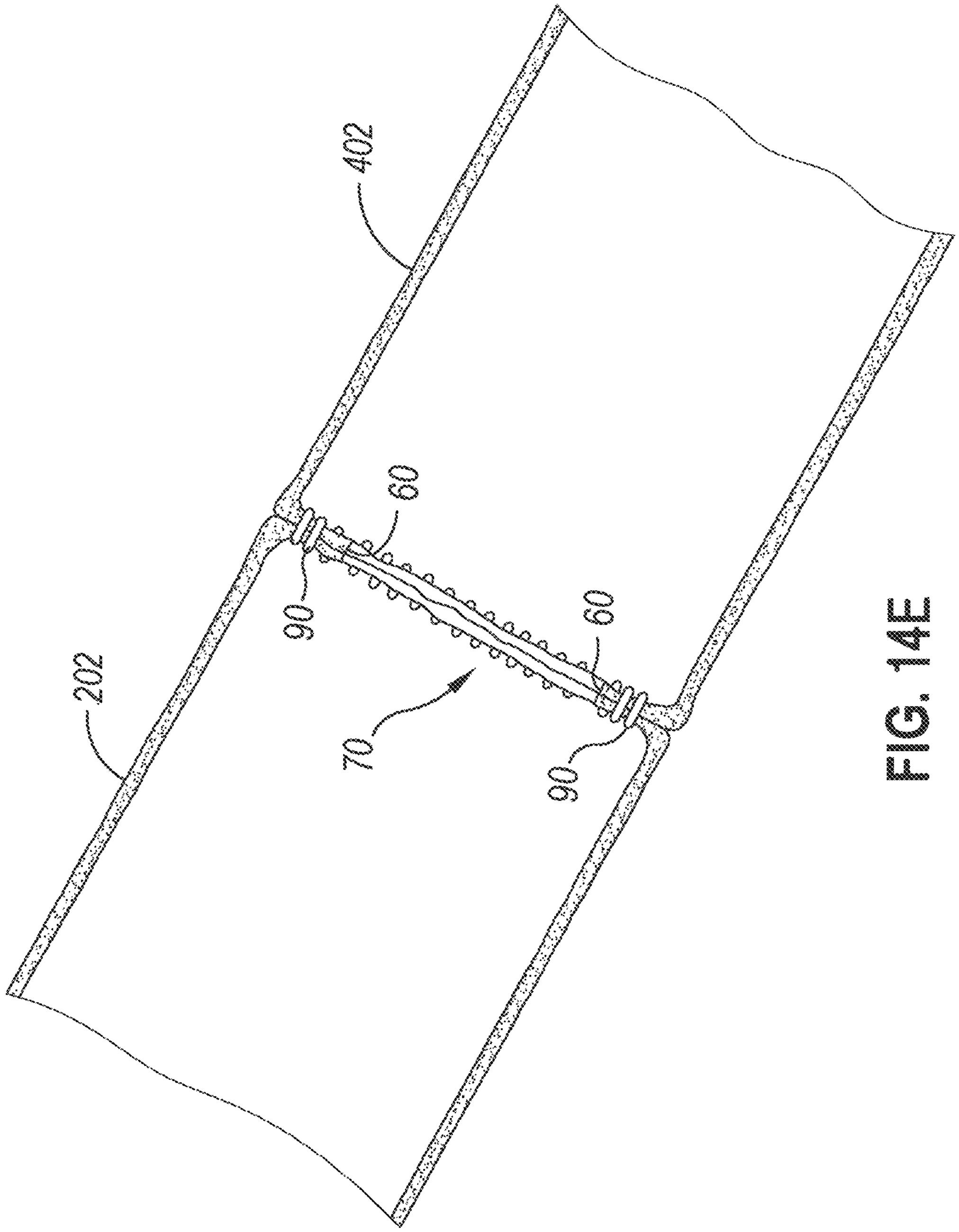
FIG. 14E depicts a cross-sectional side view of the first and second sections of the digestive tract of FIG. 14A joined together at an end-to-end anastomosis formed with the circular stapler of FIG. 8.

With instrument 10 removed, the tubular anatomical structures 202, 402 are left secured together by two annular arrays of staples 90 at an anastomosis 70 as shown in FIG. 14E. The inner diameter of the anastomosis 70 is defined by the severed edge 60 left by knife member 340.

Instrument 10 may be further constructed and operable in accordance with any of the teachings of the following references, the disclosures of which are incorporated by reference herein: in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; U.S. Pat. No. 8,910,847, entitled "Low Cost Anvil Assembly for a Circular Stapler," issued Dec. 16, 2014; U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and/or U.S. Pat. No. 10,709,452, entitled "Methods and Systems for Performing Circular Stapling," issued Jul. 14, 2020.

Figure 15:
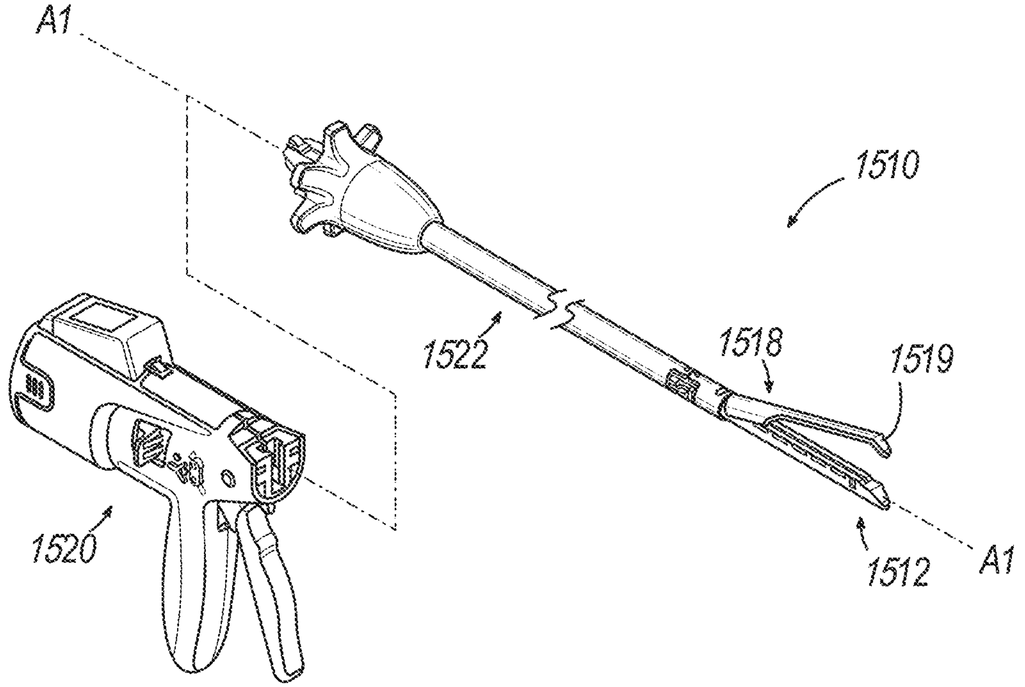
FIG. 15 depicts a perspective view of an example of a surgical stapling instrument having a modular end effector.

FIG. 15 shows another example of an instrument 1510 configured as a surgical stapler. Instrument 1510 includes a handle portion 1520 and a shaft 1522. Instrument 1510 has a modular configuration such that shaft 1522 is selectively removable from, and attachable to, handle portion 1520. Instrument 1510 is configured similarly to instrument 10 such that the operability and use of instrument 1510 is the same as described above for instrument 10 with the added feature of instrument 1510 being a modular configuration. With its modular configuration, instrument 1510 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 1510 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 1510 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 1510 or other instruments incorporated by reference herein.

It will be appreciated that end effector 1512 may be used in place of end effector 12 shown in FIG. 1. In some versions, end effector 1512 may be integrally formed with shaft 1522 or alternatively may be separately formed and then combined. In some versions, end effector 1512 may be provided for use in robotic systems. In such robotic systems, modular shaft 1522 having end effector 1512 may be attachable to a portion of the robotic system for use such that handle portion 1520 is replaced by components of the robotic system. Still in other examples, end effector 1512 may be adapted for use with a robotic system in a manner where end effector 1512 connects with the robotic system without necessarily connecting the entire modular shaft 1522. In view of the teachings herein, other ways to incorporate an end effector into a user operated or robotic operated instrument will be apparent to those of ordinary skill in the art.

II. METHOD FOR PRE-BENDING STAPLE TIPS USING ARBOR PLATE

Proper staple formation is important in all types of surgical staplers. If the grasped tissue is thicker than can be successfully accommodated by the staple height, the formation of the staple (referred to as the "b-form") may be too tight or small, which may cut off blood supply resulting in necrosis. If the grasped tissue is thinner than can be successfully stapled due to the staple height being too tall or wide, the formed staples may not be able to apply sufficient compression to effectively seal the tissue resulting in bleeding or oozing.

There are a number of areas for improvement regarding the staple forming process. As mentioned above, conventional staple forming technologies involve a pair of cooperating jaw members, where one of the jaw members receives a staple cartridge having rows of staples and the other jaw member defines an anvil having staple forming pockets aligned with the rows of staples in the cartridge. As the staples are driven upwards out of the staple channel (e.g., cavities or pockets) and into tissue by staple drivers and wedge sleds, the tips of the staple legs engage the surfaces of associated staple forming pockets of the anvil, which causes the staple legs to curl (i.e., bend or buckle), ultimately resulting in bent/formed staples.

Staple buckling against the anvil on the other side of tissue requires a high load and impacts the required force to fire the stapler. Generally, staple buckling against the anvil results in one or more peaks of a load profile for firing the stapler. As soon as a staple contacts the staple forming pocket of the anvil, a first peak of firing force occurs, since a higher force is necessary to buckle the staple against the anvil. Once the initial buckling happens, the tip of the staple may scrape along the staple forming pocket and the staple might experience a second bend or buckle, which imparts a second peak of firing force. Reducing the buckling of the staple, or the number of times the staple buckles, would significantly reduce the total amount of force required to fire a surgical stapler. Further, another problem with buckling against an anvil is that force of the staple being pushed against the anvil acts to separate the jaws of the surgical stapler. Curling staples without buckling against the anvil would alleviate this problem.

In order to achieve proper staple formation with the above approach (i.e., buckling against staple forming pockets of the anvil), the alignment between the staples in the staple channels/openings/cavities/pockets of the staple cartridge and the associated staple forming pockets of the anvil must be precise. Misalignment may result in improper staple formation, which may cause poor hemostasis, trauma on layers of tissue (e.g., tearing of tissue), or insufficient compression that leads to bleeding or oozing. Precise alignment requires very small tolerance ranges (e.g., thousandths of an inch), which makes manufacturing cartridges and associated anvils within these tolerance ranges rather difficult.

Another problem with having to match the staple pocket pattern of the staple cartridge with the staple forming pocket pattern of the anvil is that only one type of staple cartridge may be used with any given anvil of a particular pocket pattern. Using different staple cartridges with the same anvil (or swapping out with different anvils) currently requires complex modularity or adapters. In other words, currently, a same or similar staple pattern of a staple cartridge of conventional technology requires the use of the same anvil (i.e., the anvil having the same anvil pocket configuration) and a different staple pattern requires the use of a different anvil (i.e., an anvil having a different anvil pocket configuration).

Therefore, it would be beneficial to control staple forming without relying on staple forming pockets of the anvil. An anvil without staple forming pockets would be simpler and more economical to manufacture. A flat plated anvil, or an anvil with one or more simple troughs or clearance pockets, would also overcome the tolerance and alignment issues described above. In other words, even if a flat plate upper jaw (as opposed to a conventional anvil) that is used to hold the tissue in place happens to also deflect staple tips to assist with staple forming, the specific alignment previously required is not needed. Having a "universal" upper jaw or anvil without specific staple forming pockets would also allow a single stapler to be able to fire with all different types of cartridge reloads, minimizing the need for complex modularity or adapters as well as reload-to-gun lockouts (i.e., safety mechanisms that prevent a wrong cartridge type from being fired with a mismatched anvil), which is very beneficial.

The proposed cartridge designs described herein forms staples without buckling against a distant anvil on other side of tissue grasped between jaws of an end effector. Staple legs are plastically bent (i.e., curled) as they exit the cartridge, using features joined to the cartridge itself. This eliminates the need for pocket alignment, reduces force to fire since buckling is being reduced or eliminated, and provides high control of forming features because they are less impacted by tissue conditions. The proposed designs can allow for various types of cartridge reloads to be fired from the same surgical tool, eliminating the need for modularity. The proposed designs can also be embodied in all of endocutters as well as circular, curved, open, and linear staplers to reduce the need for anvil alignment, and compensate for deflection.

Spring forming machines bend shapes in wire fed by rollers, and around a movable set of arbors. The present disclosure applies that approach to a surgical stapler to form wire that captures tissue without buckling against a distant anvil. The wire can be a leg of a staple, the feeding occurs from the lifting of the driver, and the arbors are new features added at exit locations of cartridge pockets. The present disclosure thus provides staple cartridges with arbors at or near the cartridge deck and/or the tissue gripping features of staple cartridges (or in some cases a separate arbor plate disposed on top of the cartridge), where the arbors curl the staple legs as a driver lifts a staple out of the cartridge channel, in many cases without buckling or deflecting against an anvil. These features, or arbors, at or near the exit of staple pockets allow for improved control over the curl of staple legs and thus staple forming.

As used herein, the term "arbor" may refer to a short bar, shaft, stem, beam, spindle, guide, rod, post, or pin, or other deflection protrusion or wire (e.g., staple leg) bending or curling surface. In some examples, an "arbor" may act as a mandrel, such as a cylindrical rod around which metal (e.g., staple leg) is formed or shaped. In some examples, an "arbor" may be integrally formed as part of a cartridge channel, such as a protrusion of a sidewall of a cartridge channel, or staple driver, or other stapler component. In yet other examples, an "arbor" may be a separate and distinct component that is capable of being removed without destroying the integrity of the other stapler components. In some examples, "arbors" may be part of the staple cartridge deck, be part other features located on the cartridge deck (e.g., tissue gripping features or gripping surface technologies), or be part of an arbor plate configured to be disposed on top of staple cartridges or decks. In each case, the arbors are configured to interact with the staple (e.g., staple legs) as the staple exits the staple pockets of the staple cartridge.

Using the proposed designs described herein, tolerances that control the staple shape are controlled in manufacturing of the cartridge (or arbor plate) component only, since the anvil can be made without staple forming anvil pockets and simply be used to hold tissue against the staple cartridge. This eliminates the need for the strict pocket alignment described above. Once tolerances are satisfied for a particular cartridge or arbor plate design, variables are set and the cartridges/plates can be manufactured. The proposed cartridge designs impart force to fire advantages as well. For example, the curling load is resolved in one jaw—the cartridge jaw—and not across movable jaws. Further, the continuous bending of the staple wire is more controlled and requires a lower load than buckling short segments as previously done. In other words, continuous staple bending provides a lower steady load value as compared to multiple buckling peak load values of conventional staple forming methods, since after the initial bending load the load value required to finish the firing plateaus. Further, with curling staples as soon as the staple leaves the cartridge, the reduced or eliminated impact against the anvil also reduces or eliminates the force acting to separate the jaws. Pre-curling or pre-bending the staples also provides the ability to have staple formations tighter than the distance between jaws, since the tips of the staples may not need to extend through the tissue to reach the anvil in order to curl/bend. Correct positioning of the proposed staple forming features, or arbors, described herein also allows for positive retention of staples in the staple cartridges without the need for a separate cover or cap, particularly for non-titanium staples that may have less natural spring force.

The disclosed arbor plate for pre-bending or pre-curling staple tips serves two purposes. The first is to move the peak pre-bending load of the wires into the manufacturing process. The second is to eliminate the need for staple retainers because the staples become locked into the device once pre-bent.

A standard stapler housing (cartridge housing) or deck is typically loaded with staples and supported from below the drivers so that a high load can be applied to bend the staples without moving the drivers. The tips of the staples generally protrude from this standard housing or deck. An arbor plate, complete with arbor surfaces in or on each pocket or channel of the plate, can be positioned over the housing, and then pressed onto the housing with a machine that can generate a high load. The step of pressing the arbor plate onto or over the tips of the staples protruding from the housing bends each tip of the staples into the curling state, which is the peak load of firing with this system.

This may be especially advantageous in a circular stapler since all the staples fire at once (i.e., all staples are formed at the same time and the knife fires and has to break through a plastic washer on the inside of the circular staple housing/cartridge or deck), and a very high load is usually generated when firing in a traditional way against an anvil. In some cases, the force to fire may be as high as 300 pounds or more. That load usually stretches the system, and can result in poorly formed staples and high firing loads. Therefore, reducing the force to fire in circular staplers may be very advantageous. The disclosed approach using an arbor plate takes that high-force step into the device manufacturing realm (as opposed to the user), where greater control can be applied. The staples can be pre-bent, which greatly lessens the normally high firing load. In other words, when the staple tips are pre-bent, firing takes place at the lower load curve and a lower force is required to fire. Since the staples are just pre-bent and not fully extending from the top of the plate, the normal steps of closing the jaws on tissue and firing are still the same to the user with this approach as compared to the traditional approach using an anvil.

Figure 16:
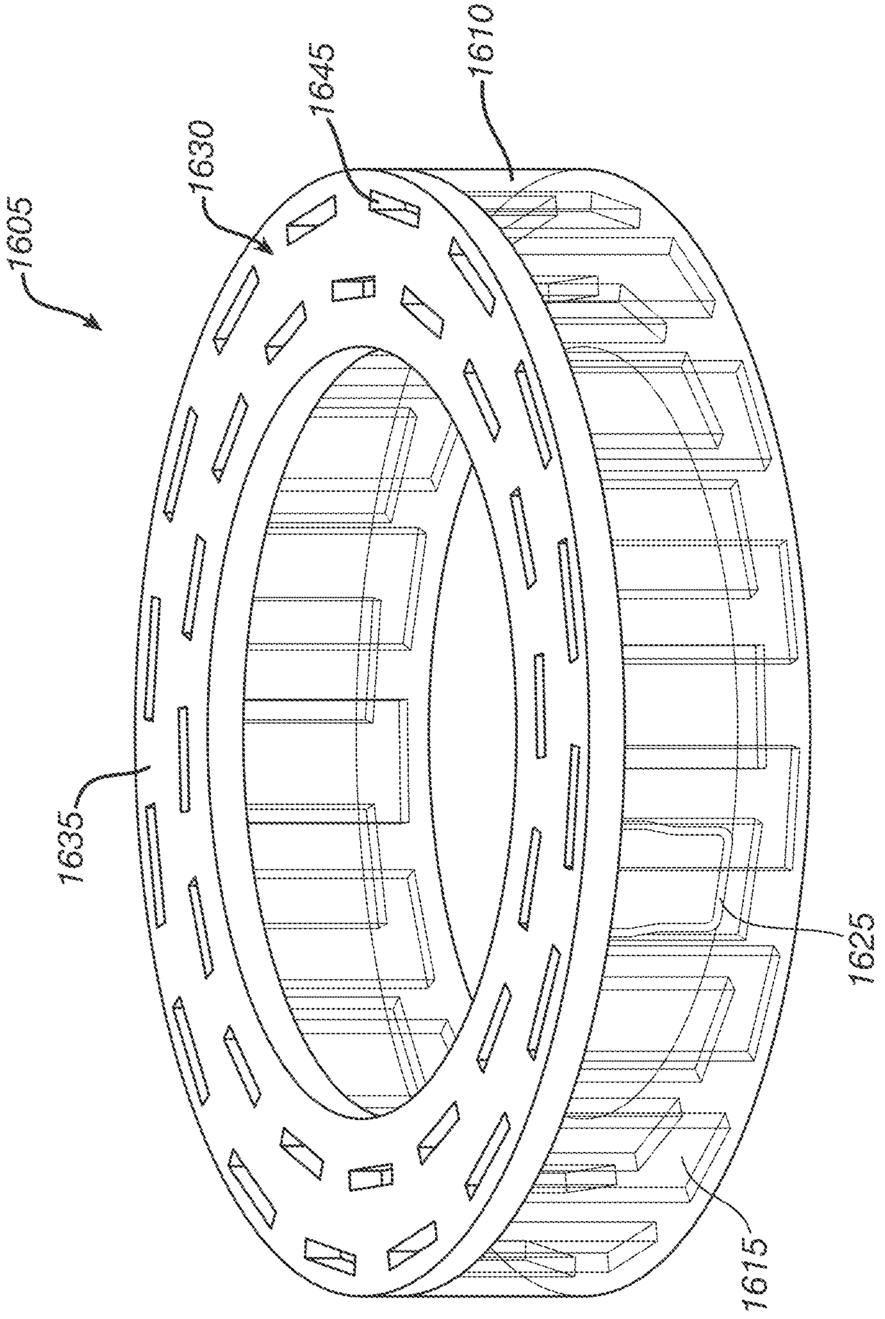
FIG. 16 depicts a perspective view of a staple deck having a staple forming plate disposed on a staple deck body according to one embodiment.

FIG. 16 depicts a perspective view of a staple cartridge (i.e., staple housing or deck) having an arbor plate disposed on a staple cartridge body according to one embodiment. A staple cartridge 1605 is shown in FIG. 16. In one embodiment, as shown in FIG. 16, the staple cartridge 1605 may be an annular staple cartridge 1605 configured to fit within a circular surgical stapler, or housing/deck that may be part of a circular stapler. Similar embodiments may also be applied to linearly-arranged cartridges that can be placed within linear staplers or endocutters. The staple cartridge 1605 may include at least one annular row of staple cavities 1615. In some examples, the staple cartridge 1605 may include several annular rows of staple cavities 1615. The example in FIG. 16 illustrates an annular staple cartridge 1605 having two annular rows of staple cavities 1615. The annular row(s) of staple cavities 1615 are configured to hold staples 1625 having staple legs.

An annular arbor plate 1630 (also referred to herein as a staple forming plate 1630) may be configured to be coupled to the staple cartridge 1605 using screws, welds, fasteners, etc. (not pictured). The annular arbor plate 1630 includes a plurality of annular pockets or channels 1645 corresponding to the staple cavities 1615. In this way, the staple cartridge 1605 of FIG. 16 has two annular rows of annular channels 1645 that match up or align with the annular rows of corresponding staple cavities 1615. As discussed in more detail below with regard to FIG. 17, each annular channel 1645 of the plurality of annular channels 1645 includes a feature that curls the staple legs upon a firing of the staples 1625. As shown and described below, the feature may include a curved sidewall and/or an arbor.

The staple cartridge 1605 includes a cartridge body 1610 that may be annular or ring shaped, as shown in FIG. 16. The cartridge body 1610 includes an outer sidewall and an inner sidewall spaced apart from the outer sidewall and having a diameter less than a diameter of the outer sidewall. The cartridge body 1610 also includes a top surface 1622 and a bottom surface opposite the top surface, where both the top and bottom surfaces span between the outer and inner sidewalls, such that the staple cartridge is cylindrically ring shaped.

Figure 17:
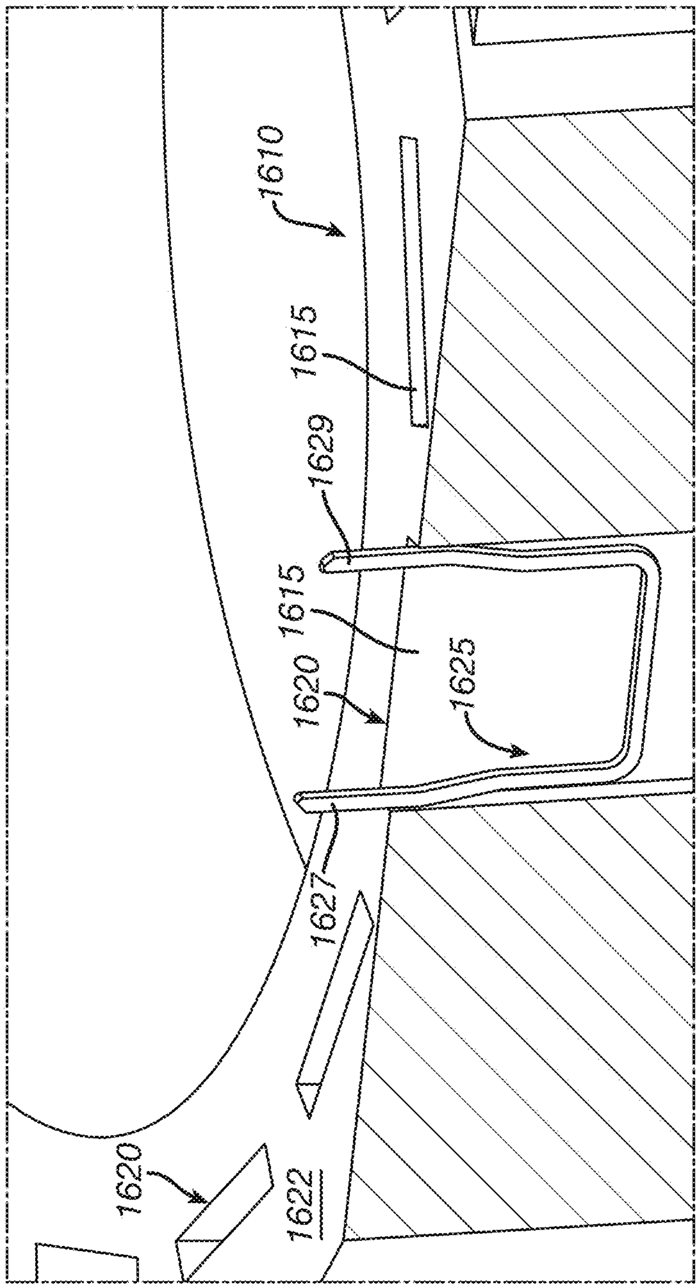
FIG. 17 depicts a partial cross sectional view of the deck body of the staple cartridge of FIG. 16.

As mentioned above, the staple body 1610 includes a staple cavity 1615 having a staple aperture 1620 in a top surface 1622 of the cartridge body 1610, as shown more clearly in FIG. 17. The staple cavity 1615 is configured to receive a surgical staple 1625 such that the staple 1625 is vertically movable within the staple cavity 1615 along a longitudinal axis of the staple cavity 1615. In other words, the staple 1625 can move up and down within the staple cavity 1615. However, oftentimes staple legs of the staples 1625 are bent outwards (i.e., up and away from a base of the staple 1625) during manufacturing so that the staples 1625 need to be compressed (i.e., the staple legs are squeezed together) in order for the staple 1625 to be inserted into the staple cavity 1615 of the staple cartridge 1605. In this way, once inserted, the natural spring force of the staple legs push against inner sidewalls of the staple cavity 1615 thus holding the staple 1625 relatively in place within the staple cavity 1615.

In an embodiment, the staple cartridge 1605 includes a staple forming plate 1630, or annular arbor plate 1630, configured to be attached to the top surface 1622 of the cartridge body 1610. The staple forming plate 1630 includes a tissue contacting top surface 1635 and a bottom surface 1640 opposite the tissue contacting top surface 1635. See FIG. 18. The staple forming plate 1630 includes a staple forming channel 1645 defined in, and extending through, the staple forming plate 1630 between the tissue contacting top surface 1635 and the bottom surface 1640. When the staple forming plate 1630 is attached to the top surface 1622 of the cartridge body 1610, as shown in FIG. 16, the staple forming channel 1645 is aligned with the staple aperture 1620 of the staple cavity 1615. As shown in FIG. 16, the staple forming plate 1630 includes two annular rows of staple forming channels 1645, where each staple forming channel 1645 is aligned with a corresponding staple cavity 1615.

FIG. 17 depicts a partial cross sectional view of the cartridge body 1610 of the staple cartridge 1605 of FIG. 16. Specifically, FIG. 17 depicts a cut away view of one of the staple cavities 1615 having a staple 1625 placed or loaded therein. As shown in FIG. 17, the staple 1625 includes a first staple leg 1627 and a second staple leg 1629, where the two staple legs 1627, 1629 are joined together at a base or crown (the bottom portion of the staple 1625 in the orientation shown in FIG. 17). The staple cavity 1615 is configured to receive the staple 1625 such that a portion of the first staple leg 1627 and a portion of the second staple leg 1629 extend out of the staple aperture 1620 in the top surface 1622 of the cartridge body 1610. The amount of each staple leg 1627, 1629 that extends past the top surface 1622 of the cartridge body 1619 can vary. In the example shown in FIG. 17, about one third of the length of each staple leg 1627, 1629 extends beyond the staple aperture 1620. In one example, the staple 1625 may be loaded into the staple cartridge 1605 in this orientation. In another example, a shim-sled may be used to put the staple 1625 into this configuration. In this example, the shim-sled could pass through the staple cartridge 1605 to slightly raise the staples 1625 to this orientation (i.e., where the tip portion extends out of the staple aperture 1620 in the top surface 1622 of the cartridge body 1610). This may be done prior to packaging the cartridges 1605 for shipment to the end user/customer. In some embodiments, the distance between the staple legs 1627, 1629 at their respective tips may be larger than a distance between the staple legs 1627, 1629 at the crown.

Figure 18:
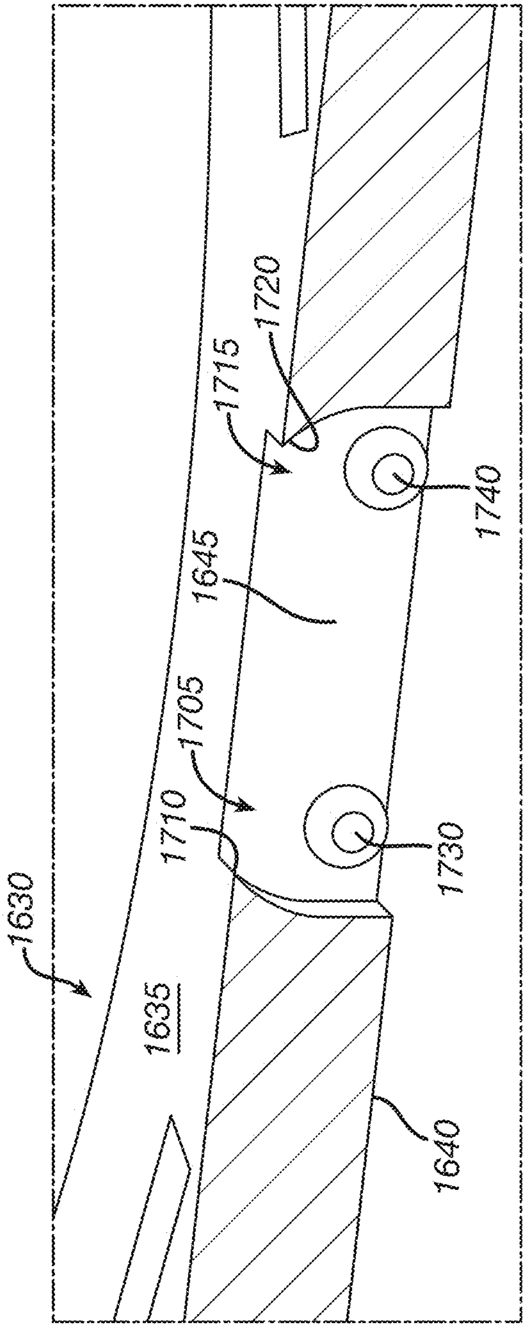
FIG. 18 depicts a partial cross sectional view of the staple forming plate of FIG. 16.

FIG. 18 depicts a partial cross sectional view of the staple forming plate 1630 of FIG. 16. Specifically, FIG. 18 depicts a cut away view of one of the staple forming channels 1645. As shown in FIG. 18, the staple forming channel 1645, also referred to herein as an annular channel 1645, includes one or more features configured to curl, bend, or shape staple legs 1627, 1629 as the staples 1625 are pushed through the staple forming channel 1645, as is described in more detail below.

The staple forming channel 1645 includes a first staple forming region 1705 configured to receive the portion of the first staple leg 1627 extending out of the staple aperture 1620. In other words, as shown more clearly in FIG. 19, a length of the portion of the staple legs 1627, 1629 that extend beyond the staple aperture 1620 in the top surface 1622 of the cartridge body 1610 corresponds to, or is about as equal as, the depth of the staple forming channel 1645. The first staple forming region 1705 includes a first curved surface 1710 disposed adjacent the tissue contacting top surface 1635 of the staple forming plate 1630. In one example, the staple forming channel 1645 may be rectangular in shape and defined by four walls, including two opposing longer walls and two opposing shorter sidewalls. In this example, the staple legs 1627, 1629 or portions thereof may abut and be disposed along the two opposing shorter sidewalls. The first curved surface 1710 may be an upper part of one of the sidewalls (e.g., the shorter opposing sidewalls). In another example, the first curved surface 1710 may be another component, such as round peg or pin (e.g., arbor) or a wedge with a curved surface, that is disposed at the upper end of the opposing sidewalls. See FIG. 20, for example.

The first staple forming region 1705 further includes a first arbor 1730 offset laterally from the first curved surface 1710 towards a center of the staple forming channel 1645. With this arrangement, the portion of the first staple leg 1627 that extends beyond the staple aperture 1620 in the top surface 1622 of the cartridge body 1610 is disposed between the first arbor 1730 and the first curved surface 1710, as shown and described below with reference to FIG. 19. The first arbor 1730 may be a short bar, shaft, stem, beam, spindle, guide, rod, post, or pin.

The staple forming channel 1645 also includes a second staple forming region 1715 configured to receive the portion of the second staple leg 1629 extending out of the staple aperture 1620. The second staple forming region 1715 includes a second curved surface 1720 disposed adjacent the tissue contacting top surface 1635 of the staple forming plate 1630. Similar to above, the second curved surface 1720 may be an upper part of one of the sidewalls (e.g., the shorter opposing sidewalls) that define the staple forming channel 1645 or a separate component having a curved surface that is disposed at the upper end of the sidewalls.

The second staple forming region 1715 further includes a second arbor 1740 offset laterally from the second curved surface 1720 towards the center of the staple forming channel 1645. With this arrangement, the portion of the second staple leg 1629 that extends beyond the staple aperture 1620 in the top surface 1622 of the cartridge body 1610 is disposed between the second arbor 1740 and the second curved surface 1720, as shown and described below with reference to FIG. 19. The second arbor 1734 may also be a short bar, shaft, stem, beam, spindle, guide, rod, post, or pin.

In one embodiment, the first arbor 1730 and second arbor 174 may each extend partially into the staple forming channel 1645 from either of the two opposing longer walls of the staple forming channel 1645. In another embodiment, the first arbor 1730 and second arbor 1740 may each extend away from both of the opposing longer walls of the staple forming channel 1645 towards each other, but with a small gap or interruption therebetween. Each of these arrangements allows for the crown of the staple 1625 to move past the first and second arbors 1730, 1740 as the staple 1625 is forced into and through the staple forming channel 1645, thus allowing the staple 1625 the exit the staple forming channel 1645.

Figure 19:
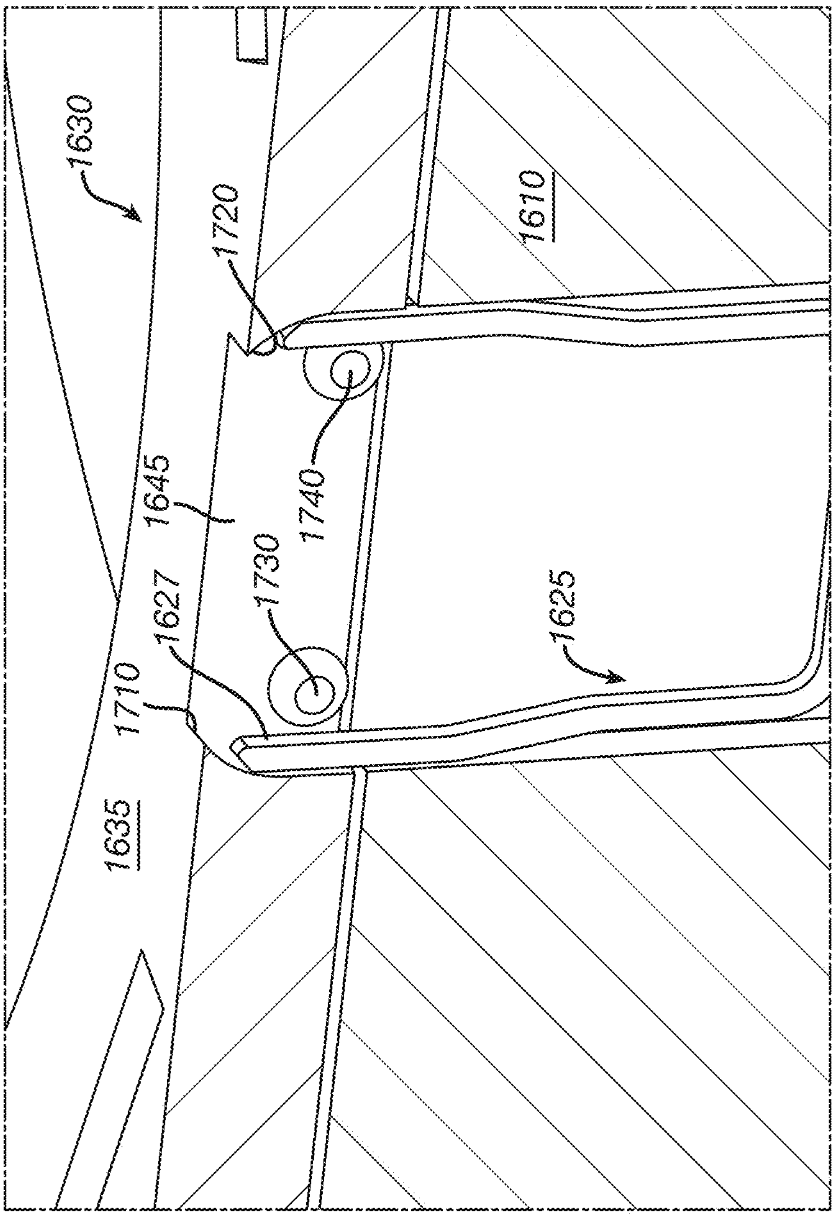
FIG. 19 depicts a partial cross sectional view of the staple forming plate of FIG. 18 disposed on the deck body of FIG. 17.

As shown in FIGS. 18 and 19, the first curved surface 1710 and the second curved surface 1720 are curved towards each other. In this way, when the staple forming plate 1630 is attached to the top surface 1622 of the cartridge body 1610, the first curved surface 1710 and the second curved surface 1720 are configured to bend a tip of the portion of the first staple leg 1627 and a tip of the portion of the second staple leg 1629, respectively, laterally relative to the longitudinal axis of the staple cavity 1615. In other words, the first and second curved surfaces 1710, 1720 bend the tips of the staple legs 1627, 1629 towards each other. Placing and attaching the staple forming plate 1630 happens before firing the staples 1625, such that the tips of the staples 1625 are pre-bent before firing.

FIG. 19 depicts a partial cross sectional view of the staple forming plate 1630 of FIG. 18 disposed on the cartridge body 1610 of FIG. 17. As shown in FIG. 19, the staple 1625 is received in a staple cavity 1615 and a staple forming channel 1645, where portions of each staple leg 1627, 1629 extend past the top surface 1622 of the cartridge body 1610. As the staple forming plate 1639 is positioned onto and coupled to the cartridge body 1610, the tips of the first and second staple legs 1627, 1629 contact the first and second curved surfaces 1710, 1720 and are curled or bent towards each other and around (at least partially) the first and second arbors 1730, 1740. As the staples 1625 are fired (e.g., on tissue), the staples 1625 are driven upward or out of the staple cavities 1615 and pushed through the staple forming channels 1645. The pre-bent tips of the staple legs 1627, 1629 continue bending or curling towards each other and through tissue as the staples 1625 are being pushed out of the cavities 1615. In other words, when the staple 1625 is advanced out of the staple cavity 1615 and through the staple forming channel 1645 of the staple forming plate 1630, the first staple leg 1627 and second staple leg 1629 are curled toward each other based on the first staple leg 1627 and second staple leg 1629 contacting the first curved surface 1710 and second curved surface 1720, respectively. The amount and shape of the bend of the staples 1625 depends on the degree of curvature of the first curved surface 1710 and second curved surface 1720, as well as the placement and position of the first and second arbors 1730, 1740.

Figure 20:
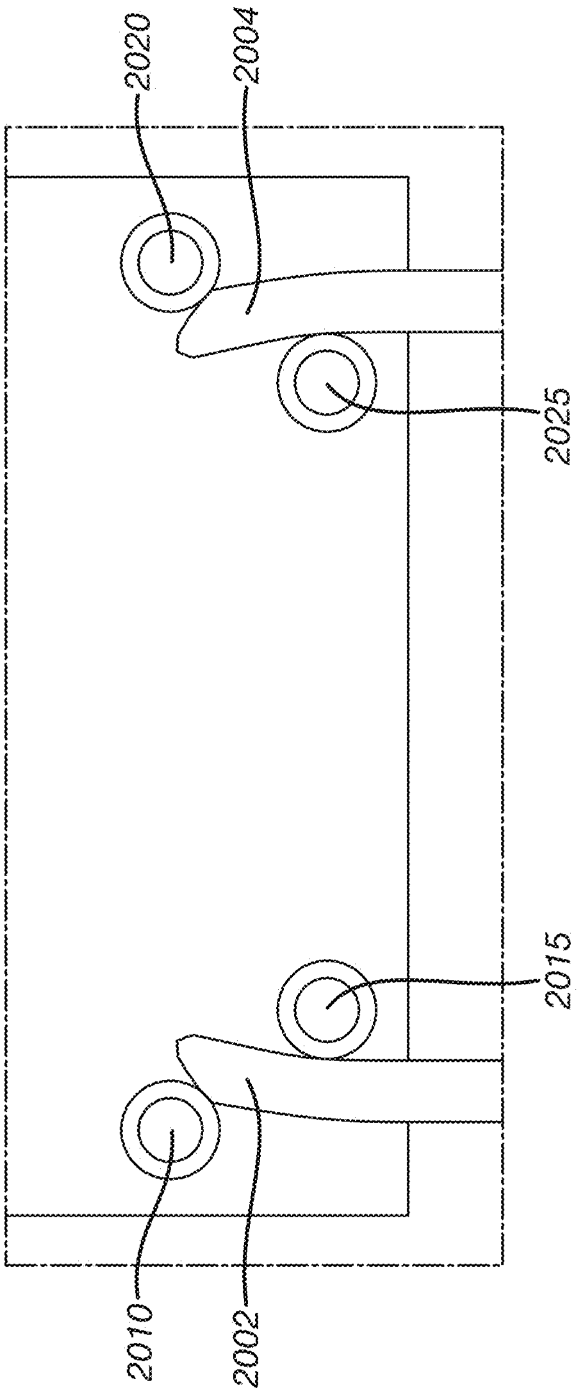
FIG. 20 depicts staple forming features according to another embodiment.

Pre-bending tips of staple legs in this manner allows for positive retention of staples 1625 in the staple cavities 1615 prior to firing the staples 1625, which reduces or eliminates the need for a separate staple retainer component. The staple cartridge 1605 is configured to be used with a surgical stapler, and the first curved surface 1710 and the second curved surface 1720 are configured to retain the staple 1625 in the staple cavity 1615 prior to firing the surgical stapler. The pre-bending of the staples 1625 also has an impact on the force required to fire the staples 1625, as shown in FIG. 20, described below. In other words, with pre-bending staple tips, the load to continue bending the staple 1625 is low.

In some examples, as mentioned above, the staple forming plate 1639 is positioned or pressed onto the top of the cartridge body 1610 in such a way that can generate a high load (i.e., a high enough load to bend the staple tips). In some cases, a machine may be used to press the staple forming plate 1639 on top of the staple tips extending out of the cartridge body 1610. In this way, whatever is used to generate the high load to pre-bend the staple tips essentially removes the need for that load by the firing system of the surgical stapler when a user (surgeon or robot) fires the stapler.

As mentioned above, the first curved surface 1710 and/or the second curved surface 1720 may be another component, such as round peg or pin (e.g., arbor) that is disposed at the upper end of the opposing sidewalls of the staple forming channel 1645. FIG. 20 depicts staple forming features according to another embodiment. As shown in FIG. 20, first and second staple legs 2002, 2004 are each disposed between a set of arbors. Specifically, a first staple leg 2002 is disposed between an upper arbor 2010 and a lower arbor 2015, and a second staple leg 2004 is disposed between another upper arbor 2020 and another lower arbor 2025. During firing, the staple legs 2002, 2004 are forced through or between the sets of arbors 2010, 2015 and 2020, 2025, causing the tips of the staple legs 2002, 2004 to bend. As the staples legs 2002, 2004 are continually pushed out of the staple cavity, the staple legs 2002, 2004 continue to bend or curl toward each other as the staple legs 2002, 2004 advance into tissue. The hatched portions of the staple legs 2002, 2004 in FIG. 20 indicate where the staple legs 2002, 2004 experience deformation forces.

In one embodiment, the first curved surface 1710 and the second curved surface 1720 described above may be replaced by additional arbors, such as the upper arbors 2010, 2020 of FIG. 20, located at an end of the opposing sidewalls adjacent the tissue contacting top surface 1635 of the staple forming plate 1630.

Figure 21:
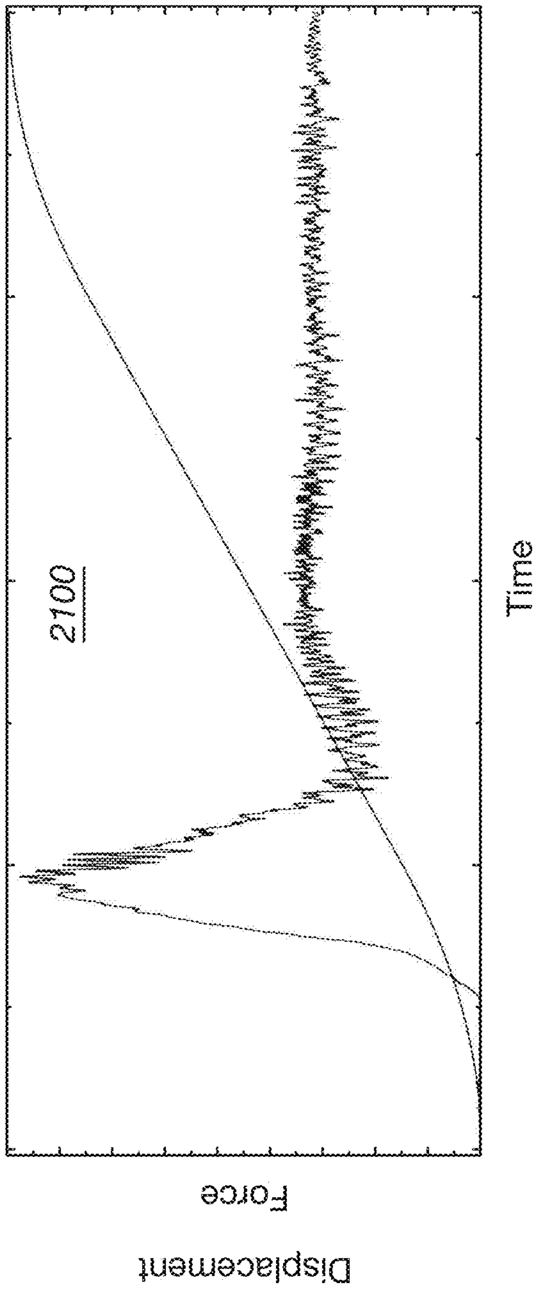
FIG. 21 depicts a graph illustrating a load profile at different times or stages of a staple firing process according to one embodiment.

FIG. 21 depicts a graph 2100 illustrating a load profile at different times or stages of a staple firing process according to one embodiment. In other words, the time on the x-axis may represent the firing progress from 0% to 100% completion. Specifically, the force curve of FIG. 21 shows a load profile of firing the staple legs 2002, 2004 through the sets of arbors 2010, 2015 and 2020, 2025, as shown in FIG. 20. As shown in FIG. 21, the peak load of firing through arbors occurs at an initial stage when the tips of the staple legs 2002, 2004 are bent. After that, a continuous bend requires less than half the force required to initially bend the staple legs 2002, 2004. This illustrates that using staple forming features to pre-bend staples prior to firing will reduce the force to fire significantly. In other words, if tips of staples are already bent prior to firing, the load profile of the actual firing process would not have the peak that is present in FIG. 21, thus reducing the firing load required for firing the staples into tissue. The graph of FIG. 21 may also represent a height of the staple driver, where the height of the staple driver increases from the beginning of the firing process to the completion of the firing process. In this case, the absolute values would change depending on the unformed staple height. In other words, a staple driver would need to travel (i.e., increase in height) one distance to deploy a short staple, but would need to travel another distance to deploy a longer staple.

Figure 22A:
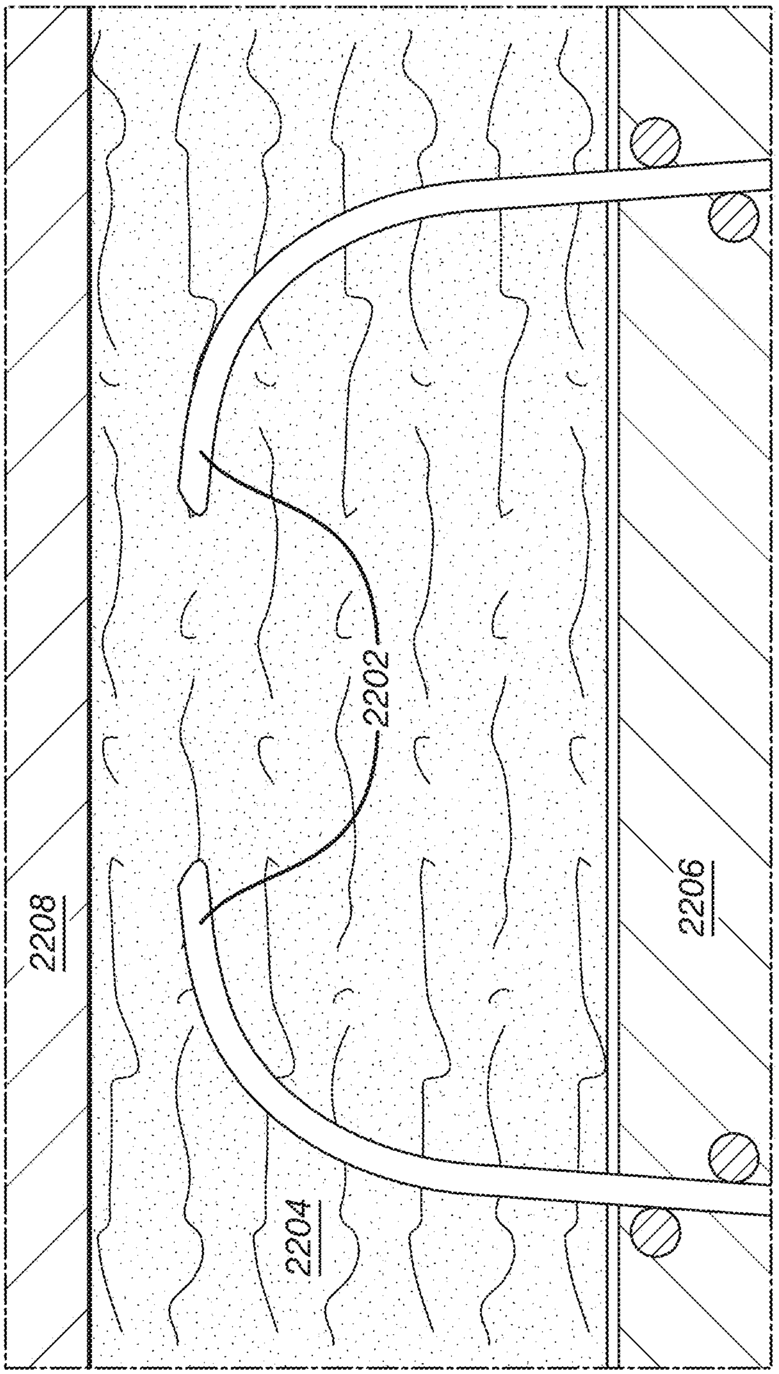
FIGS. 22A-C depict using an additional layer of material to allow staple legs to fully penetrate and curl in tissue after exiting a staple cartridge but before reaching an anvil.
Figure 22B:
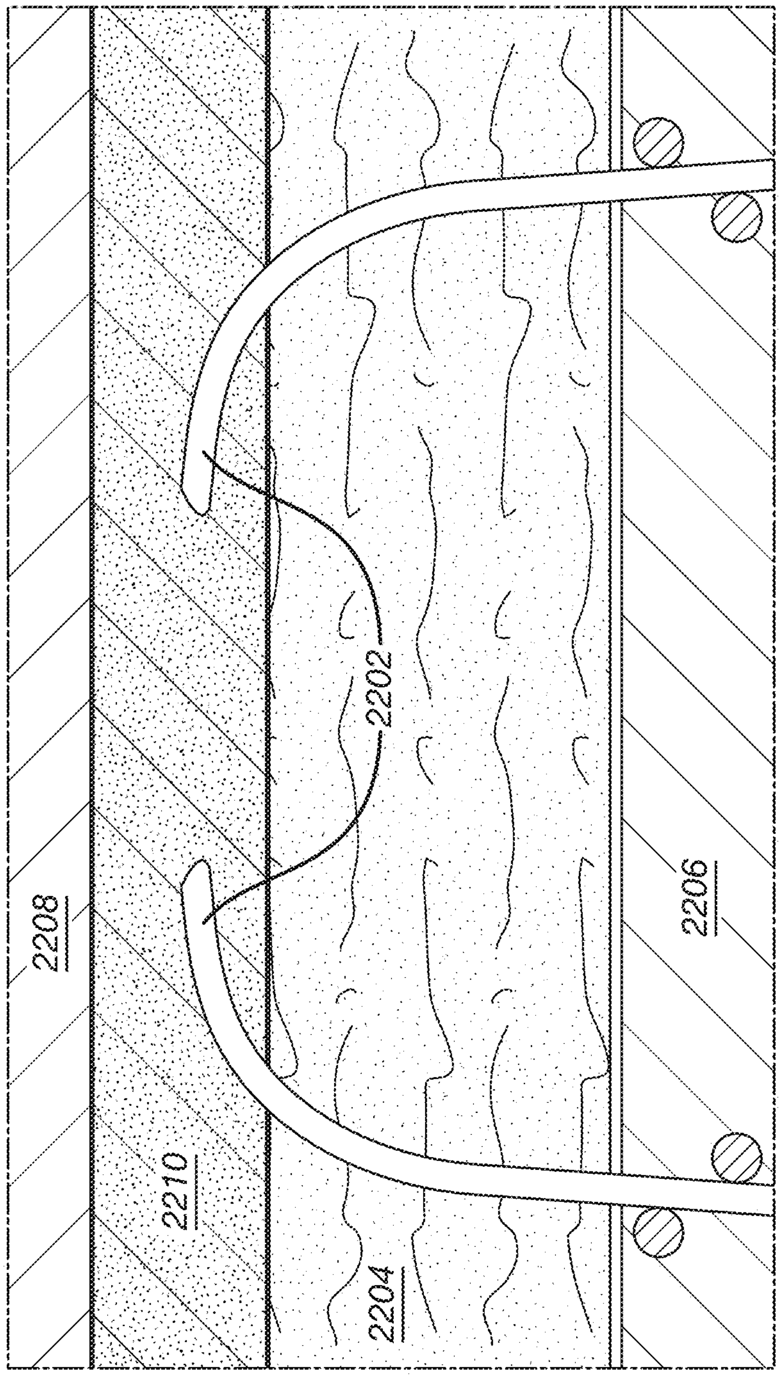
Figure 22C:
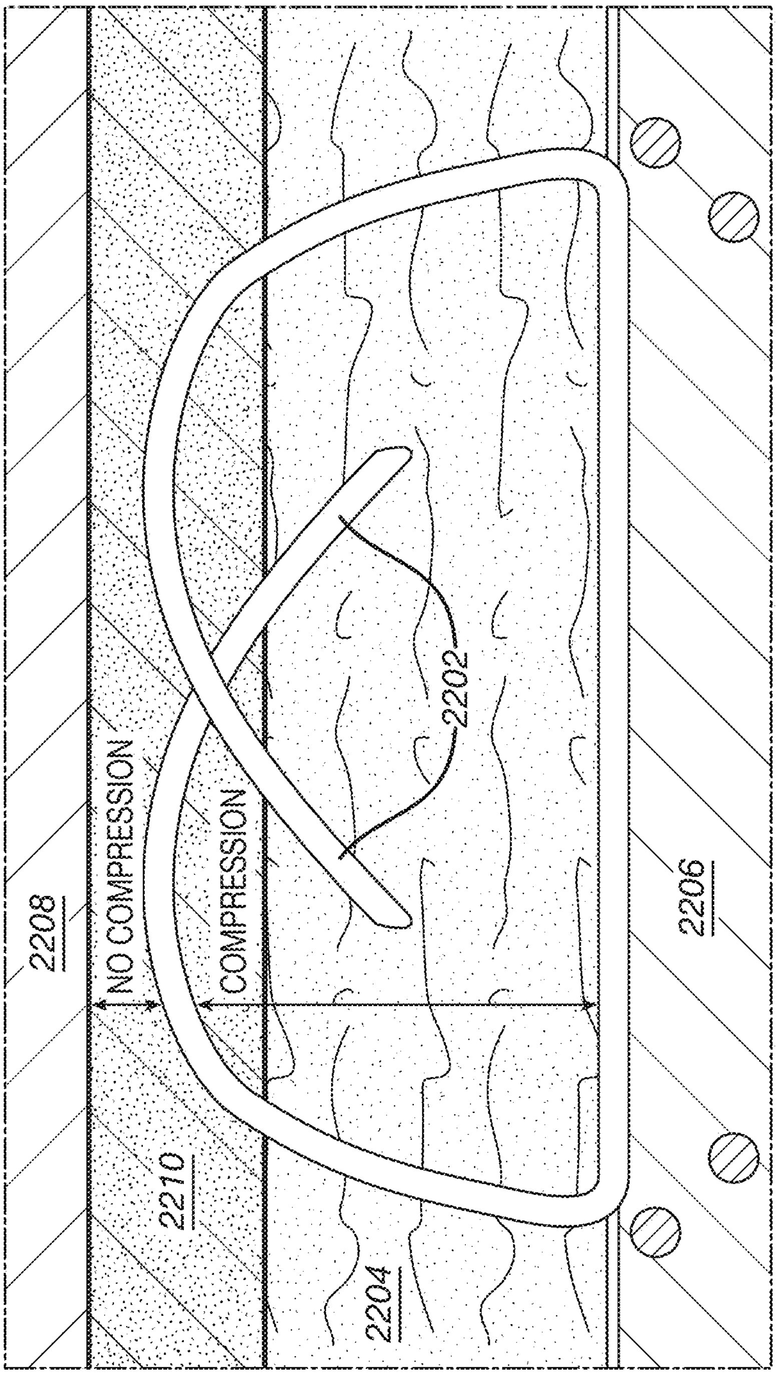

FIGS. 22A-C depict using an additional layer of material to allow staple legs to fully penetrate and curl in tissue after exiting a staple cartridge but before reaching an anvil. In staple formation, there are advantages in having staple tips penetrate all the way through the tissue before curling or bending in order to capture or "gather" all of, or the right amount of, tissue. This is referred to as a staple reaching across the tissue gap. However, in some embodiments, if the staple tips begin to curl too soon or at too steep of an angle (variables that are controlled by the positioning of the staple forming features described above), an appropriate amount of tissue may not be gathered or captured. This is shown in FIG. 22A, which depicts staple legs 2202 penetrating and curling in tissue 2204 after exiting a cartridge 2206 but before reaching the anvil 2208. In the example shown in FIG. 22A, once the staple legs 2202 are fully curled (i.e., formed), since the staple legs 2202 did not penetrate all the way through the tissue 2204, the tissue compression may not be adequate.

In one example, allowing the staple tips to scrape an anvil surface as the staples bend or curl may be appropriate. In another example the anvil may include clearance pockets, which may be dome shaped spaces or cutouts in the bottom surface (e.g., tissue contacting surface) of the anvil that allow a staple to be received in as the staple extends out of the tissue and bends or curls back into the tissue. In this example, the anvil may have a trough along the entire length of the anvil on the tissue contacting side that allows for movement of the staple in this manner.

In yet another example, a layer of material may be disposed between the anvil and the tissue that allows the staples to reach across the tissue gap in order to capture or gather the tissue, but without contacting the anvil. FIGS. 22B and 22C illustrate a layer of material 2210 disposed between the anvil 2208 and the tissue 2204. As shown in FIG. 22B, the tips of the staple legs 2202 are curled before reaching the anvil 2208, but also penetrate through the entire tissue layer 2204. As shown in FIG. 22C, the staple legs 2202 are formed without contacting the anvil 2208, but also captures the entire tissue layer 2204 due to the extra layer of material 2210 disposed between the anvil 2208 and the tissue 2204. As shown in FIG. 22C, the formed staple legs 2202 allows for compression of the tissue 2204 and part of the layer of material 2210. The material may be a compressible hemostat material such as, for example, oxidized regenerated cellulose ("ORC") or a bio-absorbable foam of the types described in U.S. Pat. No. 10,363,031, entitled "Tissue Thickness Compensators For Surgical Staplers," issued Jul. 30, 2019, the disclosure of which is incorporated by reference herein, in its entirety.

Figure 23:
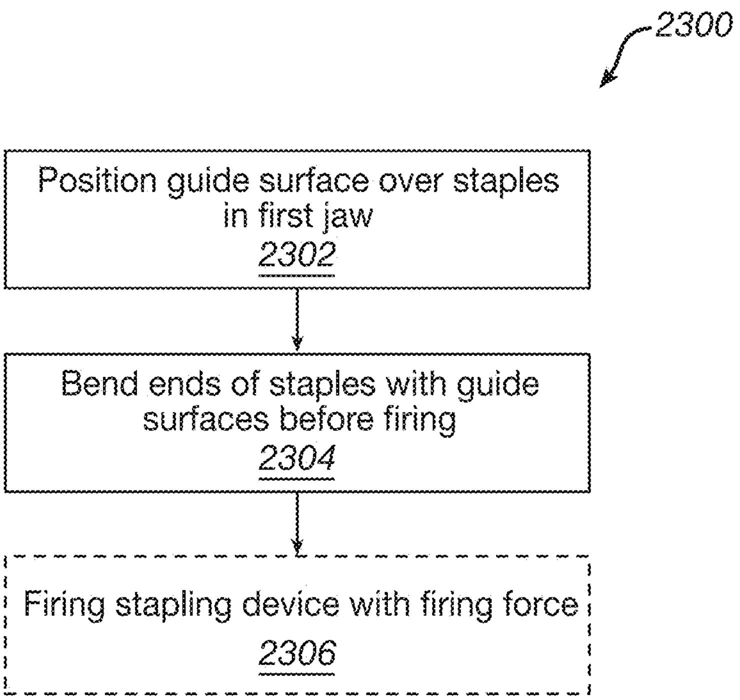
FIG. 23 is a flowchart of a method of forming staples between opposing jaws of a stapling device according to one embodiment.

FIG. 23 is a flowchart of a method 2300 of forming staples between opposing jaws of a stapling device according to one embodiment. In one embodiment, the method 2300 may include positioning a set of guide surfaces or guide features (e.g., staple forming features) over each of a plurality of staples loaded in openings of a staple cartridge of a first jaw (e.g., cartridge jaw) of the opposing jaws, where each staple includes a crown with staple legs extending therefrom, where ends of the staple legs opposite the crown exit through the openings (Block 2302). As described above with respect to FIGS. 16-19, the staples may be loaded in the openings of the first jaw such that a portion of (e.g., the ends of) the staple legs extend out of the openings. When positioning the set of guide surfaces over the staples, the staples may be supported at the crown of the staple. The method 2300 may further include attaching the guide surfaces to the first jaw adjacent to the openings.

The method 2300 may further include bending the ends of the staple legs with the guide surfaces (Block 2304). As described above with respect to FIGS. 16-19, bending the ends of the staple legs include bending, by the guide surfaces, the ends of the staple legs that extend out of the openings as the guide surfaces are positioned over the staples. The staples may be retained, by the guide surfaces, in the openings of the first jaw prior to firing the stapling device. Retaining the staples in the staple cavities eliminates the need for a separate staple retention member or component.

The method 2300 may further include firing the stapling device with a firing force after bending the ends of the staple legs with the guide surfaces, where firing the stapling device causes the staples to exit the openings (Block 2306). As discussed above, since the staple tips are pre-bent at this step, the force to fire is greatly reduced.

The step of firing the staple device (Block 2306) causes the staple legs to continue bending against the guide surfaces as the staples exit the openings. Causing the staple legs to continue bending may include forcing the staple legs past the guide surfaces using the firing force. In one example, causing the staple legs to continue bending may include curling the staple legs using the guide surfaces of the first jaw only (i.e., not using the second or anvil jaw to facilitate bending/curling). In this regard, causing the staple legs to continue bending may include curling the staple legs while avoiding contact with a second jaw of the opposing jaws (i.e., anvil jaw). In this example, causing the staple legs to continue bending may include curling the staple legs without buckling the staple legs (e.g., buckling against an anvil jaw).

In some embodiments, one or more of the guides (e.g., arbors or guide surfaces) or staple forming surfaces may be movable, releasable or detachable. For example, the guides/arbors or staple forming surfaces may be released with the fully curled staple legs after the staple forming is complete. In this case, the guides/arbors may be made out of a bioabsorbable material. In another example, the staple cartridge may contain a mechanism or device that retracts the guides/arbors. In other words, the guides/arbors may be moved out of the way to allow the staples to deploy or exit the cartridge pocket. In yet another example, the guides/arbors may be designed to allow the staple crown to pass through the guides/arbors. Thus, the staple cartridges described here may use guides/arbors of the types described in: U.S. patent application Ser. No. 18/781,551, entitled "Staple Cartridge Containing Forming Surfaces That Bend Staple Legs Upon Exiting"; U.S. patent application Ser. No. 18/781,578, entitled "Deployable Arbor Sets That Break Away From Staple Cartridge"; and U.S. patent application Ser. No. 18/781,583, entitled "Multi-Part Staple With Separate Legs And Crown To Facilitate Staple Release From Arbors," the disclosures of which are incorporated by reference herein, in their entirety.

III. STAPLE CARTRIDGE CONTAINING FORMING SURFACES THAT BEND STAPLE LEGS UPON EXITING

In one embodiment, the wire bending (e.g., curling) or staple forming surfaces, such as arbors, may be fixed and disposed on an inner wall or surface of a staple cartridge pocket or opening (i.e., part of the staple cartridge body). The arbors may be positioned at or near the exit of the cartridge pocket (also referred to as a staple pocket, staple channel, or staple cavity) such that the staple legs of a staple are curled by the arbors as the staple legs exit the staple pocket. In an embodiment, there are at least two arbors or staple forming surfaces located at the exit of the staple pocket for each staple leg, such that one staple forming surface is on each side of the staple leg being bent. As mentioned above, the staple forming surfaces may be fixed during the formation of the staple (i.e., during the curling of the staple legs as the staple legs exit the staple pocket of the staple cartridge body).

In some embodiments, one or more of the arbors or staple forming surfaces may be movable, releasable or detachable. For example, the arbors or staple forming surfaces may be released with the fully curled staple legs after the staple forming is complete. In this case, the arbors may be made out of a bioabsorbable material. In another example, the staple cartridge may contain a mechanism or device that retracts the arbors. In other words, the arbors may be moved out of the way to allow the staples to deploy or exit the cartridge pocket. In yet another example, the arbors or staple forming surfaces may be designed to allow the staple crown to pass through the arbors or staple forming surfaces. Thus, the staple cartridges described here may use arbors or staple forming surfaces of the types described in U.S. patent application Ser. No. 18/781,578, entitled "Deployable Arbor Sets That Break Away From Staple Cartridge," and U.S. patent application Ser. No. 18/781,583, entitled "Multi-Part Staple With Separate Legs And Crown To Facilitate Staple Release From Arbors," the disclosures of which are incorporated by reference herein, in their entirety.

In one embodiment, the staple forming surfaces or arbors may be simple round pins placed at the exit of a staple cartridge pocket. These pins may be wires, posts, pins, and the like with a diameter of up to one and a half times (1.5×) the diameter of the staple wire. This size constraint is practical in space between jaws of a surgical stapler, either linear, laparoscopic, circular, or curved, so that there is an appropriate gap between opposing jaws of a surgical stapler. In another embodiment, the staple forming surfaces may be a protrusion on an inner surface or wall of the staple pocket, such as a rounded surface protrusion, as described below.

The staple shape and leg angle moving through and against the arbors controls the bending radius of the staple legs as they are advanced past or through the arbors. As the staple is raised and the crown approaches the arbors, the staple leg curl radius can change and tighten so that it gathers and then compresses tissue after the tips of the staple legs reach the top plate (opposite jaw), which has no pocket features, as mentioned above. The curvature of the staple wire may be set based on expected tissue thickness to be captured between opposing jaws. The staple wire curvature may also be set to fully cover the tissue gap to the opposing jaw so that all of the tissue is captured and fastened by the formed staple.

The arbors or staple forming surfaces described herein may be used with many different types of staples, including staples where the staple legs extend upwardly from the staple crown in a substantially straight and parallel manner, staples where the staple legs include different segments of varying length and angles at which those segments extend away from each other, as well as staples having angles in two planes.

The disclosed arbors or staple forming surfaces thus allow for the forming of staples without the need for a staple forming pocket on an anvil jaw opposite the cartridge jaw (i.e., the jaw containing or holding the staple cartridge).

Figure 24:
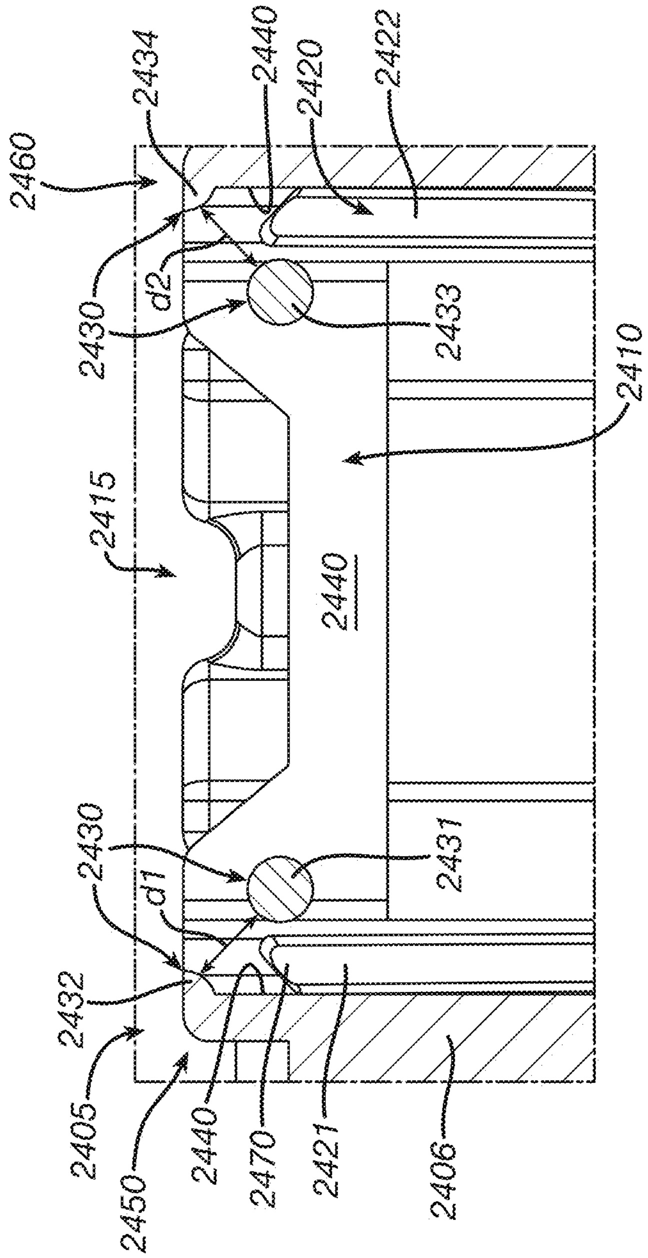
FIG. 24 depicts a cross sectional side view of a staple cartridge with staple forming features according to one embodiment.
Figure 25:
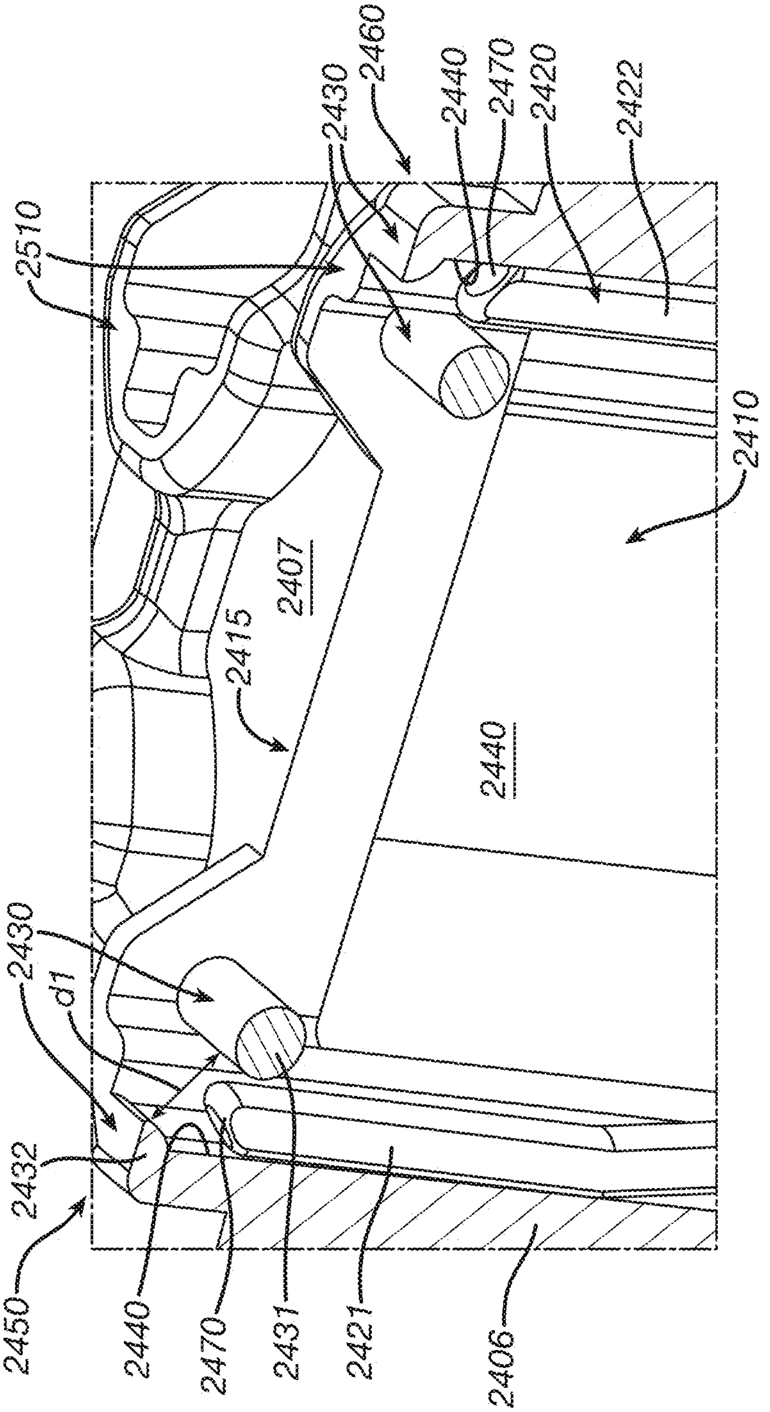
FIG. 25 depicts a cross sectional perspective view of the staple cartridge of FIG. 24 with staple forming features according to one embodiment.

FIGS. 24 and 25 depict cross sectional side and perspective views, respectively, of a staple cartridge with staple forming features according to one embodiment. The staple cartridge 2405 shown in FIGS. 24 and 25 and described below may be similar to the staple cartridge 37 described in section I above. For example, the staple cartridge 2405 of FIGS. 24 and 25 may be used with an end effector of a surgical instrument, such as end effector 12 of surgical instrument 10 described above. For instance, the end effector of the surgical instrument may be a surgical stapler having a first jaw and a second jaw, where one of the first jaw and second jaw are pivotable relative to the other, where the second jaw contains the staple cartridge 2405 described herein. The staple cartridge 2405 has a cartridge body 2406 and includes a staple pocket 2410 having an aperture or opening 2415 in a top surface or deck of the cartridge body 2406 of the staple cartridge 2405, and the staple pocket 2410 may contain an unformed staple 2420.

Similar to that described above with respect to FIG. 3, the staple cartridge 2405 may also contain a wedge sled and a plurality of staple drivers that are captured between the staple cartridge 2405 and a tray, with the wedge sled being located proximal to the staple drivers. The wedge sled is movable longitudinally within staple cartridge 2405; while staple drivers are movable vertically within staple cartridge 2405. The unformed staples 2420 are positioned within the staple pocket 2410 above corresponding staple drivers. Each unformed staple 2420 is driven vertically within the staple pocket 2410 by a staple driver to drive the unformed staples 2420 out through an associated opening 2415. In one example, the wedge sled presents inclined cam surfaces that urge staple drivers upwardly as the wedge sled is driven distally through the staple cartridge 2405.

As shown in FIGS. 24 and 25, the staple cartridge 2405 also includes two or more guide surfaces 2430 disposed adjacent the opening 2415 within the staple pocket 2410. As will be described in more detail below, some guide surfaces 2430 may be disposed directly adjacent the opening 2415 (i.e., right at the opening 2415) while other guide surfaces 2430 may be close to the opening 2415, but a short distance away from the opening 2415. In other embodiments, the guide surfaces 2430 may be positioned further away from the opening 2415 within the staple pocket 2410. The guide surfaces 2430 are configured to deform (e.g., plastically deform, bend or curl) the unformed staple 2420 as the unformed staple 2420 exits the staple pocket 2410 at the opening 2415. More specifically, the guide surfaces 2430 are configured to deform a staple leg 2421 of the unformed staple 2420 as the staple leg 2421 exits the staple pocket 2410 at the opening 2415.

In one example, the guide surfaces 2430 (also referred to herein as bending surfaces, guide features, staple forming features, or arbors) may be integrally formed with the staple cartridge 2405 (i.e., the cartridge body 2406 of the staple cartridge 2405). Specifically, the guide surfaces 2430 may be integrally formed with a sidewall 2440 of the staple pocket 2410 of the staple cartridge 2405. For instance, the staple pocket 2410 may be rectangular in shape and defined by four sidewalls 2440, including two opposing lengthwise sidewalls 2440 and two opposing shorter widthwise sidewalls 2440. In one embodiment, the guide surfaces 2430 may be a part of, and extend away from, one or both of the two opposing lengthwise sidewalls 2440. In an example, a guide surface 2430 may extend between the two opposing lengthwise sidewalls 2440. In another embodiment, the guide surfaces 2430 may be a part of, and extend outward from, one or both of the two opposing shorter widthwise sidewalls 2440. In some embodiments, such as those shown in FIGS. 24 and 25, the guide surfaces 2430 may be a part of, and extend outward from, one or both of the two opposing lengthwise sidewalls 2440 and the two opposing shorter widthwise sidewalls 2440.

In one embodiment, the guide surfaces 2430 are arbors, which, as mentioned above, are simple round or cylindrical rods, pegs, pins, deflection protrusions, and the like (or portions thereof). In some examples, the arbors 2430 may have a diameter of up to one and a half times (1.5×) the diameter of the wire of the unformed staple 2420. Other sizes are possible. The arbors 2430 may be placed at or near the exit of the staple pocket 2410, around which a staple leg wire is curled, bent, formed or shaped.

In one example, as shown in at least FIGS. 24-30, each side or end of the staple pocket 2410 includes two arbors 2430, such that there are four arbors 2430 total in the staple pocket 2410.

Referring to FIGS. 24 and 25, the staple cartridge 2405 includes a first top arbor 2432 disposed adjacent the opening 2415 at a first end 2450 of the staple pocket 2410 and a second top arbor 2434 disposed adjacent the opening 2415 at a second end 2460 of the staple pocket 2410. The first and second top arbors 2432, 2434 may be a type of surface protrusion that extends outward from respective sidewalls 2440 (e.g., two opposing shorter widthwise sidewalls 2440) where the sidewalls 2440 intersect the top surface of the staple pocket 2410 at the opening 2415. In the example shown in FIGS. 24 and 25, the first and second top arbors 2432, 2434 are quarter sections of a cylindrical pin or peg, similar to quarter round molding, at the uppermost portion of the sidewalls 2440 (i.e., the top surface of the opening 2415 at the sidewalls 2440). The first and second top arbors 2432, 2434 may span the entire width of the two opposing shorter widthwise sidewalls 2440, or may span only portions thereof. As described below in more detail, the first and second top arbors 2432, 2434 are designed and configured to deflect the legs of the unformed staple 2420 as the legs exit the staple pocket 2410.

The staple cartridge 2405 also includes a first bottom arbor 2431 offset a first distance d1 from the first top arbor 2432 and a second bottom arbor 2433 offset a second distance d2 from the second top arbor 2434. The first and second bottom arbors 2431, 2433 are cylindrical pins or pegs that extend outward from, or between, opposing lengthwise sidewalls 2440 of the staple pocket 2410. In one example, the first and second bottom arbors 2431, 2433 may span the entire distance or opening between the opposing lengthwise sidewalls 2440. In another example, the first and second bottom arbors 2431, 2433 may span only a portion of the distance or opening between the opposing lengthwise sidewalls 2440. In yet another example, each lengthwise sidewall 2440 of the two opposing lengthwise sidewalls 2440 may include a first and second bottom arbor 2431, 2433 that spans only a portion of the distance or opening between the opposing lengthwise sidewalls 2440. An example of this configuration is described below with reference to FIGS. 28A-C.

The first distance d1 (between the first top arbor 2432 and the first bottom arbor 2431) and the second distance d2 (between the second top arbor 2434 and the second bottom arbor 2433) may be vectors made up of an x-axis component and a y-axis component, i.e., a horizontal and vertical component. In this way, a value of the first and second distances d1, d2 may not change even though their respective individual components may change. In other words, the first bottom arbor 2431 may change position relative to the first top arbor 2432 while still maintaining the first distance d1. Similarly, the second bottom arbor 2433 may change position relative to the second top arbor 2434 while still maintaining the second distance d2. The arbors 2430 can be positioned in the staple cartridge 2405 to effectuate proper staple formation. Positioning of the arbors 2430 relative to each other has an impact on the staple formation. In some cases, even the slightest change of position of one of the arbors 2430 may have a significant impact on the staple formation. For example, the horizontal and vertical (i.e., x and y) positions of the arbors 2430 are important in determining staple trajectory, and even a small amount of movement in arbor 2430 positions can make a significant difference in trajectory. In other words, the positioning and distances between arbors 2430 can affect the amount/level of curl or curl radius (i.e., radius of curvature of staple legs as the staple legs are driven out of the staple pocket 2410) and curl height (i.e., height of the staple legs as the staple legs are driven out of the staple pocket 2410).

Referring back to FIGS. 24 and 25, the staple pocket 2410 may contain an unformed staple 2420 having a first staple leg 2421 and a second staple leg 2422. The first and second staple legs 2421, 2422 may be disposed along or may abut the two opposing shorter widthwise sidewalls 2440. As mentioned above, the first and second top arbors 2432, 2434 are designed and configured to deflect the legs of the unformed staple 2420 as the legs exit the staple pocket 2410 during a firing of the staple cartridge 2405. Specifically, the first top arbor 2432 and the first bottom arbor 2431 are configured to deform the first staple leg 2421 as the first staple leg 2421 exits the staple pocket 2410 at the opening 2415 during the firing, and the second top arbor 2434 and the second bottom arbor 2433 are configured to deform the second staple leg 2422 as the second staple leg 2422 exits the staple pocket 2410 at the opening 2415 during the firing. Each of the first staple leg 2421 and second staple leg 2422 have an angled tip 2470. As the unformed staple 2420 exits the staple pocket 2410, the first staple leg 2421 is configured to pass between the first top arbor 2432 and the first bottom arbor 2431, such that the angled tip 2470 of the first staple leg 2421 contacts the first top arbor 2432 causing the first staple leg 2421 to curl toward and over the first bottom arbor 2431. Similarly, the second staple leg 2422 is configured to pass between the second top arbor 2434 and the second bottom arbor 2433, such that the angled tip 2470 of the second staple leg 2422 contacts the second top arbor 2434 causing the second staple leg 2422 to curl toward and over the second bottom arbor 2433.

Figure 26:
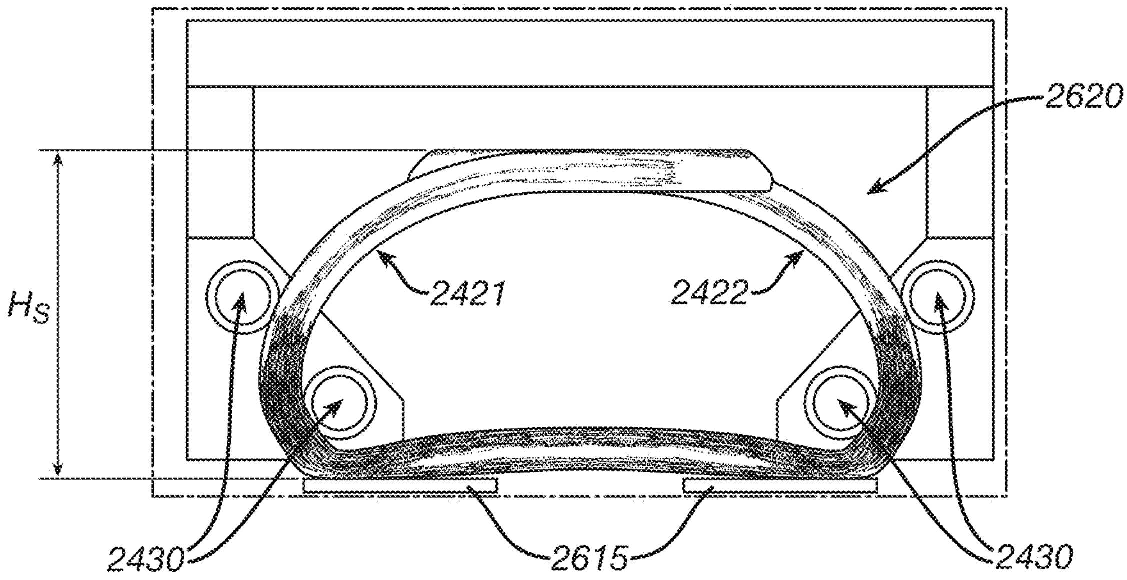
FIG. 26 depicts staple formation using arbors according to one embodiment.

FIG. 26 depicts staple formation using arbors according to one embodiment. The positioning and arrangement of the arbors 2430 of FIG. 26 is the same as that described above for FIGS. 24 and 25, i.e., two arbors (upper and lower) on each side of a staple pocket corresponding to first and second staple legs 2421, 2422, respectively. As shown in FIG. 26, during a firing of the staple cartridge 2405, a wedge sled is advanced through the staple cartridge 2405 and the wedge sled urges a staple driver 2615 upwardly, which drives the staples up and out of the staple pocket 2410. During this process, as the first and second staple legs 2421, 2422 are forced between the arbors 2430, the first staple leg 2421 and the second staple leg 2422 are deformed such that the first staple leg 2421 and the second staple leg 2422 curl toward each other to form a formed staple 2620 having a formed staple height $H_S$. The hatched portions of the staple legs 2421, 2422 in FIG. 26 indicate where the staple legs 2421, 2422 experience deformation forces.

As mentioned above, arbor locations can greatly affect the final shape of the formed staple 2620. The shape of the formed staple 2620 may depend on a tissue thickness that is being stapled (i.e., the tissue gap desired to span) and the amount of tissue to be grabbed by the formed staple 2620. The distances between the arbors 2430 is another variable to manipulate when controlling the final shape of the formed staple 2620, since distances between respective top and bottom arbors affect the degree of curvature and height of the staple curl, i.e., curl radius and curl height. For instance, in one example, when the first distance d1 and the second distance d2 are equal, a curl radius and curl height of the first staple leg 2421 is equal to a curl radius and curl height of the second staple leg 2422, respectively. This results in a substantially uniform or symmetrical formed staple 2620, such as that shown in FIG. 26. In another example, when the first distance d1 and the second distance d2 are different, a curl radius and curl height of the first staple leg 2421 is different than a curl radius and curl height of the second staple leg 2422, respectively. This results in one side of a formed staple having a tighter radius than the other side of the formed staple. In this way, the position and dimensions of arbors 2430 can be used to achieve different curl radii on different legs of the same staple, where one staple leg is deformed to have a looser radius while the other staple leg is deformed to have a tighter radius, as described in U.S. Pat. No. 12,004,744, entitled "Staple And Staple-Forming Pocket Arrangements For Surgical Staplers," filed on Sep. 27, 2021. One advantage of having differing staple curl radii of formed staples, particularly when these staples are perpendicular to a cut line, is to balance hemostasis and perfusion.

In addition to arbor 2430 positions and dimensions, staple leg geometry may also be manipulated to control the desired outcome of formed staples 2620. Specifically, changing staple leg geometries from straight to angled can change the curl on either staple leg independently. For example, staples with asymmetrical staple legs may be used, where one staple leg has a straight segment that moves through the arbors 2430 without bending while the other staple leg interfaces with the arbors 2430 the entire time it exits the staple pocket 2410. This may be desirable depending on the amount of tissue gap needed to reach across and grasp tissue. For example, with thicker tissue, if the staple legs started to curl at a tight radius immediately upon exiting the staple pocket, the height of the formed staple would not be very high, thus resulting in very little tissue being grasped by the formed staple. In another example, with thinner tissue, if the staple legs exited out of the staple pocket with a looser radius, the height of the formed staple would be larger and may be too loose to properly compress the tissue making the formed staple ineffective.

In one embodiment, staples having variable or selective leg segments may be used. For instance, a staple may have staple legs with a first or angled segment in which the staple leg extends outward/upward from the crown at an angle and a second or vertical or straight segment in which the staple leg is vertical (e.g., vertical/straight between the angled portion and the tip of the staple leg). The length of the second or vertical segment may determine how far the staple leg advances through the arbors before reaching the angled segment, which may initiate the bending (staple curling). In this way, there is a relationship between the length of the vertical segment and the tissue gap desired to span, in which the longer the vertical segment, the larger the tissue gap to span can be in order to capture thicker tissue. The angled segment may determine how much bend or curl is put into the staple leg as it lifts into the arbors. The bend or curl radius and arbor position can determine the final curl radius. A more aggressive (i.e., higher) angle of the angled segment may increase the force needed to bend or curl the staple leg, resulting in a tighter formed curl radius and therefore a tighter formed staple. In this way, the staple leg angle relative to the arbors can change the curl radius, especially as the crown of the staple approaches the arbors. Manipulating the staples and arbors in this way makes it possible to form a staple tighter than the gap between opposing jaws of a surgical stapler (i.e., the height of the formed staple is less than a distance between opposing jaws of the surgical stapler).

Another example of a staple having variable or selective leg segments is shown in FIG. 19. In this example, the staple 1625 includes three segments: a first vertical segment extending upward from the crown of the staple 1625; an angled segment extending upward and outward from the first vertical segment; and a second vertical segment extending upward from the angled segment to the tip of the staple 1625. In this example, changing the lengths of the vertical segments and the angle of the angled segment changes the final shape of the formed staple, and manipulating these variables will be based on the desired tissue gap the formed staple needs to reach across in order to grasp an appropriate amount of tissue.

In some cases, it may be desirable and advantageous to have formed staples with the same or uniform height. In other cases, it may be desirable and advantageous to have formed staples with differing heights. One way to achieve formed staples with differing heights using conventional anvils is to simply vary the distance that staple drivers are driven upward in the staple cartridge. In this case, the further the drivers are driven upwards toward the anvil, the more formed the staples become, thus having a smaller height, whereas the less the drivers are driven, the staples are less formed and have a larger height. However, in the present disclosure staples may be formed without the staples contacting an anvil jaw. Therefore, other means of achieving different formed staple heights are needed. In addition to manipulating the variables discussed above, loading a staple cartridge with unformed staples of varying heights may also help achieve the desired outcome of formed staples with varying heights. By changing the positions and dimensions of arbors and by varying unformed staple heights in the staple cartridge, formed staples with varying heights may be achieved even in situations where the tissue thickness between opposing jaws of the stapler is the same across the length of the staple cartridge and in situations in which all of the staple drivers advance upward in the staple cartridge the same amount.

As noted above, the staple cartridge 2405 of FIGS. 24 and 25 may be used with an end effector of a surgical instrument, such as a surgical stapler. In one embodiment, the surgical stapler includes a first jaw and a second jaw pivotable relative to the first jaw, the second jaw containing a staple cartridge, such as the staple cartridge 2405 described above. In this example, the staple cartridge 2405 includes a proximal end, a distal end, and a tissue supporting deck 2407. The staple cartridge 2405 also includes a plurality of rows of staple cavities 2410 defined in the deck 2407 and configured to hold unformed staples 2420. The staple cartridge 2405 further includes a staple forming feature 2430 disposed in the staple cavities 2410, a plurality of drivers 2615 configured to drive the unformed staples 2420 out of the staple cavities 2410 toward the first jaw, and a sled movable from the proximal end to the distal end of the staple cartridge 2405 during a firing stroke to lift the plurality of drivers 2615 toward the first jaw. The staple forming feature 2430 is configured to deform the unformed staples 2420 during the firing stroke to formed staples 2620 having a formed staple height $H_S$. See FIG. 26.

The staple forming feature 2430 disposed in the staple cavities 2410 may be the same as the guide surfaces and arbors discussed above. During the firing stroke, the unformed staples 2420 are deformed into the formed staples 2620 by the staple forming feature 2430 while avoiding contact with the first jaw.

In one example, the unformed staples 2420 in the plurality of rows of staple cavities 2410 have the same height. In another example, the unformed staples 2420 in at least one row of staple cavities 2410 of the plurality of rows of staple cavities 2410 have different heights.

As discussed above, formed staple heights may be uniform or varying. In one example, the formed staple height $H_S$ of the formed staples 2620 is less than a distance between the plurality of staple drivers 2615 and the first jaw at an end of the firing stroke. In another example, during the firing stroke, when a tissue thickness and a distance between the first jaw and the second jaw in which the unformed staples 2420 are formed is uniform across the plurality of rows of staple cavities 2410, and when the plurality of drivers 2615 are lifted no further than the deck 2407 of the staple cartridge 2405, the unformed staples 2420 in different rows of the plurality of rows of staple cavities 2410 are formed to different formed staple heights $H_S$. This provides the advantage of being able to control staple height formation by changing dimensions and positioning of the staple forming features 2430 and/or by providing varying heights of unformed staples 2420 in the staple cartridge 2405, as described above.

In one embodiment, a width of the formed staples 2620 is the same as a width of the unformed staples 2420.

Figure 27:
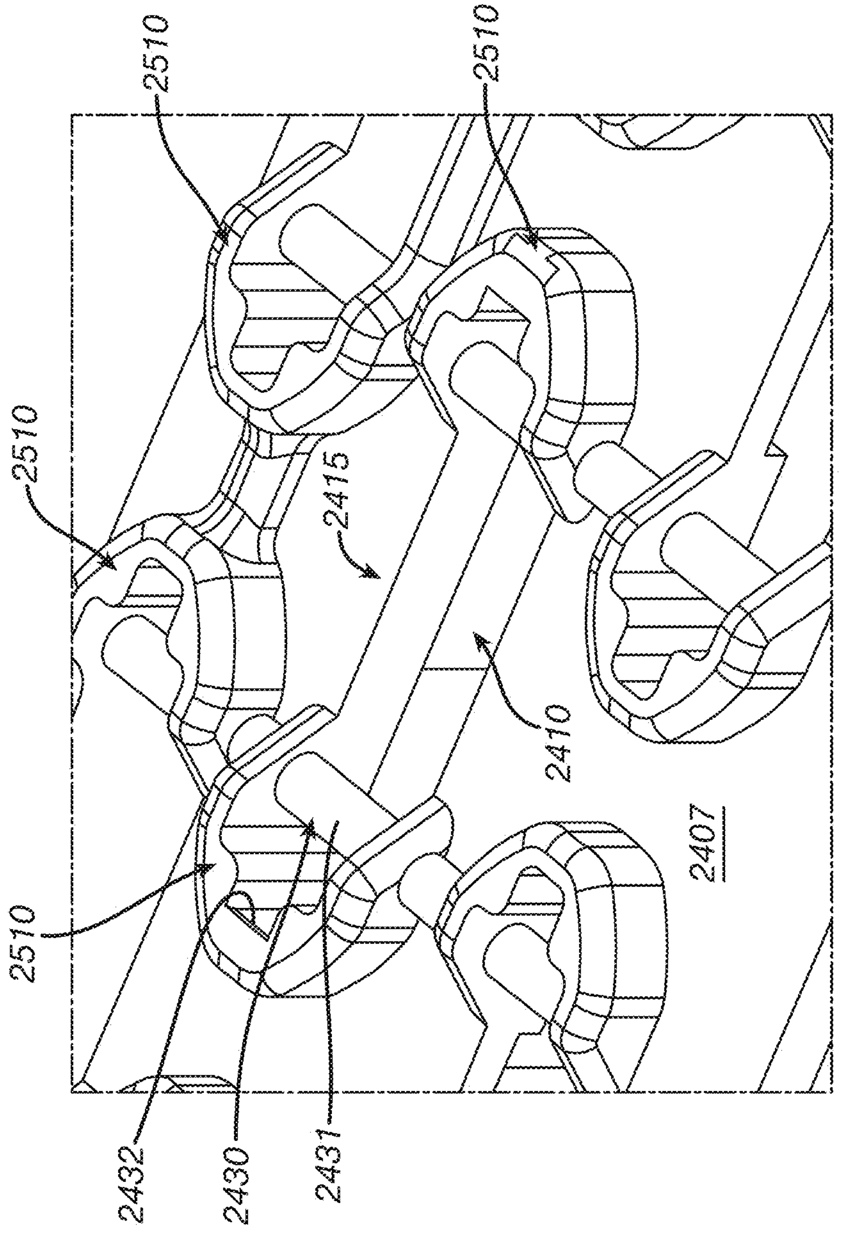
FIG. 27 depicts a perspective top view of the staple cartridge of FIGS. 24 and 25 according to one embodiment.

Referring back to the figures, FIG. 27 is perspective top view of the staple cartridge of FIGS. 24 and 25 according to one embodiment. In the example shown in FIG. 27, the guide surface 2430 includes a first arbor 2431 that spans across the opening 2415. In this case, the first arbor 2431 is a continuous arbor that spans multiple openings 2415. As shown in FIG. 27, the first arbor 2431 spans three openings 2415 of three staple pockets 2410. The staple cartridge 2405 of FIG. 27 also includes a second arbor 2432 disposed adjacent the opening 2415. The second arbor 2432 of FIG. 27 is the same as the first top arbor 2432 of FIGS. 24 and 25. As shown more clearly in FIG. 27 than in the cross sectional views of FIGS. 24 and 25, the span of the second arbor 2432 is shorter than the span of the first arbor 2431. In one example, the span of the second arbor 2432 corresponds to a size of a staple leg.

Similar to above, the first arbor 2431 and the second arbor 2432 are offset from one another vertically and horizontally within the staple pocket 2410. The second arbor 2432 is disposed at an end of the staple pocket 2410, while the first arbor is offset closer towards the center of the staple pocket 2410.

In the example shown in FIGS. 24, 25, and 27, the staple cartridge 2405 includes a tissue gripping feature 2510 disposed at the opening 2415 of the staple pocket 2410. The tissue gripping feature 2510, or gripping surface technologies, may be features disposed on the cartridge deck 2407 designed and configured to grip against tissue when tissue is grasped between opposing jaws of the surgical stapler. These features interact (i.e., contact, engage, etc.) with the tissue held against the cartridge deck 2407 to help prevent tissue movement during a firing stroke of the surgical stapler. As shown in FIGS. 24, 25, and 27, the guide surface 2430 (e.g., either the first or second arbor 2431, 2432) is disposed within the tissue gripping feature 2510. In this case, the first and second arbors 2431, 2432 are both located above a central portion of the opening 2415 of the staple pocket 2410, since the first and second arbors 2431, 2432 are both disposed in the tissue gripping feature 2510, which is disposed on the cartridge deck 2407. However, in another embodiment without a tissue gripping feature 2510, where the entire opening 2415 is on the same level as the cartridge deck 2407, the first and second arbors 2431, 2432 would both be located below the opening 2415 of the staple pocket 2410.

In either arrangement, the relative position and orientation of the arbors 2430 with respect to each other remain the same and thus provide the same staple curling functions as described above. Specifically, the staple leg 2421 is configured to exit the staple pocket 2410 between the first arbor 2431 and the second arbor 2432, such that the first arbor 2431 and the second arbor 2432 deform the staple leg 2421 as the staple leg 2421 exits the staple pocket 2410. This allows staple formation while avoiding contact with a distant anvil.

The staple forming features and functionality described herein must still allow the staples to release from the staple cartridge 2405. In one example, the arbors 2430 may be pushed out of their supports (such as the tissue gripping features 2510) by a driver at the top of the firing stroke and released with staples. Other examples include frangible arbors, deployable arbor sets, retractable arbor sets, or arbors having a slidable engagement with a driver to move and release the staple.

In one embodiment, a frangible or plastically deformable static arbor may be used to form the staple curl (e.g., to bend the staple during the firing stroke), but then allow the crown of the staple to pass the arbor when the driver completes the firing stroke. In this case, an interrupted, broken, or segmented arbor may be used to release the staple. The arbor positions and orientations relative to one another can remain the same as discussed above, except that one of the arbors (e.g., the longer arbor 2431 spanning the opening that lies in the path of the crown) has an opening or break in the center (e.g., halfway across the opening) to allow the crown to pass through the arbor 2431. The edges of the portions of the arbor 2431 defining the opening may be radiused edges to allow smooth movement of the staple along the surfaces of the arbors during curling. The wire of the staple will interface with the arbor, and cause curling, as discussed above. The features (e.g., arbors) may be integral with the cartridge, also as discussed above. The arbors being integral with the cartridge may allow to use molds, especially if the arbors are designed to be on an edge of feature that is already being molded. This would simply the manufacturing of the cartridges to contain arbors. An interrupted arbor has the advantage in that as the driver is raised within the staple cartridge to finish the staple firing, the staple crown can "pop" past or through the interruption or break in the arbor, meaning that with enough force, the crown is squeezed past or through the break or interruption. In some cases, the interrupted arbor may even deform (either plastically or elastically) enough to allow the staple crown to pass through, thereby releasing the staple.

Figure 28A:
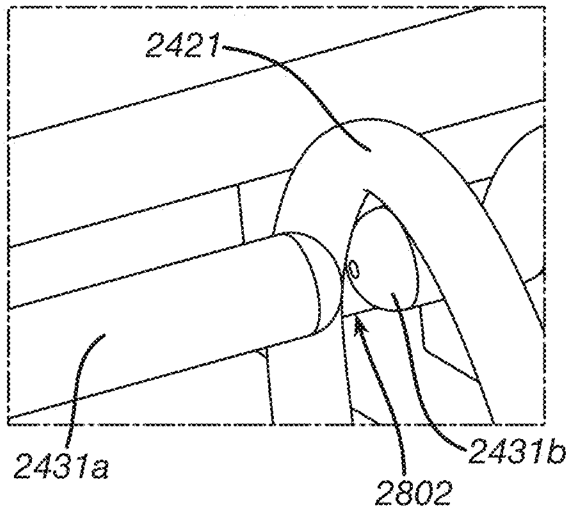
FIGS. 28A-C depict an interrupted arbor according to one embodiment.
Figure 28B:
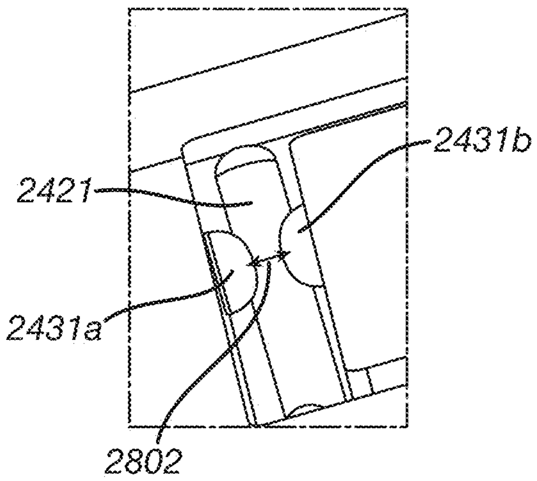
Figure 28C:
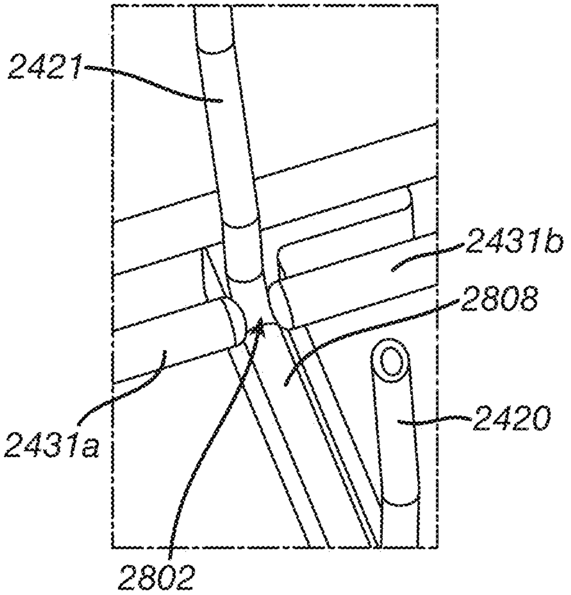

FIGS. 28A-C depict an interrupted arbor according to one embodiment. As shown in FIGS. 28A-C, the first arbor 2431 described above includes an interrupted arbor having a first portion 2431*a* and a second portion 2431*b* spaced apart from, and axially aligned with, the first portion 2431*a*. The first portion 2431*a* and second portion 2431*b* of the interrupted arbor are spaced apart by a gap 2802, or opening in the center to allow the crown 2808 of the staple (at this point in the formed state) to pass through (i.e., between the first portion 2431*a* and second portion 2431*b* of the interrupted arbor).

As shown in FIGS. 28A and 28B, the ends and edges of the first portion 2431*a* and second portion 2431*b* of the interrupted arbor are radiused or rounded. This still allows the staple leg 2421 to be curled against the radiused surfaces of the first portion 2431*a* and second portion 2431*b* of the interrupted arbor.

In one example, as shown in FIGS. 28B and 28C, a distance of the gap 2802 is less than a diameter of a crown 2808 of the unformed staple 2420.

As shown in FIG. 28C, when the driver reaches the top of the firing stroke, the crown 2808 of the staple is able to pass through (i.e., between) the first portion 2431*a* and second portion 2431*b* of the interrupted arbor. The force of the driver in the upward direction causes the crown 2808 to either squeeze through the gap 2802 or deform (plastically or elastically) the first portion 2431*a* and second portion 2431*b* of the interrupted arbor to deflect enough to allow the crown 2808 to pass through.

Figure 29A:
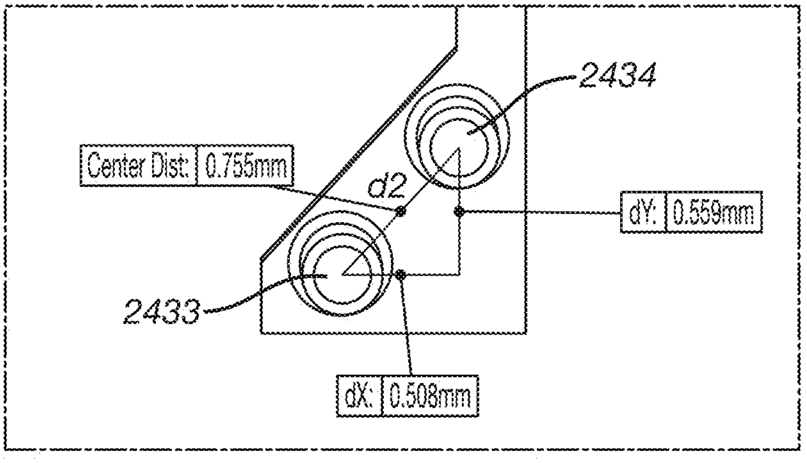
FIGS. 29A and 29B depict an arrangement of arbors according to one embodiment.
Figure 29B:
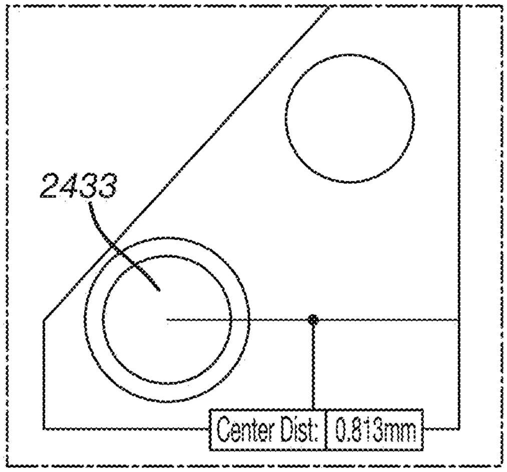

FIGS. 29A and 29B depict an arrangement of arbors according to one embodiment. As shown in FIG. 29A, the position of two arbors relative to each other, such as the second bottom arbor 2433 relative to the second top arbor 2434, is shown in more detail. Specifically, the x and y (horizontal and vertical) distances between the center of the arbors 2433, 2434 are shown. Also, the vector offset distance d2 is also shown. As shown in FIG. 29B, the position of a bottom arbor, such as the second bottom arbor 2433, relative to the sidewall of the staple pocket, such as one of the two opposing shorter widthwise sidewalls 2440 of staple pocket 2410, is shown in more detail. While FIGS. 29A and 29B illustrate specific measurements for one embodiment, other values of the dimensions shown may be used. For instance, the vector offset distance d2 between the center of the second bottom arbor 2433 and the center of the second top arbor 2434 may range between about 0.020 and 0.035 inch, in one example, and more specifically may be 0.030 inch in another example. Similarly, the x and y (horizontal and vertical) distances between the center of the arbors 2433, 2434 may range between about 0.015 and 0.025 inch, in one example, and more specifically between about 0.020 and 0.022 inch in another example. The distance between the center of the second bottom arbor 2433 and the sidewall 2440 of the staple pocket 2410, as shown in FIG. 29B, may range between about 0.015 and 0.020 inch, in one example, and more specifically about 0.019 inch in another example. The vertical distance between the center of the second bottom arbor 2433 and the top of the tissue gripping feature 2510 of the staple cartridge deck 2407 may be between 0 to 0.025 inch in one example, and more specifically about 0.014 to 0.022 inch in another example. The distances described above are representative when using a staple wire of about 0.009 inch diameter, and round arbors that are about 0.014 inch diameter. Because the relative positions of the arbors and the wire size cause the interference that bends the staple, these distances may be scaled proportional to different staple wire diameters to achieve similar effects for slightly smaller or larger staple wires, for example.

Figure 30:
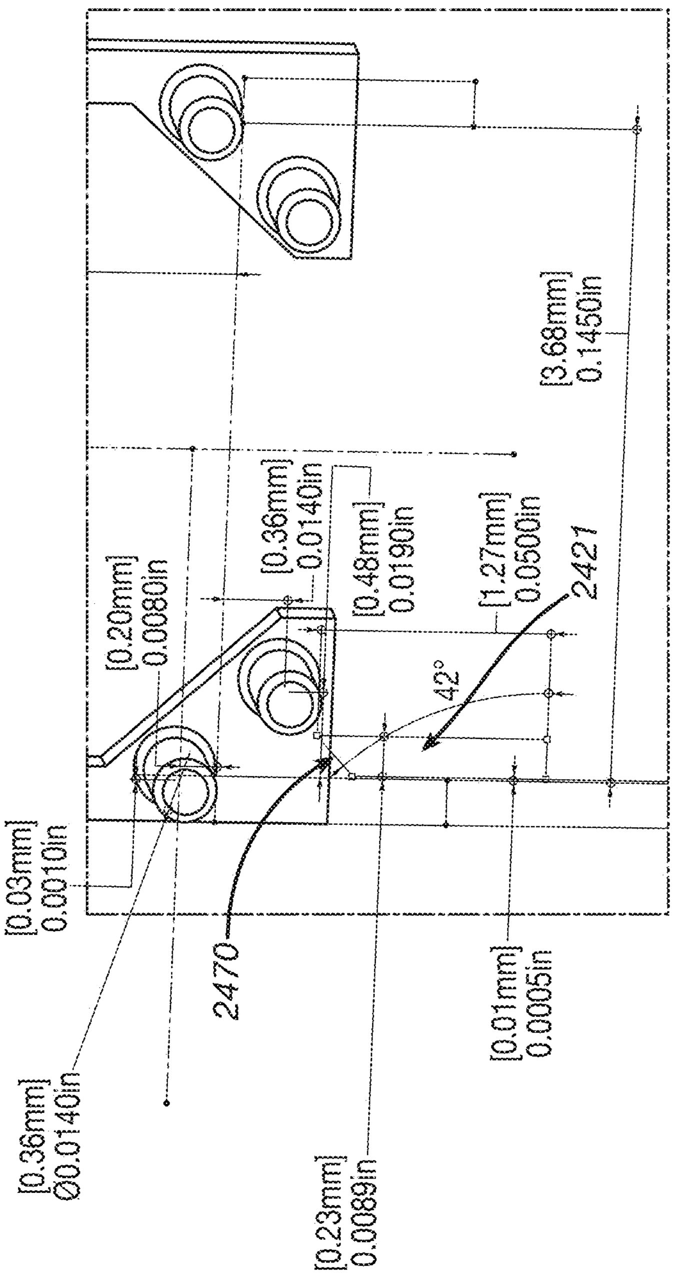
FIG. 30 depicts an arrangement of arbors according to one embodiment.

FIG. 30 depicts an arrangement of arbors according to one embodiment, where the arbors have a diameter of approximately 0.014 inch. FIG. 30 illustrates specific values for other measurements of an arbor arrangement, in one example. Included in FIG. 30 is the relative and/or specific positioning and dimensions of the first staple leg 2421 having the angled tip 2470 positioned below the arbors prior to firing.

IV. STAPLER DEVICE THAT FORMS STAPLES FROM VARIOUS CARTRIDGES HAVING DIFFERENT ROW PATTERNS

As was noted above, there is a current problem with having to match a staple pocket pattern of a staple cartridge with a staple forming pocket pattern of an anvil. Until now, a same or similar staple pattern of a staple cartridge of conventional technology requires the use of the same anvil (i.e., the anvil having the same anvil pocket configuration) and a different staple pattern requires the use of a different anvil (i.e., an anvil having a different anvil pocket configuration). For example, currently, a user (e.g., surgeon or robotic system) may need a first staple pattern for a first firing, such as a staple pattern having staples arranged in straight rows parallel to the cut line for a firing on vascular structures of a patient, but then require a different, second staple pattern for a second firing, such as a staple pattern having staples in rows that are angled and/or offset with respect to one another for a firing on a structure that needs additional elasticity, such as lung parenchyma of the patient. Conventionally, in this case, since the different staple patterns requires different anvils having different anvil pocket configurations, the user would need to swap out the end effector (e.g., stapler jaws) in order to use a different anvil for the different desired staple pattern of a different staple cartridge. In some cases, depending on how modular the surgical instrument is, the entire instrument may need to be swapped out with a different one. This leads to increased time, cost, and waste of the surgical procedure.

The proposed staple cartridges involve the self-contained staple forming features discussed above. These staple cartridges do not need to rely on anvils or upper jaws to form staples, as discussed in the sections above, and can form different types and patterns of staples depending on the arrangement, size, and configuration of the proposed staple forming features contained in the proposed staple cartridges. This means a user does not need to change anvils (or the entire end effector or surgical instrument) when different staples and/or staple patterns are needed. A user can simply swap out the staple cartridges, since it is the cartridges that form the staples.

The proposed staple cartridges allow for various types of staple cartridge reloads to be fired from the same surgical tool, eliminating the need for modularity and/or complex adapters. The proposed staple cartridges also eliminates the need for pocket alignment (i.e., alignment between staple pockets in the staple cartridge and staple forming pockets in the anvil). This allows for upper jaws of end effectors to be made and used more simply and to be re-used more often, thus reducing time, cost, and waste of surgical procedures.

Figure 31:
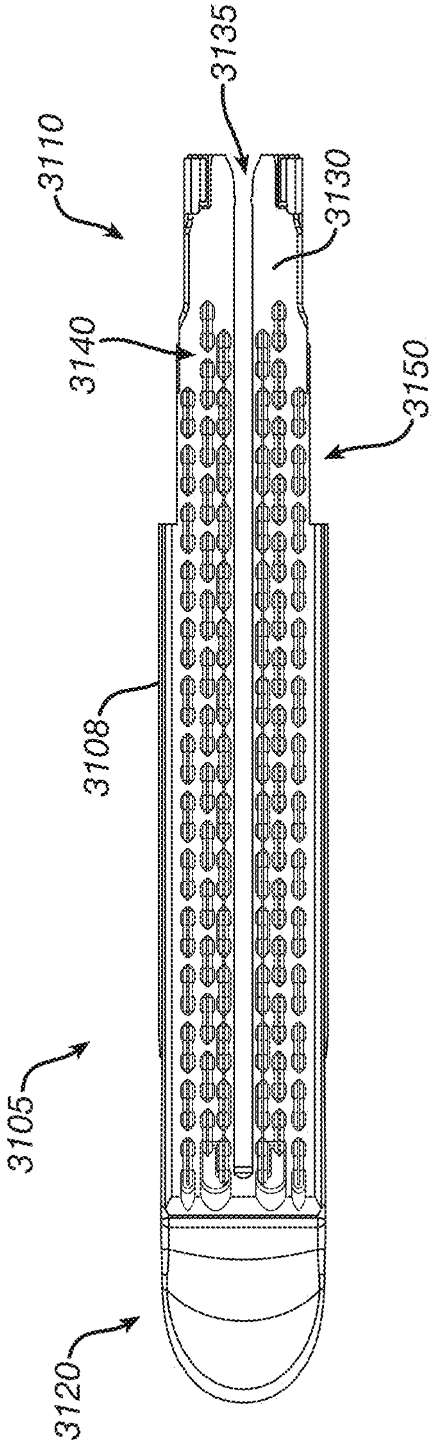
FIG. 31 depicts a plan view of a staple cartridge having a first staple pattern according to one embodiment.

FIG. 31 depicts a plan view of a staple cartridge having a first staple pattern according to one embodiment. The staple cartridge 3105 of FIG. 31 is configured to be used with an end effector, such as end effector 12 described above, having a cartridge jaw 16 and an anvil jaw 18 pivotably connected to the cartridge jaw 16 to clamp tissue, such that the end effector 12 is configurable in an unclamped configuration and a clamped configuration. The staple cartridge 3105 includes a body 3108 having a proximal end 3110 and a distal end 3120. The size and shape of the body 3108 of the staple cartridge 3105 is designed to be the same as the body 70 of a typical staple cartridge 37 described above (see FIGS. 3-6), such that the staple cartridge 3105 is capable of being inserted into and received by a channel of a cartridge jaw 16 of an end effector 12 for assembly therewith. In other words, the footprint (e.g., size and shape) of the staple cartridge 3105 is the same as the footprint of other typical staple cartridges. In this way the staple cartridge 3105 removably fits within a jaw of a surgical stapler.

In one example, the body 3108 of the staple cartridge 3105 also includes similar, if not identical, alignment features as the body 70 of a regular staple cartridge 37, as best shown when comparing FIG. 31 with FIGS. 3 and 6 described above. For instance, the body 3108 of the staple cartridge 3105 may include alignment features such as lugs, notches, and flanges. Similar to the regular staple cartridge 37, the alignment features of the staple cartridge 3105 facilitate the connection between the staple cartridge 3105 and the channel of a cartridge jaw 16 of an end effector 12. In this way, the staple cartridge 3105 installs and removes the same as other staple cartridges, such as the staple cartridge 37 described above in connection with FIGS. 3-6.

The staple cartridge 3105 also includes a tissue supporting deck 3130. As seen in FIG. 31, the staple cartridge 3105 includes a plurality of rows of staple pockets or cavities 3140 defined in the deck 3130. The staple cavities 3140 are configured to hold unformed staples. In the example shown in FIG. 31, the deck 3130 of the staple cartridge 3105 contains six total longitudinal rows of staple cavities 3140, with three rows being on one side of a knife slot/channel 3135 that runs longitudinally down the middle of the deck 3130 of the staple cartridge 3105 and three rows on the other side of the knife slot 3135. In the example shown in FIG. 31, each row of staple cavities 3140 contains either 14 or 15 staple cavities 3140. For instance, both outermost rows contain 14 staple cavities 3140 while the remaining rows contain 15 staple cavities 3140. In the example shown in FIG. 31, the staple cavities 3140 are aligned parallel to the knife slot 3135. Each of the rows of staple cavities 3140 are offset by a distance, such that alternating rows of staple cavities 3140 are not aligned laterally.

The unformed staples contained in the staple cavities 3140 are configured to be deformed, during a firing stroke, into formed staples by a staple forming feature in the staple cavities 3140 to form a first staple pattern 3150. The staple forming feature in the staple cavities 3140 may be the same features discussed in the sections above, such as guiding or deforming surfaces, such as arbors.

The first staple pattern 3150 defines characteristics of the staple cavities 3140, such as staple crown orientations within respective rows of staple pockets 3140, spacing of staple pockets 3140 within respective rows of staple pockets 3140, lateral spacing between respective rows of staple pockets 3140, a number of staple pockets 3140 within respective rows of staple pockets 3140, and the like. Other staple cavity 3140 characteristics may be defined by the first staple pattern 3150 as well.

The staple cartridge 3105 is configured to be insertable into a channel of a first jaw of an end effector for assembly therewith and to be fired during a firing stroke of the end effector to form the first staple pattern 3150 independently of a second jaw of the end effector. The staple forming feature is configured to bend or curl the unformed staples during the firing stroke. The staple forming feature bends or curls the unformed staples while avoiding contact with the second jaw.

Figure 32:
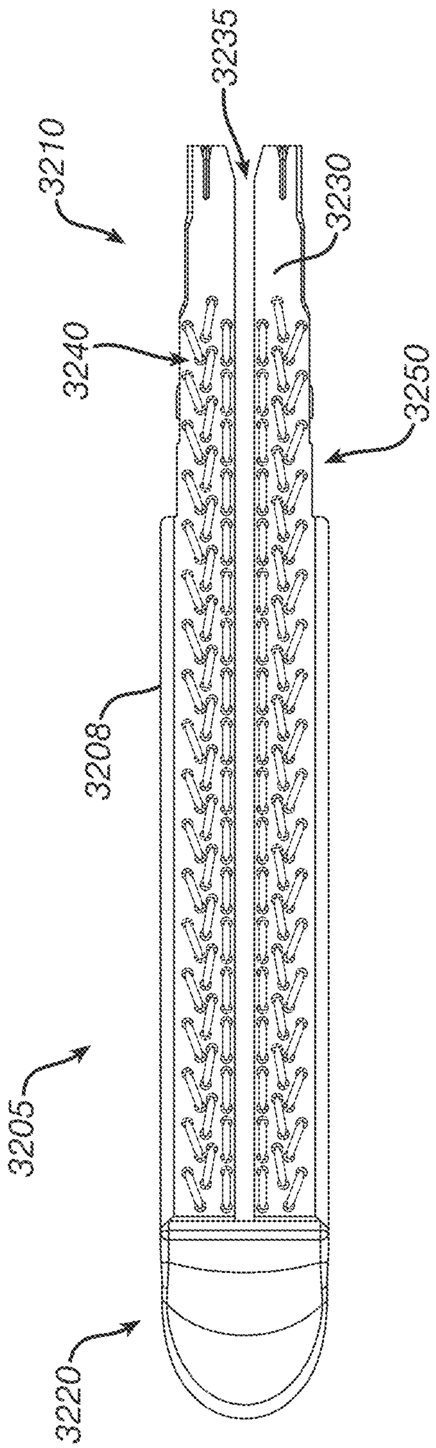
FIG. 32 depicts a plan view of another staple cartridge having a second staple pattern according to another embodiment.

FIG. 32 depicts a plan view of another staple cartridge having a second staple pattern according to another embodiment. The staple cartridge 3205 of FIG. 32 is generally the same as the staple cartridge 3105 of FIG. 31 described above, except for the pattern of staple pockets or cavities 3240, described below. Similar to the staple cartridge 3105 of FIG. 31, the staple cartridge 3205 of FIG. 32 is designed and configured to be interchangeable with other staple cartridges, such that a same stapler can use the staple cartridge 3205 of FIG. 32 as well as other staple cartridges, such as staple cartridge 3105 of FIG. 31.

The staple cartridge 3205 includes a body 3208 having a proximal end 3210 and a distal end 3220. The size and shape of the body 3208 of the staple cartridge 3205 is designed to be the same as the body 70 of a typical staple cartridge 37 described above (see FIGS. 3-6), such that the staple cartridge 3205 is capable of being inserted into and received by a channel of a cartridge jaw 16 of an end effector 12 for assembly therewith. In other words, the footprint (e.g., size and shape) of the staple cartridge 3205 is the same as the footprint of other typical staple cartridges. In this way the staple cartridge 3205 removably fits within a jaw of a surgical stapler.

The staple cartridge 3205 also includes a tissue supporting deck 3230. As seen in FIG. 32, the staple cartridge 3205 includes a plurality of rows of staple pockets or cavities 3240 defined in the deck 3230. The staple cavities 3240 are configured to hold unformed staples. In the example shown in FIG. 32, the deck 3230 of the staple cartridge 3205 contains six total longitudinal rows of staple cavities 3240, with three rows being on one side of a knife slot 3235 that runs longitudinally down the middle of the deck 3230 of the staple cartridge 3205 and three rows on the other side of the knife slot 3235. In the example shown in FIG. 32, each row of staple cavities 3240 contains 18 staple cavities 3240. In the example shown in FIG. 32, the staple cavities 3240 directly adjacent the knife slot 3235 are aligned parallel to the knife slot 3235, whereas the outermost two rows on each side of the knife slot 3235 are not parallel with the knife slot 3235 and are instead angled with respect to each other. The staples of any of the rows may be nested, meaning that the outer boundaries in a lateral dimension may overlap with an adjacent row. This allows staples of multiple angles to fit within the footprint of the cartridge body.

Similar to above, the unformed staples contained in the staple cavities 3240 are configured to be deformed, during a firing stroke, into formed staples by a staple forming feature in the staple cavities 3240 to form a second staple pattern 3250. The staple forming feature in the staple cavities 3240 may be the same features discussed in the sections above, such as guiding or deforming surfaces, such as arbors.

The second staple pattern 3250 defines characteristics of the staple cavities 3240, such as staple crown orientations within respective rows of staple pockets 3240, spacing of staple pockets 3240 within respective rows of staple pockets 3240, lateral spacing between respective rows of staple pockets 3240, a number of staple pockets 3240 within respective rows of staple pockets 3240, and the like. Other staple cavity 3240 characteristics may be defined by the first staple pattern 3250 as well.

The staple cartridge 3205 is configured to be insertable into a channel of a first jaw of an end effector for assembly therewith and to be fired during a firing stroke of the end effector to form the first staple pattern 3250 independently of a second jaw of the end effector. The staple forming feature is configured to bend or curl the unformed staples during the firing stroke. The staple forming feature bends or curls the unformed staples while avoiding contact with the second jaw.

Since neither of the staple cartridges 3105, 3205 of FIGS. 31 and 32 above need an anvil jaw to form the staples contained therein, both staple cartridges 3105, 3205 of FIGS. 31 and 32 can be used by the same stapler. In other words, both staple cartridges 3105, 3205 of FIGS. 31 and 32 can be part of the same interchangeable stapling system.

For example, in one embodiment, a surgical stapling system includes a stapler including a first jaw having a tissue clamping surface and a second jaw pivotable relative to the first jaw, the second jaw operable to receive interchangeable staple cartridges having different staple patterns. The surgical stapling system includes a first staple cartridge 3105 having a first staple pattern 3150 and a second staple cartridge 3205 having a second staple pattern 3250, the second staple pattern 3250 being different from the first staple pattern 3150. The stapler is configured to perform a first firing stroke to form a first set of staples using the first staple cartridge 3105 and a second firing stroke to form a second set of staples using the second staple cartridge 3205. The first staple pattern 3150 and the second staple pattern 3250 includes rows of staple pockets 3140, 3240 configured to receive staples.

The stapler can perform these firing strokes using different cartridges 3105, 3205 without having to change end effectors or portions thereof, such as the anvil jaw. This is a significant improvement over conventional stapling systems since conventionally, in order to use a different staple cartridge having a different staple pattern, a different anvil jaw is typically required in order to have an anvil jaw with staple forming anvil pockets that match the staple cartridge pockets on the cartridge.

In this case, the first set of staples are formed by the first staple cartridge 3105 independently of the first jaw, and the second set of staples are formed by the second staple cartridge 3205 independently of the first jaw. In this example, the first set of staples and the second set of staples are formed by staple forming features contained in staple pockets 3140, 3240 of the first staple cartridge 3105 and the second staple cartridge 3205, respectively. Therefore, this allows forming different staple patterns in tissue using the same anvil jaw. In other words, a user is able to fire a stapler using the same anvil for both cartridges.

In one embodiment, the tissue clamping surface of the first jaw may be flat or pocketless, and serves the function to compress and hold tissue against the surface of the other jaw containing the cartridge, so that the tissue thickness to be captured by staples is established. In another embodiment, the tissue clamping surface of the first jaw may include one or more longitudinal grooves along a length of the tissue clamping surface. The one or more longitudinal grooves may accommodate the rows of staple pockets of both the first and second staple patterns 3150, 3250 of the first and second staple cartridges 3105, 3205. In one example, the one or more longitudinal grooves may be a single continuous groove, or trough, running longitudinally along the center of the tissue clamping surface of the first jaw between proximal and distal ends of the first jaw. In another example, the one or more longitudinal grooves may include two continuous grooves running longitudinally down the tissue clamping surface of the first jaw between proximal and distal ends. In this case, one longitudinal groove may be disposed on one side of the tissue clamping surface and the other longitudinal groove may be disposed on the other side of the tissue clamping surface. In one example, the troughs or grooves may simply accommodate tissue. In another example, the troughs or grooves may provide a clearance space, such that staples that are forming may curl into the clearance space, without contacting the surface of the first jaw (e.g., the surface of the trough or groove of the tissue contacting surface of the first jaw). In this way, the curling of the staples do not require the first jaw to form (e.g., bend or curl) and interference form the first jaw may be avoided. The first jaw, whether being flat or containing one or more longitudinal grooves, may still compress the tissue between the first and second jaws during a stapling procedure.

For example, during the first firing stroke and the second firing stroke, the staples in the rows of staple pockets 3140, 3240 of the first staple pattern 3150 and the second staple pattern 3250 avoid contact with the one or more longitudinal grooves.

Certain staple pocket 3140, 3240 characteristics may be controlled by the first or second staple pattern 3150, 3250. For example, the first staple pattern 3150 and the second staple pattern 3250 may define staple crown orientations within respective rows of staple pockets 3140, 3240. In another example, the first staple pattern 3150 and the second staple pattern 3250 may define spacing of staple pockets 3140, 3240 within respective rows of staple pockets 3140, 3240. In another example, the first staple pattern 3150 and the second staple pattern 3250 may define lateral spacing between respective rows of staple pockets 3140, 3240.

In yet another example, the first staple pattern 3150 and the second staple pattern 3250 may define a number of staple pockets 3140, 3240 within respective rows of staple pockets 3140, 3240.

Figure 33:
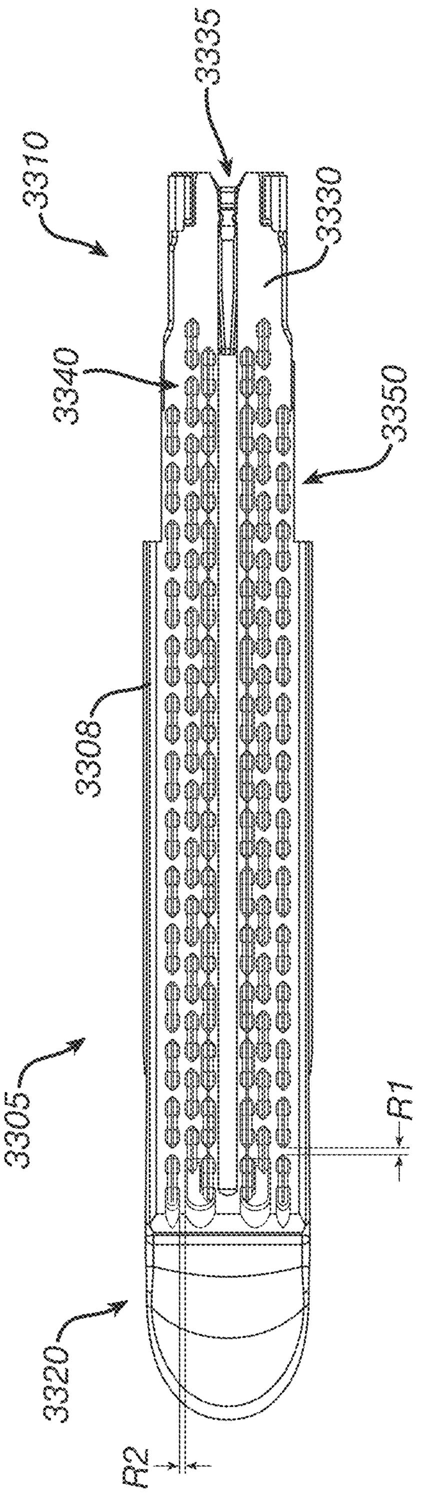
FIG. 33 depicts a plan view of another staple cartridge having a third staple pattern according to another embodiment.

FIG. 33 depicts a plan view of another staple cartridge having a third staple pattern according to another embodiment. The staple cartridge 3305 of FIG. 33 is generally the same as the staple cartridges 3105 and 3205 of FIGS. 31 and 32, so a detailed description has been omitted. Like reference numerals refer to like features. The only difference between the staple cartridge 3305 of FIG. 33 and the staple cartridge 3105 of FIG. 31 is that the staple forming features contained in the staple pockets 3340 allow for formed staple legs that are offset a certain distance from each other. For example, forming features in certain rows may bend or curl staples into a planar "B" shape, where other rows may be formed into a 3-D shape to capture a wider amount of tissue. The features may be varied across the rows, or within a given row. In these examples, the spacing of staple pockets may vary, either within a row as shown with R1, or among adjacent rows as shown with R2, as the alignment with pockets on an anvil jaw are no longer needed. In other words, the surfaces of the staple forming features may be angled relative to the staple crown, which moves the staple legs away from each other during staple formation.

Figure 34:
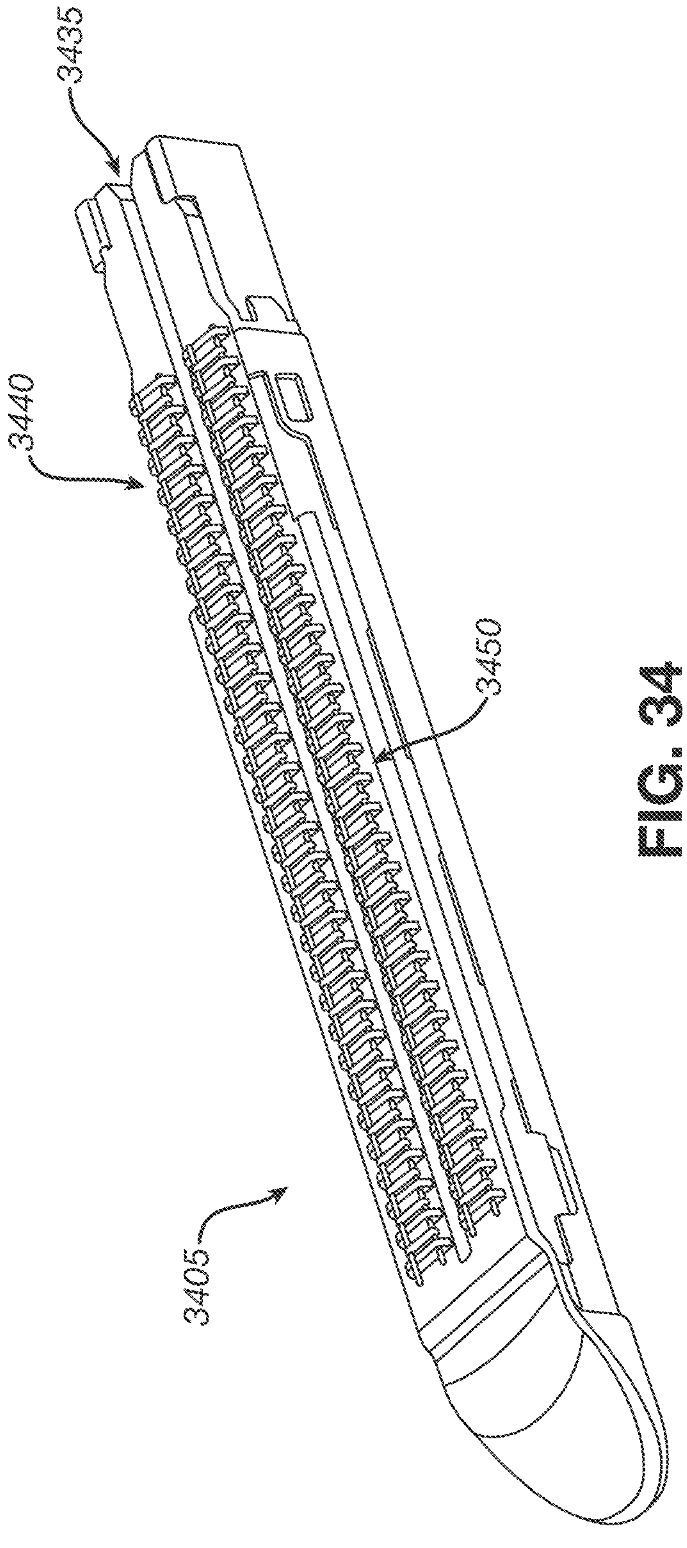
FIG. 34 depicts a perspective view of another staple cartridge having a fourth staple pattern according to another embodiment.

FIG. 34 depicts a perspective view of another staple cartridge having a fourth staple pattern according to another embodiment. The staple cartridge 3405 of FIG. 34 is generally the same as the staple cartridges 3105, 3205, and 3305 of FIGS. 31-33, so a detailed description has been omitted. Like reference numerals refer to like features. The difference of the staple cartridge 3405 of FIG. 34 is the arrangement and number of rows of staple cavities 3440 that make up the fourth staple pattern 3450. For example, the staple cartridge 3405 of FIG. 34 contains two rows of staple cavities 3440, each row being on a different side of the knife slot 3435. In the example shown in FIG. 34, the staple cavities 3440 are arranged parallel to each other and perpendicular to the knife slot 3435.

In one embodiment, a method of using a stapler having a first jaw with a tissue clamping surface and a second jaw pivotable relative to the first jaw, the second jaw operable to receive interchangeable staple cartridges having different staple patterns, includes inserting a first staple cartridge 3105 into the stapler, the first staple cartridge having a first staple pattern 3150. The method includes firing the stapler to form a first set of staples using the first staple cartridge 3105, and removing the first staple cartridge 3105 from the stapler. The method further includes inserting a second staple cartridge 3205 into the stapler, the second staple cartridge 3205 having a second staple pattern 3250 different from the first staple pattern 3150. The method also includes firing the stapler to form a second set of staples using the second staple cartridge 3205. In this case, the first set of staples are formed by the first staple cartridge 3105 independently of the first jaw, and the second set of staples are formed by the second staple cartridge 3205 independently of the first jaw. As noted above, allowing a user to fire two different staple cartridges using the same stapler provides many advantages, including reducing time, cost, and waste of surgical stapling procedures.

In the examples described above, the staple cartridges containing the staple forming features allow for the surgical tool like a surgical stapler to be reusable, such that the surgical stapler can be used multiple times in the same procedure with different types of staple cartridges, or sterilized and used in a different procedure with various types of staple cartridges, before being discarded.

The staple cartridges described in this section may be used in end effectors, such as a surgical staplers, or surgical stapling assemblies or stapler systems, such as those discussed above in the preceding sections.

V. STAPLE SHAPE CONTROL USING SELECTIVE BENDING SEGMENTS OF STAPLES

One important factor in staple formation is ensuring that the staple is able to get or "reach" across the entire tissue gap, or at least a sufficient amount of it, to have a properly formed staple. When staples begin to curl and deform too soon from exiting the staple pocket or cavity, or curl or deform at too steep an angle, the resulting staple ends up not grasping or gathering an appropriate amount of tissue, thus resulting in an ineffective staple. For example, with thicker tissue, if the staple legs started to curl either too soon or too steep of a radius immediately upon exiting the staple pocket, the height of the formed staple may not be very high, thus resulting in a poor staple formation having very little tissue being grasped by the formed staple.

As discussed above, in addition to arbor positions and dimensions, staple leg geometry (straight vs angled) may also be manipulated to control the desired outcome of formed staples. Specifically, changing staple leg geometries from straight to angled can change the curl of the staple legs. For instance, as discussed below in more detail, straight portions of staple legs may pass through staple forming or guide surfaces (e.g., arbors) without much, if any, plastic deformation or bending. Thus, a staple having straight segments or portions near the tip of the staple leg allows the upper portion of the staple to puncture the tissue without curling. While these upper straight segments of the staple may be slightly deflected to aim inward (i.e., toward the opposite staple leg), this portion of the staple is not yet plastically deformed or curled. Bending or curling occurs due to the angled approach of the staple leg wire toward the arbors.

Figure 35A:
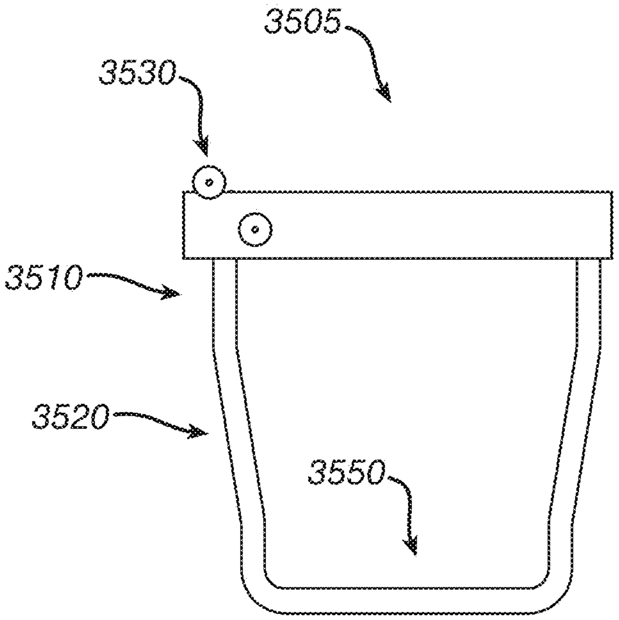
FIGS. 35A and 35B depict a staple having a staple shape according to one embodiment.
Figure 35B:
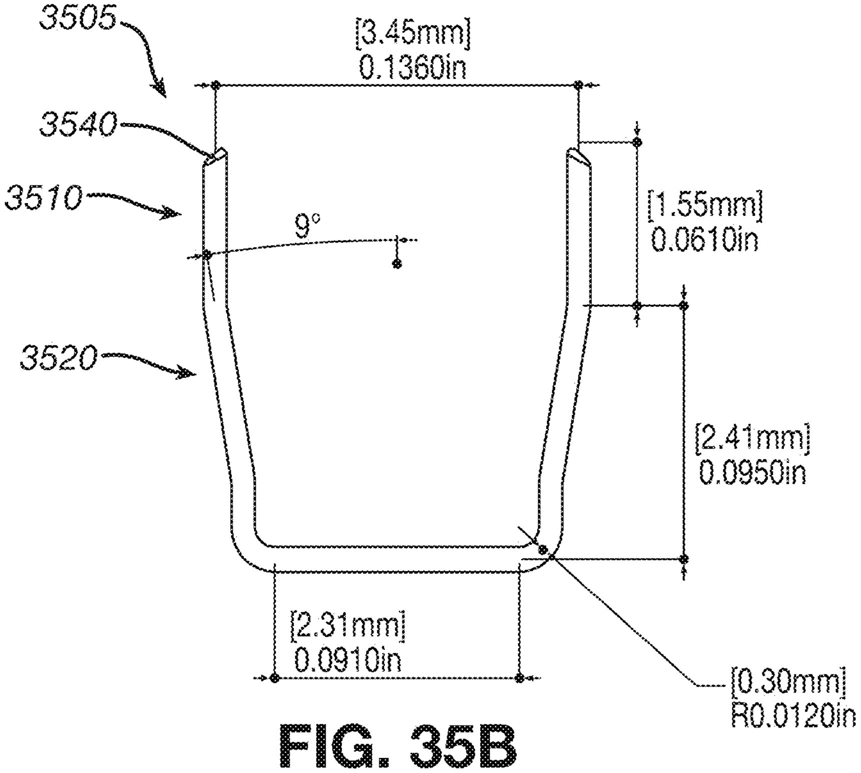

FIGS. 35A and 35B depict a staple having a staple shape according to one embodiment. Staple shape is important in order to get the staple to exit from the staple pocket in a manner that allows the staple to appropriately reach across the tissue gap and capture an appropriate amount of tissue. The exiting of the staple involves two primary goals. Initially, the goal is to get the staple legs to aim through guiding or forming surfaces, such as arbors, and allow the tips of the staple legs to puncture the tissue and reach the opposing jaw. Then the goal is to initiate bending of the staple legs in the lower half of the staple. This bending can occur before the tips of the staple legs make contact with the opposing jaw. With a staple having an upper straight part and lower angled part, the lower angled part of the legs interacting with the arbors is what initiates the staple to start bending and plastically deform or curl.

In one embodiment, a staple cartridge includes a staple opening containing an unformed staple 3505. As shown in FIGS. 35A and 35B, the staple 3505 has a first leg portion 3510 and a second leg portion 3520. The staple cartridge also includes a set of guides 3530 disposed adjacent the staple opening. When the staple 3505 exits the staple opening, the first leg portion 3510 has a first interaction with the guides 3530 and the second leg portion 3520 has a second interaction with the guides 3530, the second interaction being different than the first interaction. As shown and described below, the first interaction and the second interaction correspond to a degree or amount of plastic deformation experienced by the first leg portion 3510 and the second leg portion 3520, respectively. The first leg portion 3510 is adjacent a staple tip 3540, and the second leg portion 3520 is disposed between the first leg portion 3510 and a staple crown 3550.

As mentioned above, the angle at which the staple legs advance toward the guides 3530 or arbors has an impact on how quickly and at what radius the staple legs curl into the tissue. As can be seen from FIGS. 35A and 35B, the first leg portion 3510 includes a first angle of approach to the guides 3530 and the second leg portion 3520 includes a second angle of approach to the guides 3530. The second angle of approach is greater than the first angle of approach. In the example shown in FIGS. 35A and 35B, the first angle of approach of the first leg portion 3510 is very small. In some cases, the first leg portion 3510 may be substantially vertical, where the first leg portion 3510 does not approach the arbors at an angle. In this case, since the first leg portion 3510 enters or passes the guides 3530 almost straight on, the first leg portion 3510 essentially passes through the guides 3530 with little or no interference from the guides 3530. In this example, during the first interaction with the guides 3530, the first leg portion 3510 remains undeformed by the guides 3530.

Figure 36A:
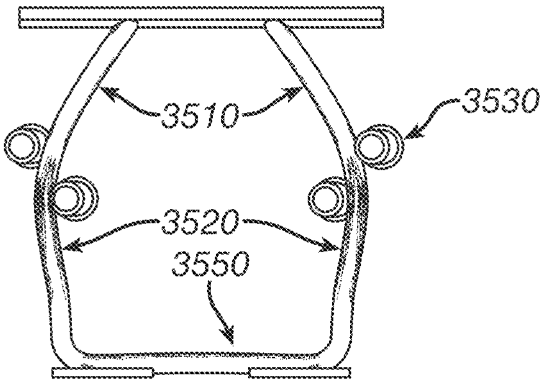
FIGS. 36A-C depict a finite element analysis (FEA) model and force curve of the staple of FIG. 35 according to one embodiment.
Figure 36B:
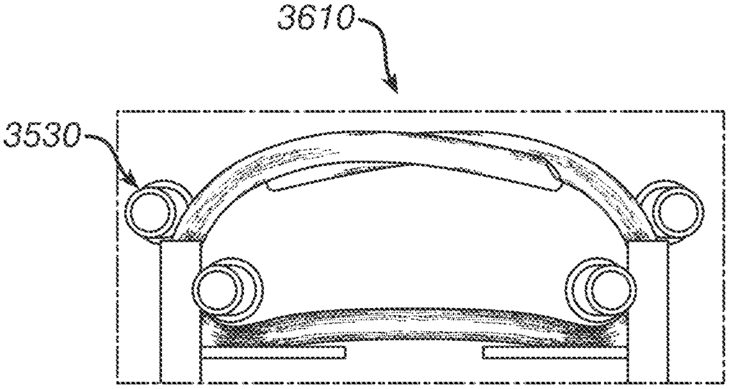

FIGS. 36A and 36B depict a finite element analysis (FEA) of a staple, such as staple 3505 of FIGS. 35A and 35B, being advanced through guides, such as guides 3530 of FIGS. 35A and 35B. The hatched portions of the staple 3505 in the images of FIGS. 36A and 36B indicate where the staple 3505 experiences plastic deformation forces. As shown in FIG. 36A, the first leg portion 3510 has passed through the guides 3530 without experiencing any plastic deformation.

However, the lower or second leg portion 3520 of the staple 3505 does experience plastic deformation. Since the second leg portion 3520 of the staple 3505 approaches the guides 3530 at an angle, the second leg portion 3520 is bent or deformed by the guides 3530. In other words, during the second interaction with the guides 3530, the second leg portion 3520 is plastically deformed by the guides 3530. As shown in FIG. 36A, deformation forces are experienced by the second leg portion 3520 as the second leg portion 3520 interacts with the guides 3530.

As the staple 3505 continues to be driven out of the staple pocket and exits the staple opening, the first leg portion 3510 is formed to a first radius and the second leg portion 3520 is formed to a second radius different than the first radius. In one example, the second radius is tighter than first radius. The image of FIG. 36B depicts the staple 3505 in the final stages of a firing stroke of being formed into a formed staple 3610. The deformation forces during this phase of staple formation impact the second leg portion 3520 and the staple crown 3550.

Figure 36C:
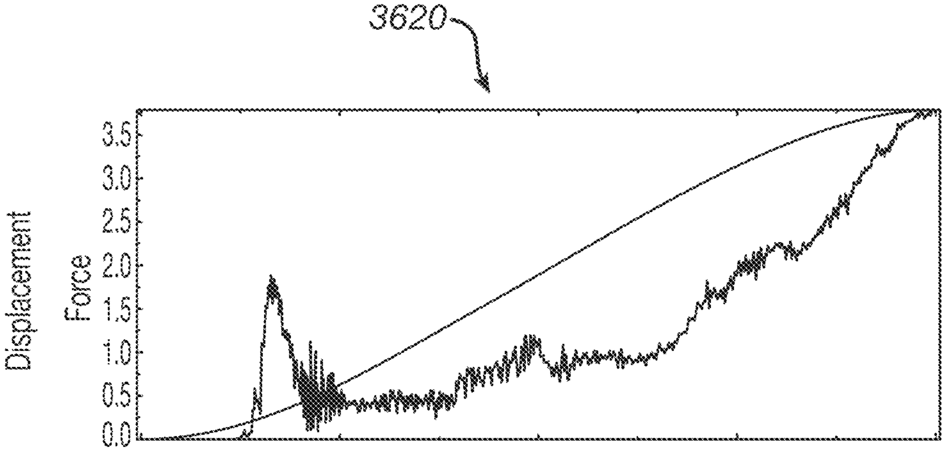

FIG. 36C depicts a force curve 3620, which shows the forces (y-axis) of firing the staple during the firing stroke (x-axis being the time of the firing stroke). As shown, the first part of the force curve 3620 is essentially flat, which corresponds to the first leg portion 3510 passing through the guides 3530 with no deformation. The force curve 3620 spikes when the second leg portion 3520 contacts and interacts with the guides 3530. After this initial deformation of the second leg portion 3520, the force curve 3620 plateaus and then gradually increases as the second leg portion 3520 continues to be deformed (curled). The end of the firing stroke imparts the greatest force on the staple, as seen on the far right of the force curve 3620, which deforms the second leg portion 3520 near the staple crown 3550 in order to finish forming the formed staple 3610.

In some embodiments, the different leg portions of the staple 3505 may be out of plane from each other. For example, the first leg portion 3510 is in a first plane and the second leg portion 3520 is in a second plane different from the first plane. As discussed below, the angled segment of the staple (e.g., the second leg portion 3520) may be angled in two different planes.

An embodiment using this type of "out of plane" staple allows the use of static arbors offset from one another to curl staple legs and not deploy with the formed staples. In this case, a preformed staple has angles in two planes to govern and control which portion of the staple contacts, and is deformed by, the offset arbors. The top portion of an unformed staple leg sits away from an upper guide or arbor (of a set of two arbors, for example), so as it is lifted, no curling occurs. The middle portion of the unformed staple leg, which is angled in two planes, contacts both top and bottom arbors as the staple is lifted, causing the staple leg to curl. The lower portion of the unformed staple leg includes the crown, which sits away from the lower arbor. As the driver pushes the formed staple out, the formed staple can freely exit the staple cartridge.

Figure 37A:
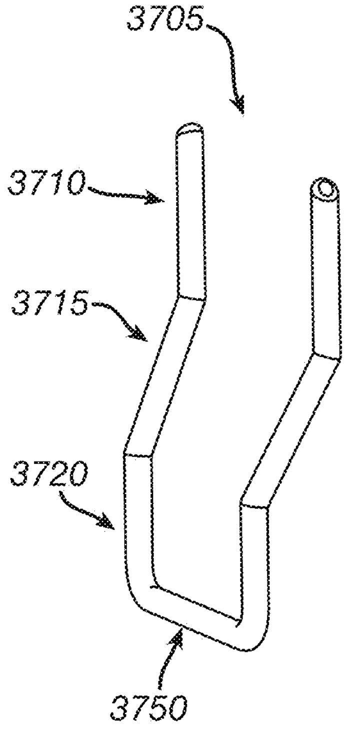
FIGS. 37A-C depict a staple having a staple shape with staple legs in different planes according to one embodiment.
Figure 37B:
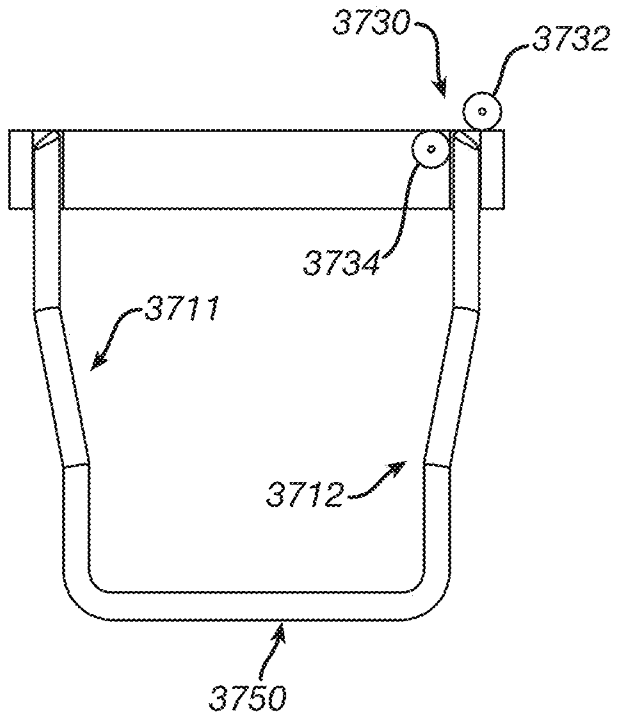
Figure 37C:
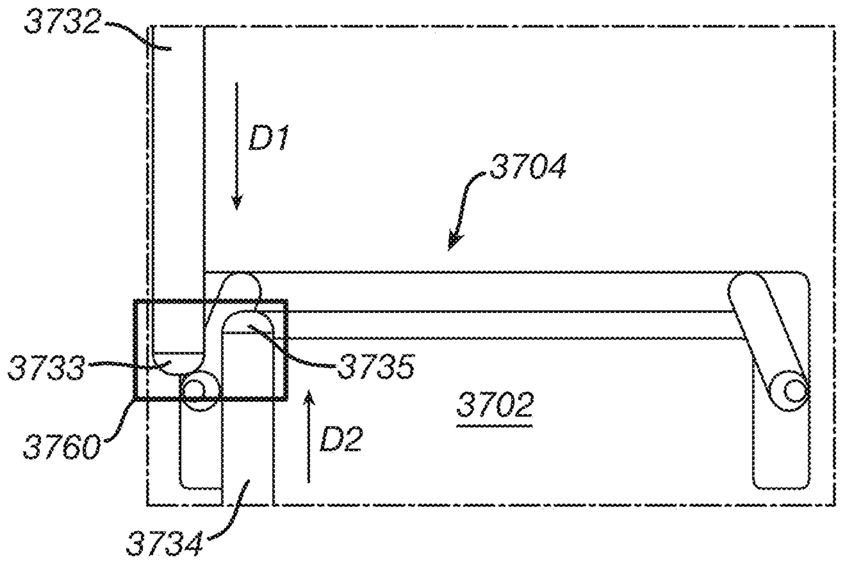

FIGS. 37A-C depict a staple having a staple shape with staple legs in different planes according to one embodiment. FIG. 37A depicts a perspective view of a preformed staple 3705 having staple legs angled in two planes. FIG. 37B depicts a front view of the staple 3705 where the tips of the staple 3705 are adjacent a set of guides, or arbors 3730. FIG. 37C shows a plan or top view looking down into an opening 3704 of a staple pocket 3702 when the staple 3705 is in an initial or resting position within the staple pocket 3702 (i.e., before firing).

In one embodiment, as shown in FIGS. 37-40, a surgical staple cartridge includes a staple pocket 3702 having an opening 3704 and containing a preformed staple 3705, and a set of arbors 3730 disposed adjacent the opening 3704. The staple 3705 has an upper leg portion 3710, a middle leg portion 3715, and a lower leg portion 3720. As described more fully below, the set of arbors 3730 are configured to deform the middle leg portion 3715 of the staple 3705 as the staple 3705 exits the staple pocket 3702 at the opening 3704 along an exit path, while the upper leg portion 3710 and the lower leg portion 3720 remain undeformed as the staple 3705 exits the staple pocket 3702 at the opening 3704.

As shown in FIGS. 37-40, the upper leg portion 3710 and the lower leg portion 3710 are straight and parallel to one another, and the middle leg portion 3715 is angled relative to the upper leg portion 3710 and the lower leg portion 3720. As mentioned above, the middle leg portion 3715 is angled in two planes.

As shown in FIGS. 37B and 37C, the set of arbors 3730 include a top arbor 3732 extending into the exit path from a first direction D1 and a bottom arbor 3734 offset vertically and horizontally from the top arbor 3732. The bottom arbor 3734 extends into the exit path from a second direction D2 that is opposite the first direction D1. An end 3733 of the top arbor 3732 and an end 3735 of the bottom arbor 3734 overlap in the exit path by an overlap distance in an overlap zone 3760 (see the box 3760 in FIG. 37C). The ends 3733, 3735 of the arbors 3732, 3734 may be rounded or radiused, as shown in the figures.

Figure 38A:
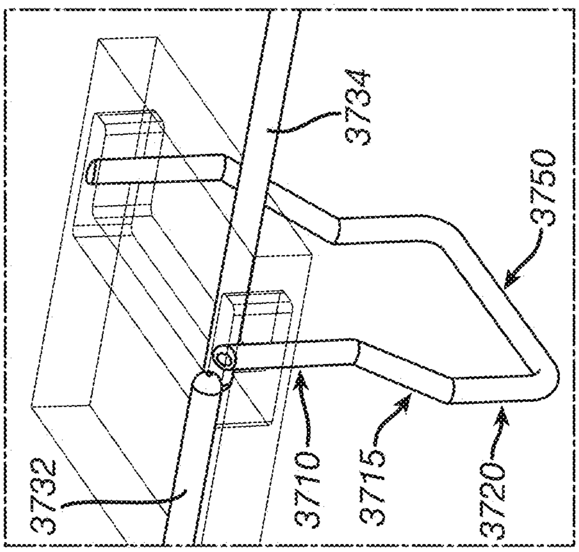
FIGS. 38A-C illustrate a perspective view of movement of a preformed staple through a staple pocket and out an opening during a firing stroke according to one embodiment.
Figure 38B:
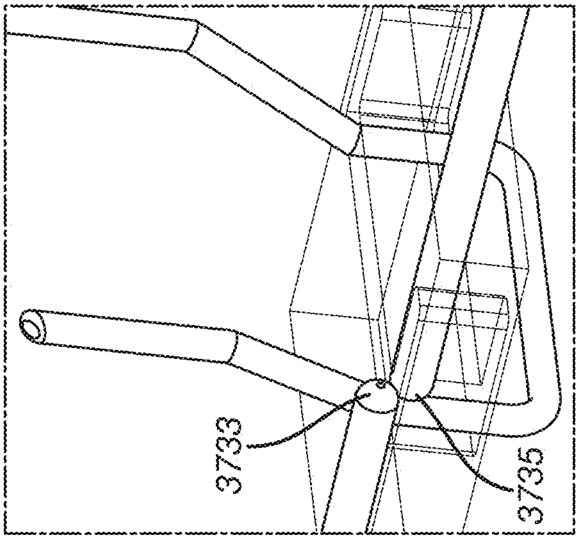
Figure 38C:
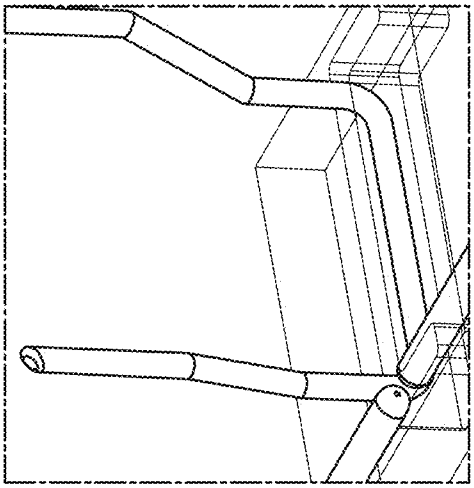
Figure 39A:
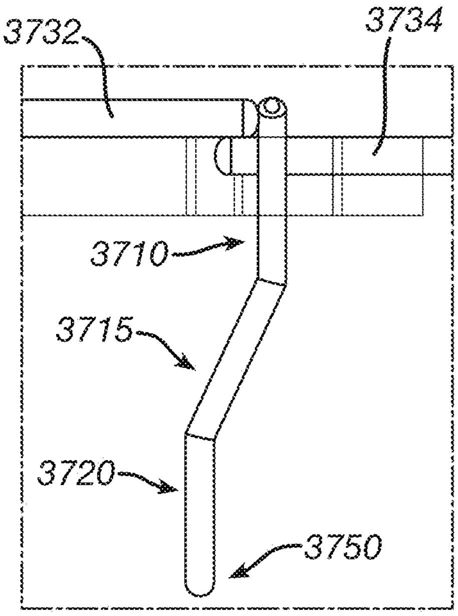
FIGS. 39A-C illustrate a side view of movement of the preformed staple through the staple pocket and out the opening during the firing stroke according to one embodiment.
Figure 39B:
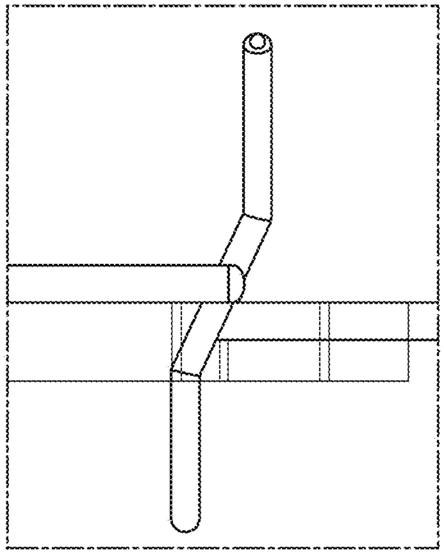
Figure 39C:
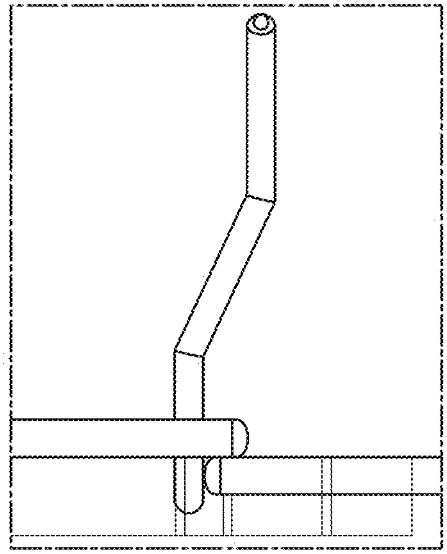
Figure 40A:
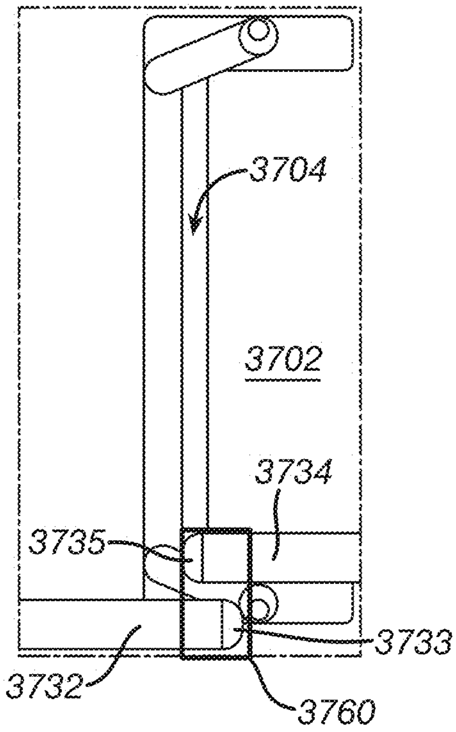
FIGS. 40A-C illustrate a top view of movement of the preformed staple through the staple pocket and out the opening during the firing stroke according to one embodiment.
Figure 40B:
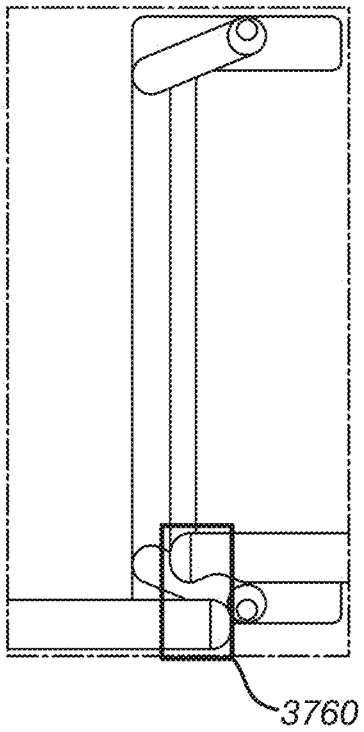
Figure 40C:
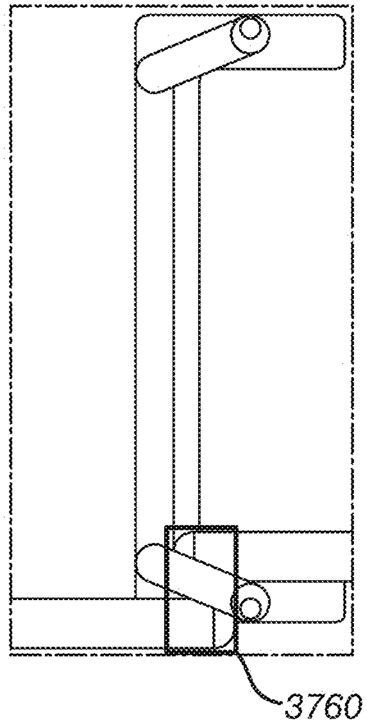

FIGS. 38-40 illustrate movement of a preformed staple 3705 upward through a staple pocket 3702 and exiting an opening 3704. For example, the movement depicted in FIGS. 38-40 represent movement of a staple 3705 configured to exit a staple opening 3704 during a firing stroke. More specifically, FIGS. 38A-C illustrate a perspective view of movement of the preformed staple 3705 through the staple pocket 3702 and out the opening 3704 during a firing stroke; FIGS. 39A-C illustrate a side view of movement of the preformed staple 3705 through the staple pocket 3702 and out the opening 3704 during the firing stroke; and FIGS. 40A-C illustrate a top view of movement of the preformed staple 3705 through the staple pocket 3702 and out the opening 3704 during the firing stroke. The firing stroke illustrated in FIGS. 38-40 may refer to the staple cartridge having the staple pocket 3702 described above, or to a staple cartridge 3702 having a staple opening containing a preformed staple 3705, the staple 3705 having two legs 3711, 3712 and a crown 3750, where the two legs 3711, 3712 include a straight portion 3710, a crown portion 3720, and an angled portion 3715 between the straight portion 3710 and the crown portion 3720. For simplicity, FIGS. 38-40 do not show deformation of the staple 3705 as it passes through the arbors. These figures are intended to show where there is interaction between arbors and the staple legs.

The firing stroke described herein may include three stages: a first or initial stage of firing; a second stage of firing; and third stage of firing. FIGS. 38A, 39A, and 40A represent the first stage of firing. FIGS. 38B, 39B, and 40B represent the second stage of firing. FIGS. 38C, 39C, and 40C represent the third stage of firing.

As seen in FIGS. 38A, 39A, and 40A, the preformed staple 3705 is in an initial or first stage of a firing stroke. In this first or resting stage, the upper leg portion 3710 is disposed in the staple pocket 3702 beyond the end 3733 of the top arbor 3732 in the first direction D1. In this way, as the staple 3705 is driven upwards, the upper leg portion 3710 passes by the end 3733 of the top arbor 3732 without being deformed. In other words, during the first stage of firing, the straight portion 3710 of the two legs 3711, 3712 is configured to bypass the arbors 3730 and pierce tissue.

As seen in FIGS. 38B, 39B, and 40B, the preformed staple 3705 is in a deformation or second stage of the firing stroke. In this deformation or second stage, since the middle leg portions 3715 of the staple legs 3711, 3712 are angled outward in two planes, the middle leg portions 3715 of the staple legs 3711, 3712 contact and interface with both of the arbors 3732, 3734 and become deformed. In this way, the set of arbors 3730 deform the middle leg portion 3715 of the staple 3705 as the middle leg portion 3715 passes between the top arbor 3732 and the bottom arbor 3734 in the overlap zone 3760. In other words, during the second stage of firing, the arbors 3730 are configured to curl the two legs 3711, 3712 as the angled portion 3715 of the two legs 3711, 3712 interface with the arbors 3730 to capture and compress tissue.

As seen in FIGS. 38C, 39C, and 40C, the preformed staple 3705 is in a final or third stage of the firing stroke. In this final or third stage, since the lower leg portion 3720, including a staple crown 3750, is disposed in the staple pocket 3702 beyond the end 3735 of the bottom arbor 3734 in the second direction D2, as the staple 3705 is driven upwards, the lower leg portion 3720 passes by the end 3735 of the bottom arbor 3734 without being deformed. In other words, during the third stage of firing, the crown portion 3720 of the two legs 3711, 3712 is configured to bypass the arbors 3730, such that the staple 3705 is releasable from the staple cartridge 3702.

In another embodiment, the angle of the middle leg portion 3715 of the staple 3705 may be more abrupt and in a single plane to avoid one of the arbors. For example, the middle leg portion 3715 may bend at a 90 degree angle relative to the both the upper leg portion 3710 and lower leg portion 3720 in a single plane. For instance, if looking at the staple from the side, the lower leg portion 3720 may extend upwards form the crown 3750, the middle leg portion 3715 may bend at 90 degrees to the left or right (as looking at the side view), and the upper leg portion 3710 may extend straight upward from the middle leg portion 3715. When looking at this configuration from the front or back, all staple legs would be aligned (i.e., no outward angles in another plane).

The angles and planes of the top, middle, and lower portions of a staple can be created based on the desired amount of tissue being captured, and the desired curl radius. For example, a long top section may reach far through thick tissue, and a steep angle of the middle portion may form a tight radius.

The staple shape and arrangement described above includes a set of arbors 3730 that are static arbors that remain in the surgical staple cartridge after the staple 3705 exits the staple pocket 3702. This avoids the issue of having to move or deploy the arbors in order to fire a staple. Thus, the disclosed staple cartridges accommodate for spanning the tissue gap and allow staple release. This arrangement could be used to form planar or 3D staples, and can be used on endocutters, open linear staplers, circular staplers, right-angle staplers, or other devices that deploy staples between jaws.

The staple cartridges described in this section may be used in end effectors, such as a surgical staplers, or surgical stapling assemblies or stapler systems, such as those discussed above in the preceding sections.

VI. STAPLE CARTRIDGE WITH STATIC ANGLED ARBORS TO FORM THREE-DIMENSIONAL (3D) STAPLES

As discussed above, the staple forming surfaces, such as arbors, may be fixed and disposed on an inner wall or surface of a staple cartridge pocket or opening. The arbors may be positioned at or near the exit of the cartridge pocket (also referred to as a staple pocket) such that the staple legs of a staple are curled by the arbors as the staple legs exit the staple pocket. In addition to arbor positions and dimensions described above where the arbor is fixed during the formation of the staple (i.e., during the curling of the staple legs as the staple legs exit the staple pocket), angles with respect to the arbors and the crown of the staple impact the shape of the formed staple as well. In one embodiment, the arbors may extend away from the inner walls or surface of the staple pocket at an angle to create an angle between the arbors and the crown. In another embodiment, the crown of the staple may be angled due to an angled staple pocket and the arbors may be parallel to one another (e.g., along a length of the staple cartridge). In yet another embodiment, the staple pocket opening may be angled with respect to the arbors that may extend perpendicularly away from the inner walls or surface of the staple pocket. Arrangements such as this may create legs of staples that are deflected laterally and obliquely relative to the vertical plane passing through the crown of staple (i.e., legs of staples that are out of plane from each other), resulting in three-dimensional (3D) staples, such as the types described in U.S. Pat. No. 11,406,379, entitled "Surgical End Effectors With Staple Cartridges," issued Aug. 9, 2022, the disclosure of which is incorporated by reference herein, in its entirety.

In one embodiment, to form 3D staples that spread out the pressure to the tissue, the arbor surfaces can be angled relative to the staple crown. A wide range of angles are possible to create formed staples of different shapes. A slight angle, such as 10 degrees for example, forms a staple that is similar in shape to those described in U.S. Pat. No. 11,406,379 mentioned above. This moves the legs away from each other (i.e., out of plane) during forming to avoid legs crashing into each other and also generates a wider compression zone on the tissue. Severe angles, such as 90 degrees for example, are also achievable with an arbor set. Arbor sets to produce 3D staples may be utilized on various types of staples, or possibly a subset of staples to project a different pressure profile to the tissue, for example at the beginning or end of a staple line. Angles in between those discussed above may be achievable.

In some examples, the arbor surfaces that generate the bending/curling are parallel to each other, and the axis of the arbors may be skewed relative to the staple crown to angle the legs in a desired direction. As mentioned above, this may be accomplished by having the arbors extend perpendicularly out from the staple channel and angle the staple crown within the staple channel, or by skewing the angle at which the arbors extend out from the staple channel and having the staple crown situated in the staple channel parallel with the staple channel (i.e., in straight rows). In the examples where the crown is angled within the staple channel, the drivers may be angled as well to maintain alignment between the staple drivers and staple crowns.

Figure 41:
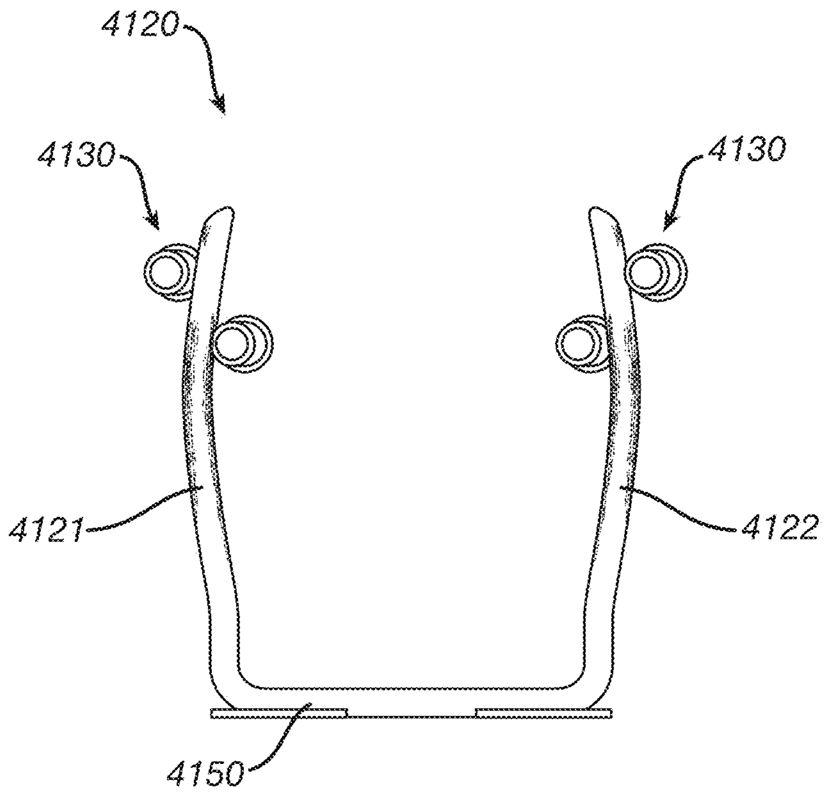
FIG. 41 depicts a finite element analysis (FEA) model of a staple and angled arbors according to one embodiment.

FIG. 41 depicts a finite element analysis (FEA) model of a staple and angled arbors according to one embodiment. The staple in FIG. 41 is an unformed staple 4120 having staple legs 4121, 4122 and a crown 4150. The unformed staple 4120 in FIG. 41 is shown with a set of guide surfaces 4130. While the unformed staple 4120 and guide surfaces 4130 of FIG. 41 are shown as part of a FEA model, the unformed staple 4120 and guide surfaces 4130 of FIG. 41 may be used with a staple cartridge, such as those described in the sections above.

As mentioned above, there are different arrangements that result in staple legs being curled laterally and obliquely relative to a vertical plane passing through the crown of staple, resulting in three-dimensional (3D) staples. In the example shown in FIG. 41, the arrangement to create 3D staples includes angled arbors. In one embodiment, a staple cartridge includes a staple pocket having an opening and containing a staple 4120 with staple legs 4121, 4122 and a staple crown 4150. The staple cartridge also includes a set of arbors 4130 disposed adjacent the opening. In one embodiment, the set of arbors 4130 may be integrally formed with a sidewall of the staple pocket and extend away from the sidewall at an angle. As shown in a front facing view of FIG. 41, the set of arbors 4130 are angled (toward the reader and to the left of the reader). In this way, the set of guide surfaces 4130 are obliquely oriented relative to a longitudinal axis of the staple channel or pocket.

Figure 42A:
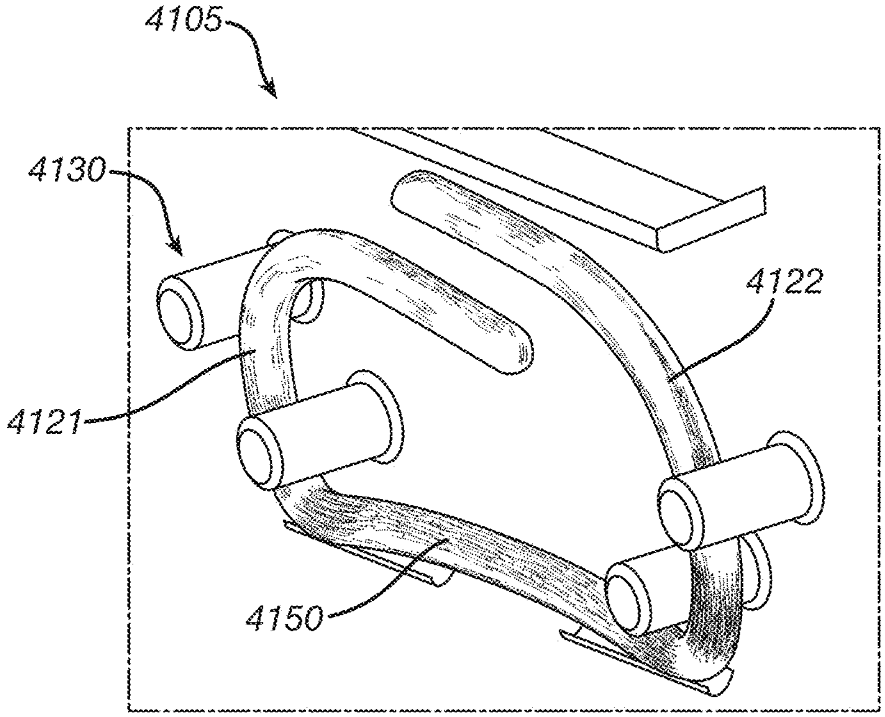
FIGS. 42A and 42B illustrate the staple of FIG. 41 formed by the set of arbors of FIG. 41.
Figure 42B:
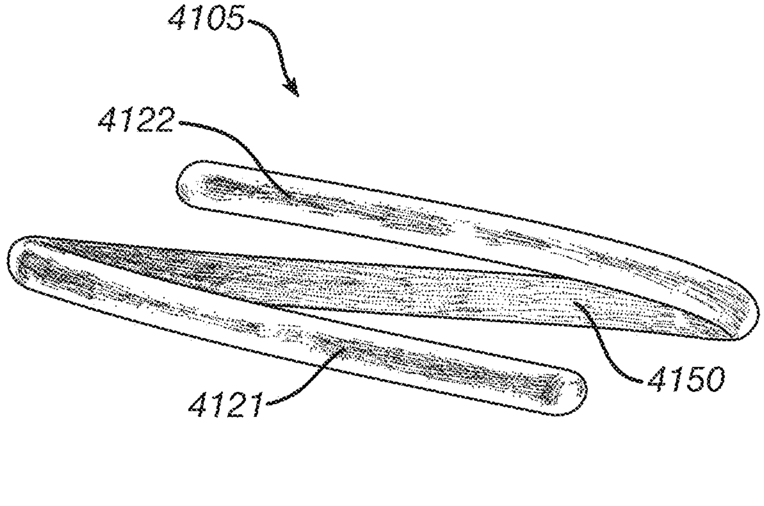

Similarly to the arbors discussed in the sections above, the set of arbors 4130 of FIG. 41 are configured to curl or plastically deform the staple legs 4121, 4122 of the staple 4120 as the staple legs 4121, 4122 exit the staple pocket at the opening to form a formed staple 4105. In other words, the unformed staple 4120 is curled or plastically deformed into a formed staple 4105 by the set of guide surfaces 4130. FIGS. 42A and 42B depict the staple of FIG. 41 formed by the set of arbors of FIG. 41. FIG. 42A is a perspective view of the formed staple 4105 and FIG. 42B is a top view of the formed staple 4105. As shown in FIGS. 42A and 42B, as the staple legs 4121, 4122 are curled or plastically deformed by the set of arbors 4130 as the staple is being driven out of the staple pocket by a driver, a first staple leg 4121 curls and extends away from a second staple leg 4122 (i.e., out of plane with respect to each other). The hatched portions of the staple 4105 in FIGS. 41 and 42 indicate where the staple 4105 experiences plastic deformation forces.

Specifically, referring to a standard xyz-coordinate system where in the figures the x-direction is left and right, the y-direction is up and down, and the z-direction is into and out of the page, the first staple leg 4121 curls and extends in a first x-direction and a first z-direction (e.g., to the right and out of the page), whereas the second staple leg 4122 curls and extends in a second x-direction opposite the first x-direction and a second z-direction opposite the first z-direction (e.g., to the left and into the page). Both staple legs 4121, 4122 extend away from the crown 4150 in the z-direction. In this way, the staple legs 4121, 4122 of the formed staple 4105 are in a first plane and the staple crown 4150 of the formed staple is in a second plane different from the first plane. This results in the formed staple 4105 having a 3D shape (i.e., values in all three coordinate directions).

As noted above and shown in FIGS. 42A and 42B, the staple legs 4121, 4122 of the formed staple 4105 are spaced apart from each other, such that a distance between the staple legs 4121, 4122 of the formed staple 4105 is greater than a width of the staple pocket. One advantage of a 3D staple shape is allowing the staple pressure to be spread out on the tissue and not localized along the same line of regular staple formation.

In one embodiment, having the arrangement described above with respect to FIGS. 41 and 42 allows the staple crown 4150 to be parallel to a cutline and the set of arbors 4130 be angled relative to the cut line.

Figure 43:
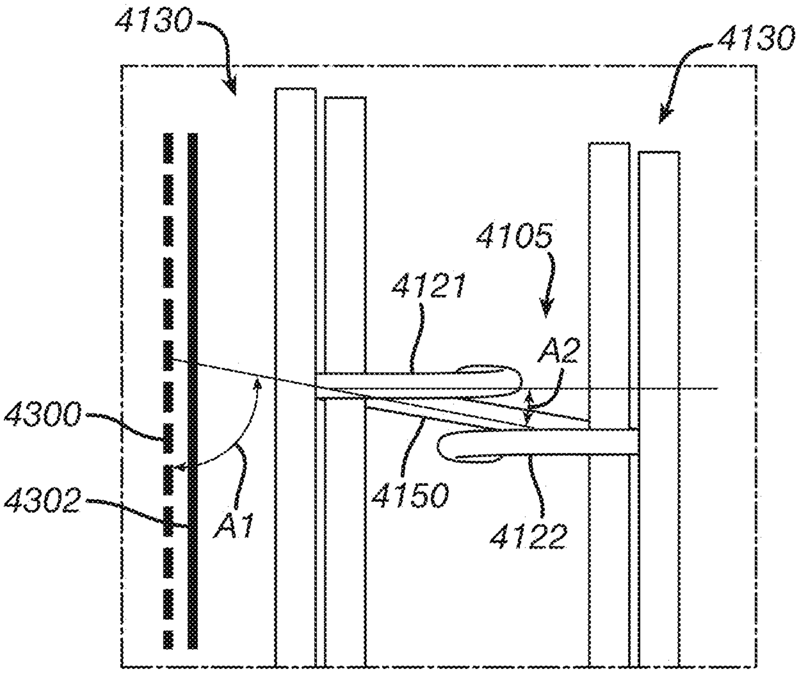
FIG. 43 depicts a top view of 3D staples formed using straight arbors and angled staple channels according to one embodiment.
Figure 44:
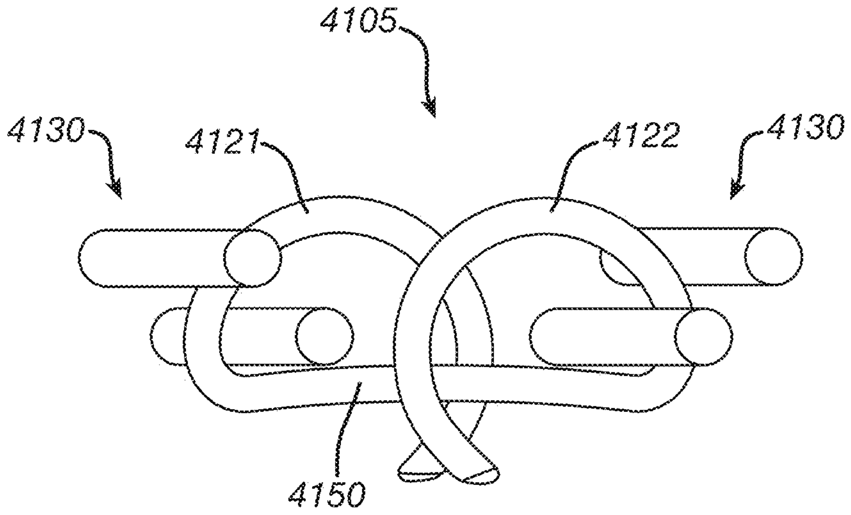
FIG. 44 depicts a staple in a B-shape pattern formed using straight arbors and angled staple channels according to one embodiment.

In another arrangement, such as that shown in FIGS. 43 and 44, 3D staples are formed using an angled crown. In one example, arbor pins may be used as continuous wires or rods on a surface of the staple cartridge that span along the length of the staple cartridge. In this example, the arbor pins may be straight, and each staple pocket could be angled. In FIGS. 43 and 44, the crown 4150 and the staple legs 4121, 4122 of the formed staple 4105 are angled relative to one another.

FIG. 43 depicts a top view of 3D staples formed using straight arbors and angled staple channels according to one embodiment. In the example shown in FIG. 43, the arrangement to create 3D staples includes an angled crown. In one embodiment, a staple cartridge includes a set of guide surfaces 4130 disposed on or in, and along a length of, the staple cartridge parallel to a longitudinal axis 4300 of the staple cartridge. The longitudinal axis 4300 runs from the distal end of the cartridge to the proximal end of the cartridge. The longitudinal axis 4300 is also parallel to a cut line 4302 formed using the cartridges disclosed herein.

The staple cartridge also includes a staple channel having an opening and containing a staple with staple legs 4121, 4122 and a crown 4150. In this example, the crown 4150 is obliquely oriented relative to the longitudinal axis 4300. In other words, the crown 4150 is slanted relative to the longitudinal axis, as well as the set of guide surfaces 4130, as shown in FIG. 43. As shown in FIG. 43, the crown 4150 is angled with respect to the longitudinal axis 4300 by angle A1. In this way, the crown 4150 is also angled with respect to an axis perpendicular to the set of guide surfaces 4130, or the formed staple legs 4121, 4122, as shown by angle A2 in FIG. 43.

Similar to above, the set of guide surfaces 4130 are configured to curl the staple legs 4121, 4122 of the staple as the staple legs 4121, 4122 exit the staple channel at the opening. In other words, during a firing stroke, the staple legs 4121, 4122 of the staple are curled into a formed staple 4105 by the set of guide surfaces 4130. See FIGS. 43 and 44. As shown in FIGS. 43 and 44, the formed staple 4105 has a three-dimensional (3D) shape.

In addition to the 3D shape of the formed staple discussed above, the arrangements disclosed herein may also form the staple into other shapes, such as a B-shape, B-form, or B-formed configuration. FIG. 44 depicts a staple in a B-shape pattern formed using straight arbors and angled staple channels according to one embodiment. In this embodiment, the formed staple legs 4121, 4122 are shown in a position that reaches beyond the crown 4150.

Referring back to FIG. 43, in the arrangement of an angled crown 4150 or staple channel, the staple legs 4121, 4122 of the formed staple may still be parallel, or substantially parallel, to each other. In one embodiment, as shown in FIG. 43, the set of guide surfaces 4130 are parallel to a cut line 4302 and the crown 4150 is angled relative to the cut line 4302. In another embodiment, the staple crown 4150 is parallel to the cutline 4302 and the set of arbors 4130 are angled relative to the cut line 4302.

In either of the arrangements discussed above, a staple cartridge may be used that includes a staple channel having an opening and containing an unformed staple 4120 with staple legs 4121, 4122 and a crown 4150 and a set of guide surfaces 4130 disposed adjacent the opening. The set of guide surfaces 4130 are configured to bend the staple legs 4121, 4122 of the unformed staple 4120 as the staple legs 4121, 4122 exit the staple channel at the opening. In both arrangements discussed above, the set of guide surfaces 4130 and the crown 4150 are angled relative to one another. In one embodiment, an angle between the set of guide surfaces 4130 and the crown 4150 is between 5 and 20 degrees. In another embodiment, the angle between the set of guide surfaces 4130 and the crown 4150 is between 10 and 90 degrees.

For example, in some embodiments, arbors may be placed adjacent the staple pocket opening in different locations or, in another embodiment, additional arbors may be used in different locations adjacent the opening where the staple legs exit the staple channel or pocket. For example, in addition to, or in lieu of, the arbors discussed above, other arbors may be included in tissue gripping features disposed on the cartridge deck at the staple openings. These additional or different arbors may extend into the staple path from a direction different than that described above and may be configured to bend or curl staple legs further out of plane.

Curling staple legs substantially out of plane (i.e., more than that shown in FIGS. 42-44) allows for staples to be wider than the staple pocket, which allows the staples to overlap and interlace or intertwine with adjacent rows or lines of staples.

Figure 45:
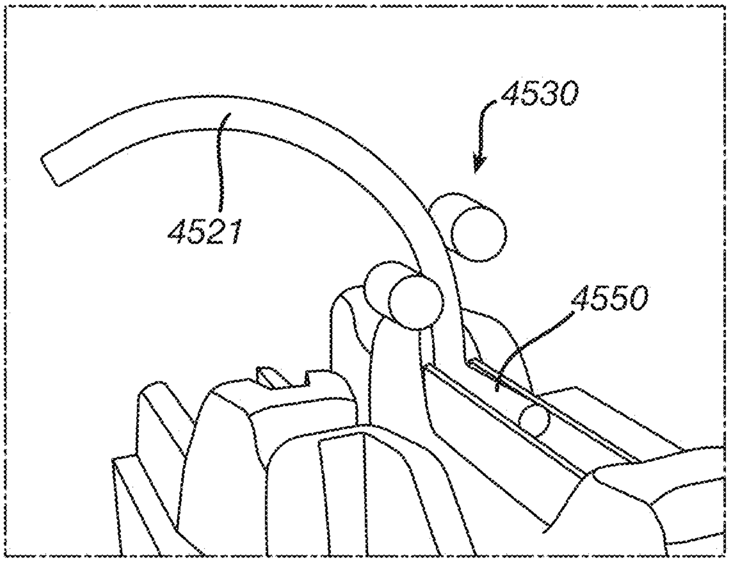
FIG. 45 depicts arbors placed on opposite sides of a crown of a staple to bend a staple out of plane according to one embodiment.

FIG. 45 depicts arbors placed on opposite sides of a crown of a staple to curl a staple out of plane according to one embodiment. In one embodiment, a staple cartridge includes a staple channel containing a staple with staple legs 4521 and a crown 4550. The staple cartridge also includes a set of arbors 4530 disposed adjacent the staple channel. As with the arrangements above, the set of arbors 4530 are configured to curl or plastically deform the staple legs 4521 of the staple as the staple legs 4521 exit the staple channel. A difference, however, is that in some embodiments, such as that shown in FIG. 45, the staple leg 4521 may be curled by the arbors 4530 up to 90 degrees from the crown 4550 (e.g., perpendicular to the crown 4550).

The ability to control bending and curling of staple legs out of plane in different directions opens up the possibilities of customizing staple formation for various specific needs. For example, some staples may be formed with 2D staples, others with 3D staples, and yet others that are largely out of plane. This allows the application of different pressure profiles to the tissue. For example, the beginning or ending of a staple line may have different pressure profiles than other locations along the cut line. In this case, forming staples with different degrees of deformation results in unique pressure profiles for these different needs.

In some examples, the set of guide surfaces 4130 are releasable with the formed staple 4105. For instance, in the example of continuous arbor pins laid along the length of the cartridge, the arbor pins may be snapped into place and releasable with the formed staples to form a ladder-like firing.

As mentioned above, in some embodiments, one or more of the guides (e.g., arbors or guide surfaces) or staple forming surfaces may be movable, releasable or detachable. For example, the guides/arbors or staple forming surfaces may be released with the fully curled staple legs after the staple formation is complete. In this case, the guides/arbors may be made out of a bioabsorbable material. In another example, the staple cartridge may contain a mechanism or device that retracts the guides/arbors. In other words, the guides/arbors may be moved out of the way to allow the staples to deploy or exit the cartridge pocket. In yet another example, the guides/arbors may be designed to allow the staple crown to pass through the guides/arbors. Thus, the staple cartridges described here may use guides/arbors of the types described in: U.S. patent application Ser. No. 18/781,551, entitled "Staple Cartridge Containing Forming Surfaces That Bend Staple Legs Upon Exiting"; U.S. patent application Ser. No. 18/781,578, entitled "Deployable Arbor Sets That Break Away From Staple Cartridge"; and U.S. patent application Ser. No. 18/781,583, entitled "Multi-Part Staple With Separate Legs And Crown To Facilitate Staple Release From Arbors," the disclosures of which are incorporated by reference herein, in their entirety.

The staple cartridges described in this section may be used in end effectors, such as a surgical staplers, or surgical stapling assemblies or stapler systems, such as those discussed above in the preceding sections. Further, the arrangement of the arbors described herein to produce 3D staples may also be combined with any one or more of the teachings disclosed in: U.S. patent application Ser. No. 18/781,551, entitled "Staple Cartridge Containing Forming Surfaces That Bend Staple Legs Upon Exiting"; U.S. patent application Ser. No. 18/781,555, entitled "Stapler Device That Forms Staples From Various Cartridges Having Different Row Patterns"; U.S. patent application Ser. No. 18/781,558, entitled "Staple Shape Control Using Selective Bending Segments Of Staples"; U.S. patent application Ser. No. 18/781,573, entitled "Staple Cartridge With Dynamic Arbors That Produce Non-Constant Curl Radius"; U.S. patent application Ser. No. 18/781,578, entitled "Deployable Arbor Sets That Break Away From Staple Cartridge"; and U.S. patent application Ser. No. 18/781,583, entitled "Multi-Part Staple With Separate Legs And Crown To Facilitate Staple Release From Arbors.".

VII. STAPLE CARTRIDGE WITH DYNAMIC ARBORS THAT PRODUCE NON-CONSTANT CURL RADIUS

In contrast to the embodiments described above which described arbors that are static (fixed in one location) during the firing stroke, the staple cartridge disclosed below involves dynamic arbors or guide surfaces that are movable. The ability to translate arbors laterally within staple pockets allows the arbors to contact staple legs in such a way so as to change the bend radius of the staple legs as the staple legs are lifted by drivers and advanced out of the staple pocket during a firing stroke. This movement and change in curl radius during a firing stroke results in staples being formed with a non-constant curl radius. In other words, the bend radius is dynamic. This is an alternative to using different staple shapes, such as staple legs with angles in one or two planes, to control the curl radius during staple formation, but can also be used with the types of staples as disclosed in U.S. patent application Ser. No. 18/781,558, entitled "Staple Shape Control Using Selective Bending Segments of Staples," filed on Jul. 23, 2024, the disclosure of which is incorporated by reference herein, in its entirety.

The embodiments disclosed herein use a combination of dynamic arbors and static arbors. For example, the arbors, or set of arbors, described herein may be the same as those described above, such as having a first/upper/outer arbor and a second/lower/inner arbor, each disposed adjacent an opening of a staple pocket. The difference is that the second/lower/inner arbors (i.e., a subset of the set of arbors) disclosed in this section are dynamic arbors and capable of moving or translating at least laterally within a staple pocket or channel. In some embodiments, the dynamic arbors are moved by another movable component of the staple cartridge, such as a driver or a leaf spring, for example. In some cases, the initial position of the arbors before they are moved may result in a more typical curl radius, whereas the curl radius tightens as the dynamic arbors are moved by another movable component of the staple cartridge. For example, the curl radius of a staple leg during a firing stroke may tighten as the staple is lifted by a driver during the firing stroke. In another example, the curl radius of the staple leg may tighten as compression force on a leaf spring coupled to the dynamic arbor increases.

In one embodiment, a camming feature is provided on, or part of, the top (e.g., top surface) of a driver, such that as the driver advances to lift the staple upward, the camming feature contacts the second/lower/inner arbor, which is dynamic, causing the arbor to translate or deflect laterally, which in turn changes (e.g., tightens) the curl radius of the staple leg.

In another embodiment, a compression spring, such as a leaf spring, is provided on the staple cartridge and mechanically coupled to one or more dynamic arbors, such that as compression force is applied to the leaf spring, the leaf spring flattens, causing the position of the dynamic arbors to translate or deflect laterally, which in turn changes (e.g., tightens) the curl radius of the staple leg.

Figure 46A:
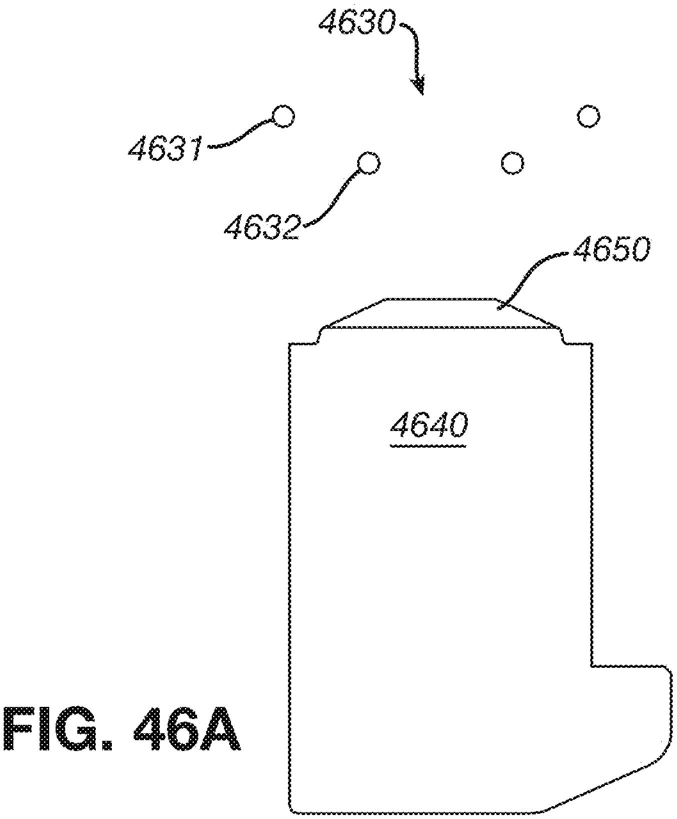
FIGS. 46A and 46B depict a driver and movable arbors according to one embodiment.
Figure 46B:
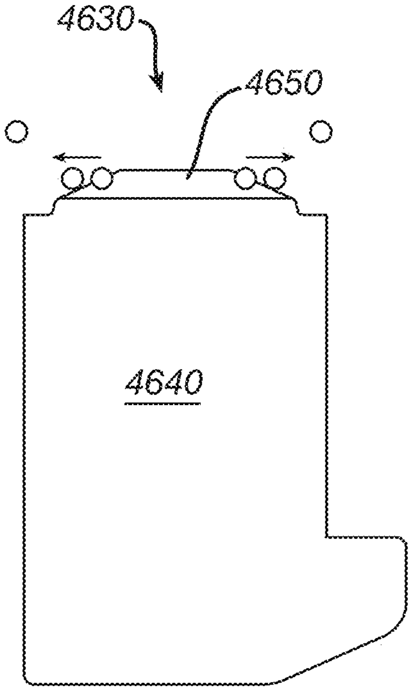
Figure 47A:
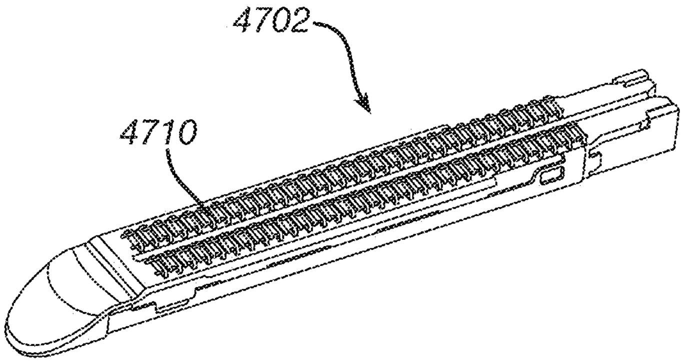
FIGS. 47A-C depict a staple cartridge having movable arbors according to one embodiment.
Figure 47B:
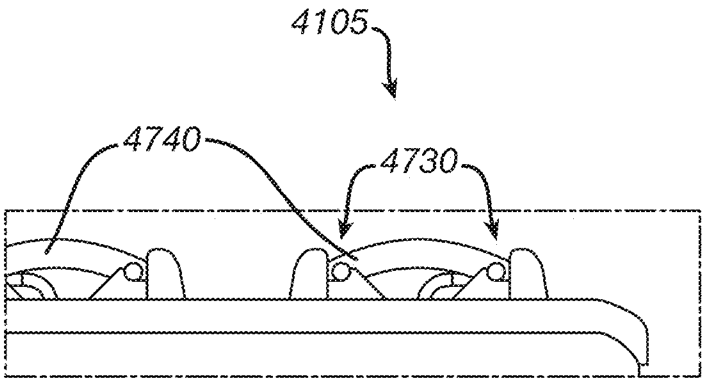
Figure 47C:
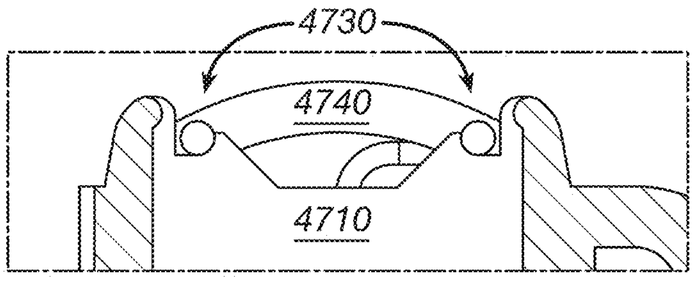

FIGS. 46 and 47 depict examples of dynamic or movable arbors according to one embodiment. In these embodiments, a staple cartridge includes a proximal end, a distal end, a tissue supporting deck, a staple cavity defined in the deck and configured to hold a staple, and a set of guide surfaces 4630, 4730 disposed adjacent the staple cavity. The staple cartridge also includes a driver configured to drive the staple out of the staple cavity and a sled movable from the proximal end to the distal end of the staple cartridge during a firing stroke to lift the driver.

The guide surfaces 4630, 4730, or arbors 4630, 4730, are configured to curl the staple during the firing stroke and may be arranged similar to the arrangements discussed and described above, such that the arbors are offset (both vertically and horizontally) from each other in or near the staple cavity, as shown in FIG. 46. The guide surfaces 4630, 4730, or arbors 4630, 4730 may include static arbors 4631, 4731 and dynamic or movable arbors 4632, 4732. The static arbors 4631, 4731 contribute to curling the staples, but may not deploy with the formed staples. As discussed below in more detail, the dynamic or movable arbors 4632, 4732 impact the radius of the curling staple depending on a position of the dynamic arbors 4632.

For example, a movement of the guide surfaces 4630, 4730 may cause a change in a curl radius of the staple during the firing stroke. The curl radius of the staple may be based on a position of the guide surfaces 4630, 4730 during the firing stroke. In some embodiments, the guide surfaces 4630, 4730 may be movable during the firing stroke in response to movement of a movable cartridge component. In one embodiment, the movable cartridge component is the driver 4640. In this case, a curl radius of the staple during the firing stroke is based on a vertical position of the driver 4640 in the staple cavity. In another embodiment, the movable cartridge component is a compressible member 4740 spanning between the guide surfaces 4730. In this case, a curl radius of the staple during the firing stroke is based on a compression force applied to the compressible member 4740. For example, the curl radius may be tighter when a higher compression force is applied, and the curl radius may be looser when a lower compression force is applied.

FIGS. 46A and 46B depict a driver and movable arbors according to one embodiment. In one embodiment, an instantaneous radius of a staple leg is a function of a vertical position of the driver 4640. For example, a staple cartridge includes a proximal end, a distal end, a tissue supporting deck, a staple cavity defined in the deck and configured to hold a staple, a set of guide surfaces 4630 disposed adjacent the staple cavity, a driver 4640 configured to drive the staple out of the staple cavity, and a sled movable from the proximal end to the distal end of the staple cartridge during a firing stroke to lift the driver 4640. FIG. 46A illustrates the driver 4640 in an initial, unfired position, and the FIG. 46B illustrates the driver 4640 mid-firing.

In this case, the guide surfaces 4630 are movable in response to movement of the driver 4640 and configured to curl the staple during the firing stroke at a non-constant curl radius. In this regard, a movement of the driver 4640 may cause a change in the curl radius of the staple during the firing stroke. In this case, the curl radius of the staple during the firing stroke is based on a vertical position of the driver 4640 in the staple cavity.

As shown in FIG. 46, the driver 4640 includes a cam 4650 disposed on a top surface of the driver 4640. In one embodiment, the cam 4650 is a ramp having inclined surfaces configured to engage and deflect the guide surfaces 4630. In one example, as the driver 4640 moves vertically within the staple cavity, the cam 4650 is configured to contact the guide surfaces 4630 and deflect the guide surfaces 4630 laterally within the staple cavity. This can be seen in FIG. 46B, where the arrows indicate movement of the lower arbors (the dynamic arbors 4632) outward toward the other arbors. As the guide surfaces 4630 deflect laterally based on contact with the cam 4650, the curl radius of the staple during the firing stroke tightens near the height of staple forming. In this way, the curl radius changes as a function of an angle of the inclined surfaces of the cam.

In other words, as the driver 4640 advances to lift the staple upward, the radius of curvature of the staple curl may change based on how much of the staple wire has been exposed, such as, for example, to achieve a tighter radius in the last portion of the firing stroke to cinch the staple legs tight. The change in radius is thus caused by a lateral deflection of the movable arbors 4632, which is caused by movement of the driver 4640 in the last portion of the firing stroke.

In one embodiment, the guide surfaces 4630 may be designed to move based on a factor encountered during clamping of tissue with jaws of an end effector including the staple cartridge described herein, or during firing of the staple cartridge. This allows for an adjustable radius of curl to the staple legs based on the factor encountered.

In another embodiment, arbor positions may be adjusted by leaf springs or another compressible member that move arbors laterally based on an amount of tissue compression in a given area. An initial position of the arbors may be set for a type of tissue, or for typical tissue thicknesses. This initial position of the arbors creates an initial bending radius of the staples. The arbors may be in contact with a series of leaf spring elements that cause the arbors to move laterally under high tissue load, and may be positioned to form the staple wire to different radii relative to the initial position. This may allow a customized curl for various staples along the length of the firing.

FIG. 47 depicts a staple cartridge having movable arbors according to one example. The staple cartridge 4702 of FIG. 47 includes a staple cavity 4710 configured to hold a staple, a set of guide surfaces 4730 disposed adjacent the staple cavity 4710, and a compressible member 4740 spanning between the guide surfaces 4730. In one embodiment, the compressible member 4740 is a leaf spring 4740. Other types of compressible members 4740 are possible.

In one example, the guide surfaces 4730 may be a pair of pins or rods spaced laterally apart from one another that extend along a length of the staple cartridge 4702 along a longitudinal axis parallel to a cut line. In one embodiment, each of the guide surfaces 4730 may be a single rod or pin that extends through or across a number of staple cavities 4710 from a proximal end to a distal end of the staple cartridge 4702. In another embodiment, each of the guide surfaces 4730 may only extend through or across a single staple cavity 4710.

The guide surfaces 4730, specifically the dynamic guide surfaces 4732, are movable in response to movement of the compressible member 4740. The guide surfaces 4730 are also configured to curl the staple during a firing stroke at a non-constant curl radius. For example, a movement of the compressible member 4740 causes a change in the curl radius of the staple during the firing stroke. In this case, the curl radius of the staple during the firing stroke is based on a compression force applied to the compressible member 4740. For example, the curl radius may be smaller when a higher compression force is applied, and the curl radius may be larger when a lower compression force is applied.

In the example of compressible member 4740 being a leaf spring 4740, as a compression force applied to the leaf spring 4740 increases, the leaf spring 4740 is configured to move the dynamic guide surfaces 4732 laterally within the staple cavity 4710. In an example, as the dynamic guide surfaces 4732 move laterally based on interaction with the leaf spring 4740, the curl radius of the staple during the firing stroke tightens.

In other words, as the staple cartridge 4702 is squeezed or compressed on different tissue thicknesses, the leaf spring 4740 compresses or flattens and moves the dynamic arbors 4732 laterally.

With this embodiment, tissue thickness does not need to be predetermined or known before setting the arbor positions, since the arbor positions change based on the compression force of the tissue. In this way, the dynamic arbors can accommodate varying tissue thicknesses during a firing stroke (i.e., "on the fly"). This also allows the radius of staple curling to change mid-firing stroke. In other words, as the staple cartridge encounters more pressure, such as increased tissue compression as a firing beam advances distally through the cartridge, the compressible member moves the arbors, which tightens the curl radius of the staples to bring the staple shape together (i.e., to finish the curl of the staple).

In one embodiment, as the dynamic arbors get pressed or moved outwardly, the arbors may then be free to release off of the top of the cartridge body. Thus, the staple cartridges described here may use guides/arbors of the types described in: U.S. patent application Ser. No. 18/781,551, entitled "Staple Cartridge Containing Forming Surfaces That Bend Staple Legs Upon Exiting"; U.S. patent application Ser. No. 18/781,578, entitled "Deployable Arbor Sets That Break Away From Staple Cartridge"; and U.S. patent application Ser. No. 18/781,583, entitled "Multi-Part Staple With Separate Legs And Crown To Facilitate Staple Release From Arbors," the disclosures of which are incorporated by reference herein, in their entirety. Therefore, the proposed staple cartridge described herein allows for adjusting the curl radius of a formed staple based on tissue thickness and also allows for releasing the arbors at the end of the firing stroke.

VIII. DEPLOYABLE ARBOR SETS THAT BREAK AWAY FROM STAPLE CARTRIDGE

In some embodiments, it may be desirable to use arbors, or arbor sets, that deploy or fire out with the formed staples. Deploying arbors with the staples provides a number of advantages. For example, deployable arbors solve the problem of advancing the staple crown past the arbors in order to exit the staple cavity. As described above, in order to contact and deform/curl staple legs, arbors are disposed in or near the staple cavity within the path of the staple being driven out of the staple cavity. If a single, continuous arbor spanned the staple pathway, the pathway would be blocked, and the crown of the staple would not be able to advance past the arbor to exit the staple cavity. In this case, the staple would remain in the staple cartridge and be ineffective. However, with deployable arbors, the driver is able to push both the staples and the arbors out of the staple cartridge.

Deployable arbors also provide the benefit of being able to act as a carrier or delivery mechanism and deliver different types of payloads to the tissue. For example, certain arbors sets, such as arbor sets described below that span the staple cavity, may contain an absorbable foam layer or cushion that acts as a buttress layer. The foam layer or cushion may help adjust compression on the tissue by adding compliance and allowing for varying tissue thickness. In this way, a cartridge can contain one size of staple that can handle different tissue thicknesses. In another example, rather than a foam layer, the arbor set that spans the staple cavity may contain and deliver a microbial or hemostatic pad, or other medicants such as antibiotics. In yet another example of potential payloads, if used with an absorbable staple such as an absorbable staple containing magnesium, deployable arbors may contain or be made from a metal or material (such as titanium, aluminum, steel, or iron) chosen to manipulate a galvanic reaction with a staple containing magnesium, such that the staple may absorb more quickly or slowly depending on the desired timing of the absorption. The deployable arbor may be made from non-absorbable metal (such as described above), or itself may be absorbable. Suitable absorbable materials could be metals or metal alloys that absorb over time (such as those containing magnesium) or polymers that when molded into the arbor shape have a hardness needed to curl wire when in place, such as vicryl or PDS (Polydioxanone) from Ethicon Inc.

Yet another advantage of the arbor sets disclosed herein is that the arbor sets themselves may act as tissue gripping features of staple cartridges that resist tissue flow or movement during firing. Arbor sets that act as tissue gripping features would allow staple cartridge bodies to be manufactured more simply, for example with a common flat tissue contacting surface, allowing multiple different types of arbor sets to be accommodated on common cartridge bodies, or even within the same cartridge.

The arbor sets described below may be molded and pressed into (e.g., friction fit, pressed fit, snap fit, or other interference-based-fit) the staple cartridge openings (i.e., staple pockets or cavities). Assembly of the arbor sets may occur after staples have been placed in the staple pockets of the staple cartridge. Each of the arbor sets described below is configured to deploy or fire out with the formed staples as the drivers reach the end of the firing stroke. The contact and force of the driver causes the arbor sets to break away from the cartridge. In this regard, the retention force keeping the arbor sets in place should exceed the force needed to curl the staple, but should be less than the force generated by the driver at the top of a sled ramp (i.e., the end of the firing stroke). In one example, the force needed to curl a staple may be around or about 2.5 pound-force (lbf) and the force generated by the driver at the end of a firing stroke may be around or about 10 lbf. Other ranges are possible. The terms "around" and "about" used in this section may refer to values within about 20% of the stated value. Thus, in one example, the force needed to curl a staple may be in the range of about 2 to 3 lbf and the force generated by the driver at the end of a firing stroke may be in the range of about 8 to 12 lbf.

FIGS. 48-53 depict deployable arbor sets according to different embodiments. In this regard, a staple cartridge includes a tissue supporting deck 4802 and a set of arbor inserts 4830, 5030 removably coupled to the deck 4802 adjacent a staple pocket 4810, the staple pocket 4810 being configured to hold a staple 4905. The set of arbor inserts 4830, 5030, described in detail below, may contain staple forming features, or arbors, the same as the staple forming features, guide surfaces, or arbors described above. In this way, the set of arbor inserts 4830, 5030 are configured to plastically deform the staple 4905 as the staple 4905 exits the staple pocket 4810 during a firing stroke.

The set of arbor inserts 4830, 5030 includes a frangible portion configured to removably hold the set of arbor inserts 4830, 5030 in place by a retention force. The frangible portion may be a surface, component, or adjunct of the arbor inserts 4830, 5030 connected to or abutting the deck 4802 of the staple cartridge. The frangible portion may be the part of the arbor inserts 4830, 5030 holding the arbor inserts 4830, 5030 in place in or on the deck 4802 of the staple cartridge. The retention force should be greater than a curling force needed to deform the staple 4905 so that the arbor inserts 4830, 5030 do not break away as soon as the staple begins to form (i.e., curl). The retention force should also be less than a driving force of a driver at the end of the firing stroke, otherwise the arbor inserts 4830, 5030 would not break away at the end of firing and remain on the cartridge deck 4802. This would result in the staples not deploying and being held by the arbor inserts 4830, 5030, which is not effective. Example curling and driving forces are discussed above.

In this regard, the frangible portion is configured to break away from the deck 4802 of the staple cartridge when a force greater than the retention force is exerted on the set of arbor inserts 4830, 5030, such that the set of arbor inserts 4830, 5030 is releasable upon exertion of the force. In one example, the force exerted on the set of arbor inserts 4830, 5030 may be between about 3 pound-force to about 6 pound-force. In another example, the force exerted on the set of arbor inserts 4830, 5030 may be between about 4 pound-force to about 8 pound-force.

Figure 48A:
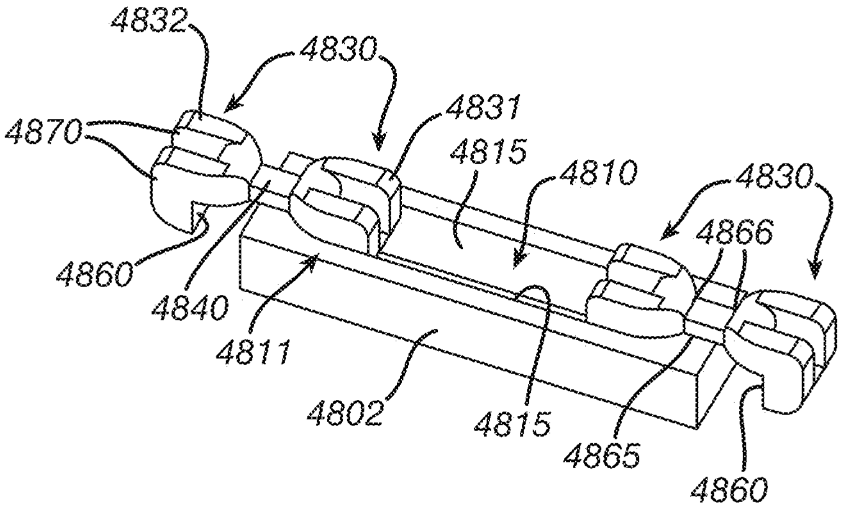
FIGS. 48A-C depict a set of arbor inserts according to one embodiment.
Figure 48B:
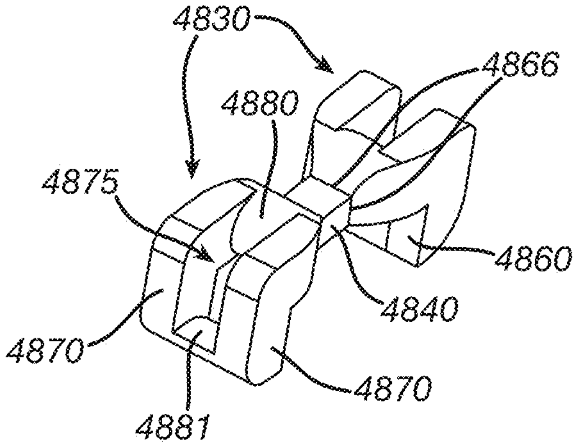
Figure 48C:
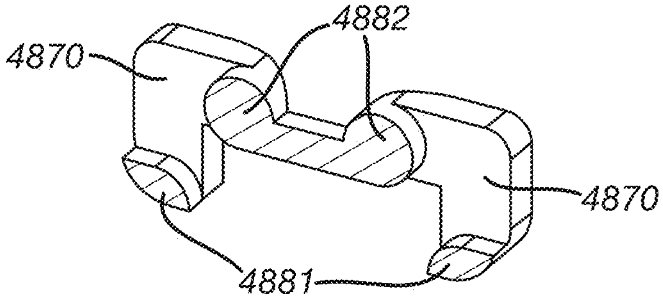

FIGS. 48A-C depict a set of arbor inserts according to one embodiment. The set of arbor inserts 4830 of FIGS. 48A-C can be removably coupled to a tissue supporting deck 4802 of a staple cartridge, such as the staple cartridges discussed above. The set of arbor inserts 4830 includes a first arbor insert 4831 disposed on the deck 4802 adjacent a first staple pocket 4810 configured to hold a first staple and a second arbor insert 4832 disposed on the deck 4802 adjacent a second staple pocket configured to hold a second staple, the second staple pocket being adjacent the first staple pocket 4810. The second staple pocket, while not shown in FIG. 48A, is axially aligned with the first staple pocket 4810 in the deck 4802. In other words, the portion of the second arbor insert 4832 extending out beyond the portion of the deck 4802 shown in FIG. 48A would be on the deck 4802 as well, and the downwardly extending portion would be disposed in the second staple pocket, such that a channel or pocket abutment surface 4860 of the second arbor insert 4832 abuts a sidewall of the second staple pocket.

Figure 49A:
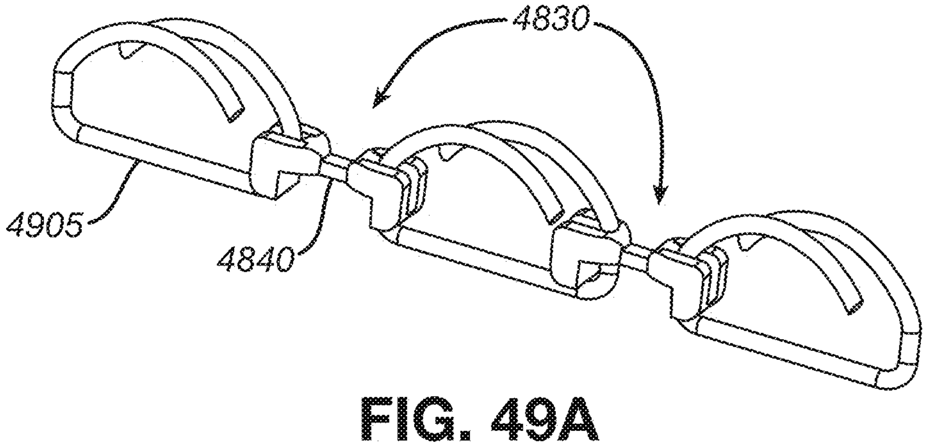
FIGS. 49A and 49B depict adjacent sets of arbor inserts in a connected state and broken state according to one embodiment.
Figure 49B:
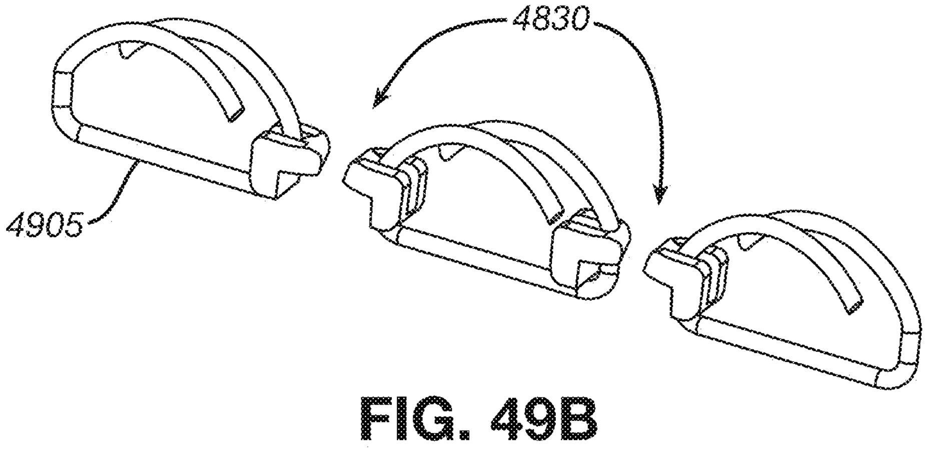

In some embodiments, it may be desirable to have adjacent sets of arbor inserts 4830 connected, which may result in connected rows of staple pockets. For example, in one embodiment, the staple 4905 is plastically deformed into a formed staple 4905 as the staple 4905 exits the staple pocket 4810 during the firing stroke, and the set of arbor inserts 4830 is configured to axially connect with another set of arbor inserts 4830 of an axially adjacent staple pocket 4810, such that when both sets of arbors 4830 are released with respective formed staples 4905, the respective formed staples 4905 are connected. Connections of arbor inserts 4830 (e.g., adjacent arbor inserts 4830) may be done in a way that allows the connection between staple pockets to be frangible (e.g., breakable), or stay together in a linked chain, depending on the desired tissue effect. For example, linking arbor inserts 4830 in a chain may help sealing of the tissue, as well as spreading compression forces. FIGS. 49A and 49B depict adjacent sets of arbor inserts 4830 connected and broken apart according to one example.

In this regard, the set of arbor inserts 4830 also includes a coupler 4840 axially connecting the first arbor insert 4831 and the second arbor insert 4832. A bottom surface 4865 of the coupler 4840 may abut and be connected to a top surface of the deck 4802. In one example, the coupler 4840 may be the frangible portion discussed above. For example, when a force is exerted on the set of arbor inserts 4830, the coupler 4840 may break away from the deck 4802, thus freeing the arbor inserts 4830 from the staple cartridge. In one example, as shown in FIG. 49A, the coupler 4840 may stay connected to the first arbor insert 4831 and the second arbor insert 4832, thus linking the formed stapes formed in respective first and second staple pockets. In other examples, the coupler 4840 may be designed to break away from the first arbor insert 4831 and the second arbor insert 4832, such that the first arbor insert 4831 and the second arbor insert 4832 break away from the deck 4802 of the staple cartridge individually. In one example, the coupler 4840 may break away along surfaces abutting the deck 4802 (e.g., bottom surface 4865 of the coupler 4840) and insert abutment surfaces 4866 abutting the first arbor insert 4831 and the second arbor insert 4832, such that the coupler 4840 becomes an independent piece. In another example, the coupler 4866 may stay connected to the deck 4802 while breaking at the insert abutment surfaces 4866 abutting the first arbor insert 4831 and the second arbor insert 4832. In this example, couplers 4840 would be left behind on the deck 4802 of the staple cartridge. In yet another example, as shown in FIG. 49B, the coupler 4840 may be designed to snap or break along the bottom surface 4865 of the coupler 4840 (to release from the cartridge deck 4802) and also break apart in half, such that a first half of the coupler 4840 remains attached to the first arbor insert 4831 and a second half of the coupler 4840 remains attached to the second arbor insert 4832.

As mentioned above, the set of arbor inserts 4830 may contain staple forming features, or arbors, the same as the staple forming features, guide surfaces, or arbors described above. In this way, the first arbor insert 4831 is configured to plastically deform a staple leg of the first staple as the first staple exits the first staple pocket 4810 during a firing stroke and the second arbor insert 4832 is configured to plastically deform a staple leg of the second staple as the second staple exits the second staple pocket during the firing stroke.

Referring back to FIGS. 48A-C, each arbor insert 4830 includes a pair of opposing L-shaped sidewalls 4870 which can define a channel 4875, or arbor channel 4875, therebetween. The opposing sidewalls 4870 of the arbor inserts 4830 are connected at both ends (i.e., ends of the "L") by an arbor 4880 or staple forming feature 4880. The arbor inserts 4830 are configured to receive a staple leg in the arbor channel 4875 between the opposing sidewalls 4870 and between the two staple forming features 4880. In this way, arbor inserts 4830 have a shape and design that accommodate arbors 4880 and staples. In other words, once each arbor insert 4830 is press fit into respective ends of respective staple pockets, a staple leg can be driven upward and into the arbor inserts 4830, specifically into the arbor insert channel 4875 between the sidewalls 4870 and the two staple forming features 4880. The staple forming features 4880 of the arbor inserts 4830, best shown in the cross sectional image of the arbor insert 4830 in FIG. 48C, may be the same as the staple forming features, guide surfaces, or arbors described above. In this regard, as a staple leg passes through the channel 4875 in the arbor inserts 4830, the staple forming features 4880 deform (i.e., bend or curl) the staple leg. Specifically, as best seen in the cross sectional image of the arbor insert 4830 in FIG. 48C, as a staple leg enters the channel 4875 the staple leg passes a lower arbor 4881 of the staple forming features 4880 and continues rising upward (vertically) through the channel 4875 until the staple leg contacts an upper arbor 4882 of the staple forming features 4880. At this point, the upper arbor 4882 forces the staple leg to bend away from the upper arbor 4882. As the staple leg bends away from the upper arbor 4882, the staple leg is forced to curl around the lower arbor 4881. This continues until the crown of the staple contacts the bottom of the lower arbor 4881, at which point the arbor insert 4830 breaks away from the cartridge deck 4802. In some embodiments, the position, orientation, and angles of the staple forming features 4880 of the arbor inserts 4830 also allow for the staple legs to be deformed out of plane, such that three-dimensional (3D) staples can be formed. Examples are shown in FIGS. 49, 51, and 52.

In lieu of, or in addition to, the frangible arrangement described above, the set of arbor inserts 4830 may be removable by way of friction fit or interference fit connections with the staple cartridge. For example, in one embodiment, the first arbor insert 4831 is configured to fit within a first end 4811 of the first staple pocket 4810 and be resiliently biased against sidewalls 4815 of the first staple pocket 4810 to provide a friction fit or any type of interference fit between the first arbor insert 4831 and the sidewalls 4815 of the first staple pocket 4810. Similarly, the second arbor insert 4832 is configured to fit within a first end of the second staple pocket and be resiliently biased against sidewalls of the second staple pocket to provide a friction fit between the second arbor insert 4832 and the sidewalls of the second staple pocket. In this embodiment, the friction fit between the first arbor insert 4831 and the sidewalls of the first staple pocket 4810 provides a first retention force for removably holding the first arbor insert 4831 in place, and the friction fit between the second arbor insert 4832 and the sidewalls of the second staple pocket provides a second retention force for removably holding the second arbor insert 4832 in place. In this way, the first arbor insert 4831 and the second arbor insert 4832 are configured to break away from the deck 4802 of the staple cartridge when a force greater than the first retention force and the second retention force is exerted on the first arbor insert 4831 and the second arbor insert 4832, respectively.

This type of arrangement also allows the set of arbor inserts 4830 to be released with the formed staples and still connected together, as shown in FIG. 49A. For example, the first staple is plastically deformed into a first formed staple as the first staple exits the first staple pocket 4810 during the firing stroke. The second staple is plastically deformed into a second formed staple as the second staple exits the second staple pocket during the firing stroke. Thus, when the first arbor insert 4831 and the second arbor insert 4832 are released with respective first and second formed staples, the respective first and second formed staples are connected via the first and second arbor inserts 4831, 4832 and the coupler 4840.

Figure 50:
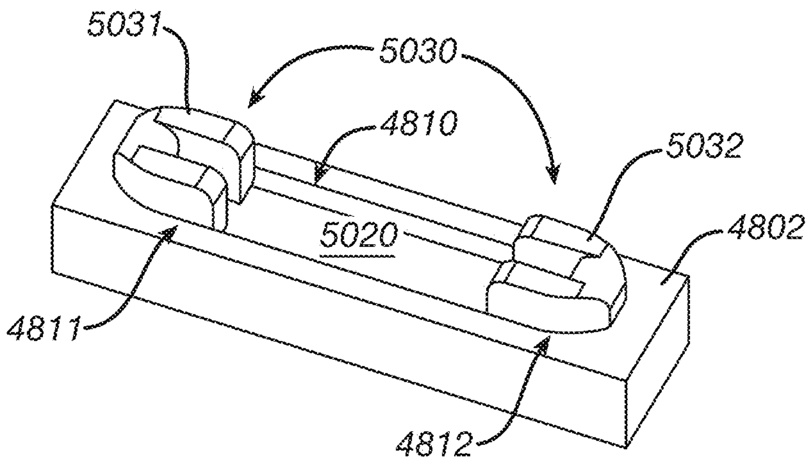
FIG. 50 depicts a set of arbor inserts according to one embodiment.

FIG. 50 depicts a set of arbor inserts according to one embodiment. The set of arbor inserts 5030 of FIG. 50 can be removably coupled within a staple pocket 4810 of tissue supporting deck 4802 of a staple cartridge, such as the staple cartridges discussed above. The staple pocket 4810 is configured to hold a staple 4905. The set of arbor inserts 5030 includes a first arbor insert 5031 disposed at a first end 4811 of the staple pocket 4810 and a second arbor insert 5032 disposed at a second end 4812 of the staple pocket 4810. The set of arbor inserts 5030 also includes a platform 5020 spanning the staple pocket 4810 and connecting the first arbor insert 5031 and the second arbor insert 5032. In this way, the individual arbor inserts 5031, 5032 can be the same as arbor inserts 4031, 4032 described above, except instead of two arbor inserts 4031, 4032 from adjacent staple pockets being connected at the top end, this embodiment connects two arbor inserts 5031, 5032 of the same staple pocket 4810 with a platform 5020 in between. In other words, the set of arbor inserts 5030 includes a first arbor insert 5031, a second arbor insert 5032, and a platform 5020 connecting lower ends of the first arbor insert 5031 and the second arbor insert 5032.

The combined cap formed by the arbor inserts 5030 and platform 5020 may be press fit or interference fit within the staple pocket 4810, such that the cap is removably coupled to the deck 4802. For example, in one embodiment, the set of arbor inserts 5030 is configured to fit within the staple pocket 4810 and be resiliently biased against sidewalls of the staple pocket 4810 to provide a friction fit between the set of arbor inserts 5030 and the sidewalls of the staple pocket 4810. In this case, the friction fit between the set of arbor inserts 5030 and the sidewalls of the staple pocket 4810 provides a retention force for removably holding the set of arbor inserts 5030 in place. The set of arbor inserts 5030 is configured to break away from the deck 4802 of the staple cartridge 4810 during the firing stroke when a force greater than the retention force is exerted on the set of arbor inserts 5030.

In other examples, similar to those described above, the cap may contain frangible portions that are designed to break away from the deck 4802 when a force applied to the cap is greater than a retention force holding the cap within the staple pocket 4810. For example, the bottom surfaces of the top part of the L-shaped portions of the arbor inserts 5030 that extend away from the platform 5020 may contain a frangible portion or surface that rests on the cartridge deck 4802 when inserted into the staple pocket 4810.

Figure 51A:
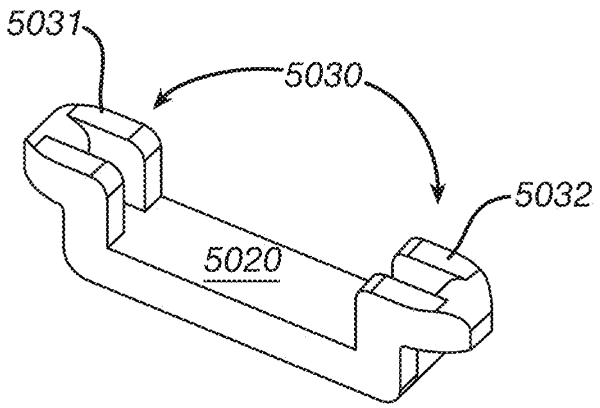
FIGS. 51A-C depict a set of arbor inserts used to curl a staple according to one embodiment.
Figure 51B:
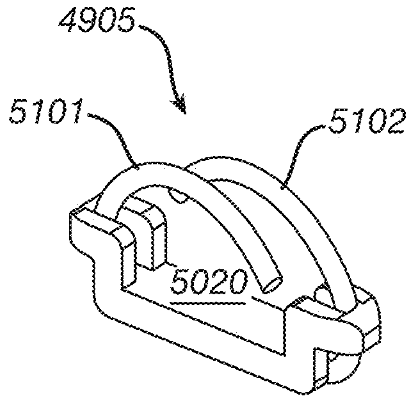
Figure 51C:
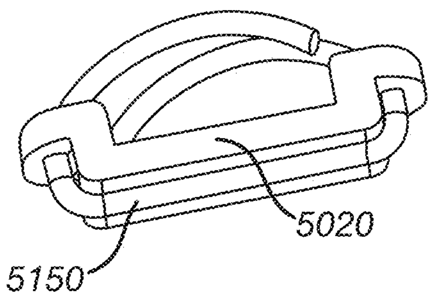

FIGS. 51A-C depict a set of arbor inserts used to curl a staple according to one embodiment. Similar to above, the first arbor insert 5031 is configured to plastically deform a first staple leg 5101 of the staple 4905 as the staple 4905 exits the staple pocket 4810 during a firing stroke, and the second arbor insert 5032 is configured to plastically deform a second staple leg 5102 of the staple 4905 as the staple 4905 exits the staple pocket 4810 during the firing stroke. As shown, 3D staples with offset formed staple legs may also be formed using the arbor sets disclosed herein. At the end of the firing stroke, the staple legs 5101, 5102 have been driven up the staple pocket 4810 and curled by the set of arbors 5030. The staple crown 5150 comes into contact with the bottom surface of the platform 5020 and, as the driver imparts a force upward at the end of the firing stroke, the force is transmitted through the crown 5150 to the platform 5020, which is greater than the retention force, such that the platform 5020 and formed staple breaks away or releases from the cartridge deck 4802.

Figure 52A:
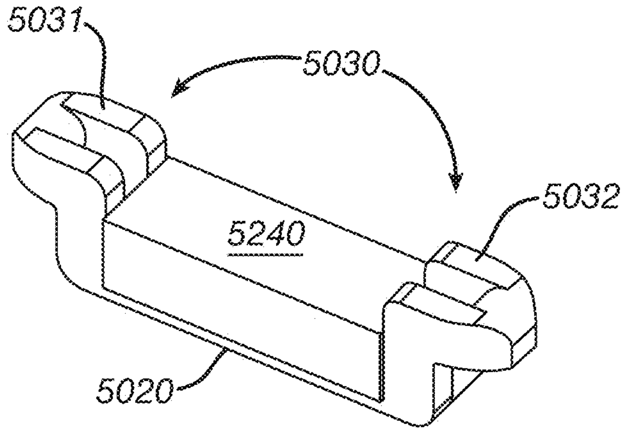
FIGS. 52A and 52B depict a set of arbor inserts and platform as a carrier according to one embodiment.
Figure 52B:
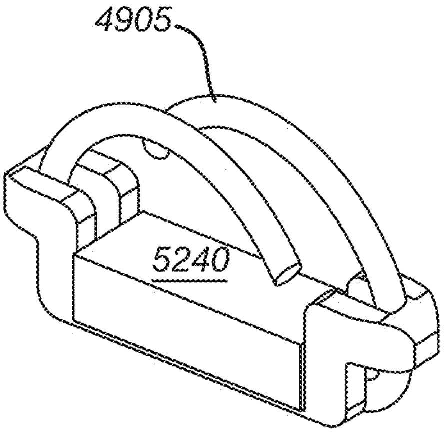

As shown in FIGS. 50-52, the platform 5020 spans the staple pocket 4810 and thus the space within the staple pocket 4810 over the crown 5150 of the staple 4905. In this regard, the set of arbor inserts 5030 together with the platform 5020 creates a delivery mechanism or carrier that can be used to deliver or carry objects in the space on and above the platform 5020 to the tissue as the arbor inserts 5030 and platform 5020 are deployed. For example, in some embodiments, the platform 5020 is configured to carry an absorbable cushion 5240, foam, pad, or other medicants, as shown in FIGS. 52A and 52B.

FIGS. 52A and 52B depict a set of arbor inserts and platform as a carrier according to one embodiment. In one example, the absorbable cushion 5240 may be held in place by the staple 4905. In another example, the platform 5020 may carry a material or substance to assist with wound closure, such that the arbor inserts 5030 and platform 5020 together with the material are deployed together as a type of pledget. Since the payload being held in place and delivered by the arbor inserts 5030 and platform 5020 may contain chemicals or materials that may react to other substances, the surfaces of the arbor inserts 5030 and platform 5020, or at least the surfaces of the staple forming features or arbors in respective arbor inserts 5031, 5032, may be hardened or coated to maintain surface integrity. In one embodiment, an absorbable cushion 5240, foam, pad, or other medicants may be disposed on the platform 5020, such that when the set of arbor inserts 5030 breaks away from the deck 4802 of the staple cartridge into tissue upon completion of the firing stroke, the absorbable cushion 5240, foam, pad, or other medicants are delivered to the tissue.

The absorbable foam layer or cushion 5240 may also act as a buttress layer. The cushion 5240 may help adjust compression on the tissue by adding compliance and allowing for varying tissue thickness. The absorbable foam layer may be constructed of a foam, a matrix, a cushion, an adjunct, or other elastic construct that can densify over time, including materials described in U.S. Pat. No. 10,966,722 entitled "Adjunct Materials And Methods Of Using Same In Surgical Methods For Tissue Sealing," issued Apr. 6, 2021 or adjuncts described in U.S. Pub. No. 2023/0301674 entitled "Tissue Cushion Adjunct For Surgical Stapler End Effector," published Sep. 28, 2023. In one example, the staple 4905 is plastically deformed into a formed staple 4905 as the staple 4905 exits the staple pocket 4810 during the firing stroke. Tissue is captured within the formed staple 4905, and in one example the compressible cushion or layer 5240 produces at least 8 g/mm^2 of pressure to the tissue captured within the formed staple 4905. However, in other examples, the cushion may produce significantly higher pressure values to the tissue captured within the formed staple 4905 depending on the type and thickness of the tissue being targeted.

Since the arbor sets described above may be positioned uniformly over all staple cavities or over select staple cavities of the staple cartridge, the amount of modularity, interchangeability and potential options is improved. For example, a staple cartridge may use a same arbor set for all staple cavities to carry the same payload to the tissue, or may use different arbor sets for different cavities to carry different payloads to the tissue. In another example, some arbor sets may carry medicants while others carry foam layers. Further, the arbor or guide surface configurations may be different for each arbor set. In this way, some arbor sets may form three-dimensional (3D) staples and be positioned away from a cutline, for example, while other arbor sets may make normal or tighter-radiused staples and be positioned near the cutline, for example. The 3D staples mentioned above may be the type of staples as disclosed in U.S. patent application Ser. No. 18/781,558, entitled "Staple Shape Control Using Selective Bending Segments of Staples," filed on Jul. 23, 2024, the disclosure of which is incorporated by reference herein, in its entirety.

Figure 53:
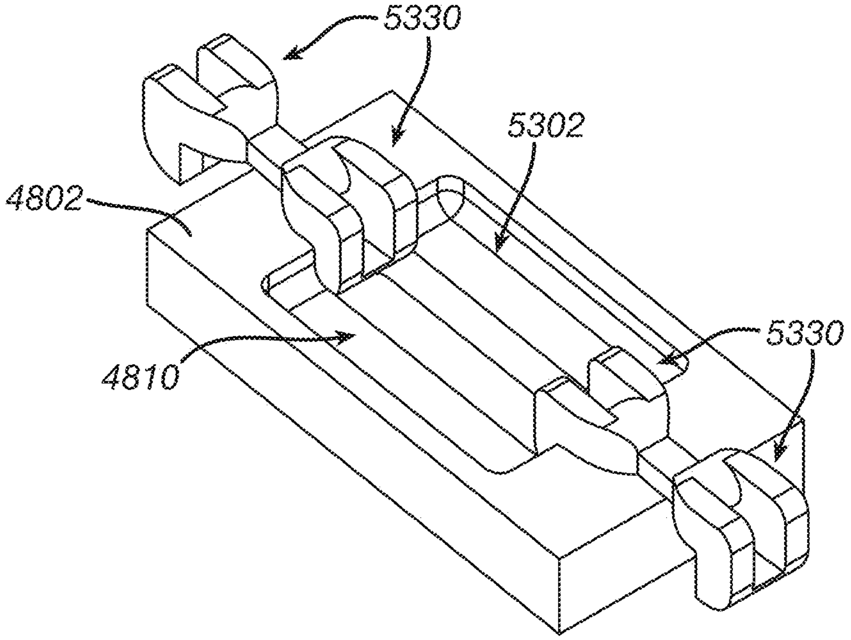
FIG. 53 depicts a set of arbor inserts and a staple pocket opening with a relief according to one embodiment.

FIG. 53 depicts a set of arbor inserts 5330 and a staple pocket opening with a relief according to one embodiment. In one example, the deck 4802 of a staple cartridge may include a surface relief 5302 around the opening of the staple pocket 4810. The surface relief 5302 may allow tissue to compress down into the surface relief 5302, effectively causing the tissue gap to be larger than without the surface relief 5302. The surface relief 5302 may also result in the crown of the formed staple to be closer to the surface of the opening (i.e., exit) of the cartridge pocket 4810. The staple form may not be impacted since the forming surfaces (e.g., arbors or staple forming features or surfaces) and the legs of the staple are still in their fixed positions. The staple legs would still be completely surrounded during staple forming so malform occurrence is low.

Figure 54:
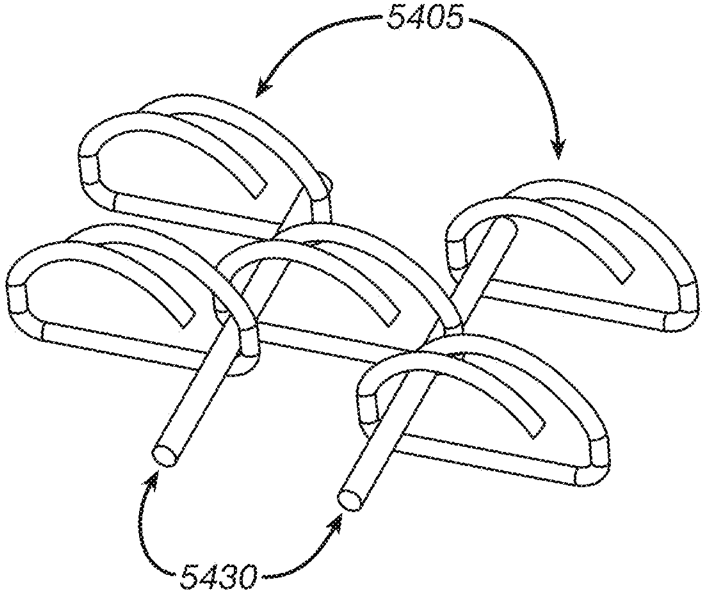
FIG. 54 depicts a set of arbors according to one embodiment.

FIG. 54 depicts a set of arbors according to one example. In the example shown in FIG. 54, a set of arbors 5430 include rods or pins as described above that span or straddle multiple staple pockets or rows of staple. The set of arbors 5430 may be deployable along with the staples 5405. In this example, the set of arbors 5430 may contain or be made from a specific material designed to cause or produce a certain reaction with the formed staples 5405. For example, when the set of arbors 5430 releases with the staples 5405 into tissue upon completion of a firing stroke, the material in the set of arbors 5430 may produce a galvanic reaction with the staples 5405. Another advantage to the configuration shown in FIG. 54 is that this staple and arbor arrangement, when deployed connected, spreads out the compression load and becomes a matrix rather than individual rows of staples.

The set of arbor inserts 4830, 5030, 5430 described above may be made from a bioabsorbable material. In one example, the set of arbor inserts 4830, 5030, 5430 described above may be made from an absorbable polymer so that they degrade quickly after firing. The set of arbor inserts 4830, 5030, 5430 may also be made from titanium or a titanium alloy like the staples, or magnesium that could also degrade. In some examples, if the set of arbor inserts 4830, 5030, 5430 are used with an absorbable staple, the material of the set of arbor inserts 4830, 5030, 5430 may be chosen to manipulate a reaction with the metal or material of the staple. Some materials that may produce such reactions include titanium, steel, aluminum, or iron.

For example, when the staple 4905 includes a magnesium staple, the set of arbor inserts 4830, 5030, 5430 may contain or be made from a material, such that when the set of arbor inserts 4830, 5030, 5430 releases with the staples 4905 into tissue upon completion of a firing stroke, the material produces a galvanic reaction with the magnesium staple.

In one example, the set of arbor inserts 4830, 5030, 5430 contains or is made from a chemical substance, such that when the set of arbor inserts 4830, 5030, 5430 releases with the staples 4905 into tissue upon completion of the firing stroke, the chemical substance reacts with the staples 4905 to influence a speed of absorption of the staples 4905 in the tissue. In one embodiment, the chemical substance inhibits matrix metalloproteinase (MMP) to promote healing.

As mentioned above, the arbor inserts 4830, 5030, 5430 described above may also function as tissue gripping features of staple cartridges. For example, as shown in the figures, when the arbor inserts 4830, 5030, 5430 are press fit, for example, into respective staple pockets, a top portion of the pair of opposing L-shaped sidewalls 4870 is raised above the cartridge deck 4802. These raised or protruding portions may, after coming into contact with tissue, resist tissue flow or tissue movement over time. In this case, the retention force holding the arbor inserts 4830, 5030, 5430 in place would need to be greater than the force experienced by gripping tissue, so that the arbor inserts 4830, 5030, 5430 do not pull out or break away when they come into contact with tissue.

Yet another advantage of the arbor sets disclosed herein is that the arbor sets themselves may act as tissue gripping features of staple cartridges that resist tissue flow or movement during firing. Arbor sets that act as tissue gripping features would allow staple cartridge bodies to be manufactured more simply.

IX. MULTI-PART STAPLE WITH SEPARATE LEGS AND CROWN TO FACILITATE STAPLE RELEASE FROM ARBORS

As discussed above, staple forming surfaces or features, such as arbors, may be fixed (i.e., static) and disposed on an inner wall or surface of a staple cartridge pocket or opening. The arbors may be positioned at or near the exit of the cartridge pocket (also referred to as a staple pocket) such that the staple legs of a staple are curled by the arbors as the staple legs exit the staple pocket. There are advantages of having static staple forming features, or arbors. For instance, having arbors being integral with the cartridge may allow to use molds, especially if the arbors are designed to be on an edge of feature that is already being molded. This would simply the manufacturing of the cartridges to contain arbors.

However, with static arbors there is problem of advancing the staple crown past the arbors in order to exit the staple cavity. As described above, in order to contact and deform (e.g., curl) staple legs, arbors are disposed in or near the staple cavity within the path of the staple being driven out of the staple cavity. If a single, continuous arbor spanned the staple pathway, the pathway would be blocked, and the crown of the staple would not be able to advance past the arbor to exit the staple cavity. In this case, the staple would remain in the staple cartridge and be ineffective. In many cases, as shown and described above, while a width of the staple crown may be narrower than the uppermost or outer arbors, the lower or inner arbors are the ones that interfere with the crown bypassing those arbors.

A staple cartridge having the staple and arbor arrangement described below solves this problem by using arbors and a multi-part, or deconstructed, staple with separate legs and crown pieces to facilitate staple release from the arbors. In this embodiment, the staple crown is located above the lower arbors so that as the staple legs curl, the lower or inner arbors do not get trapped inside the staple. In another embodiment, the crown piece includes staple forming features, such as apertures in the form of curved passageways, that initiate staple curling as the staple legs pass through the apertures of the crown piece. In this case, additional arbors may or may not be necessary.

Figure 55:
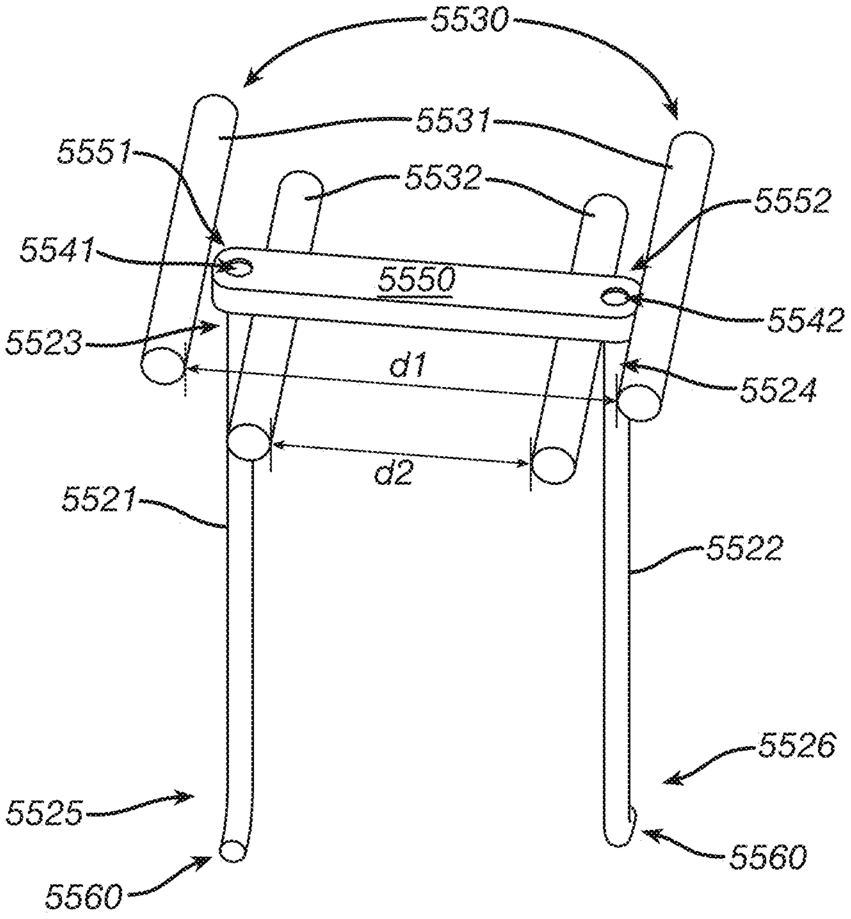
FIG. 55 depicts a perspective view of a set of arbors and a multi-part staple according to one embodiment.

FIG. 55 depicts a perspective view of a set of arbors and a multi-part staple according to one embodiment. As shown in FIG. 55, the multi-part staple (also referred to herein as a deconstructed staple) has several components that get assembled during a firing stroke to form a final formed staple using arbors on or in the staple cartridge. The staple cartridge includes a set of arbors 5530 disposed adjacent a staple pocket having an opening, the set of arbors 5530 including an upper set of arbors 5531 and a lower set of arbors 5532 disposed vertically below the upper set of arbors 5531. The set of arbors 5530 may be static arbors and may be the same type of arbors as described above. The staple cartridge also includes a multi-part staple including a first leg or first staple leg portion 5521, a second leg or second staple leg portion 5522, and a crown portion 5550 (also referred to herein as a pledget). In one example, the first and second staple leg portions 5521, 5522 may each be a single, cylindrical staple wire. The crown portion 5550 is disposed vertically between the upper set of arbors 5531 and the lower set of arbors 5532. In other words, the crown portion 5550 sits on top of, or is supported by, the lower set of arbors 5532.

The crown portion 5550 includes a first aperture 5541 disposed at a first end 5551 of the crown portion 5550 and a second aperture 5542 disposed at a second end 5552 of the crown portion 5550. The first aperture 5541 is configured to receive the first staple leg portion 5521 and the second aperture 5542 is configured to receive the second staple leg portion 5522.

Figure 56A:
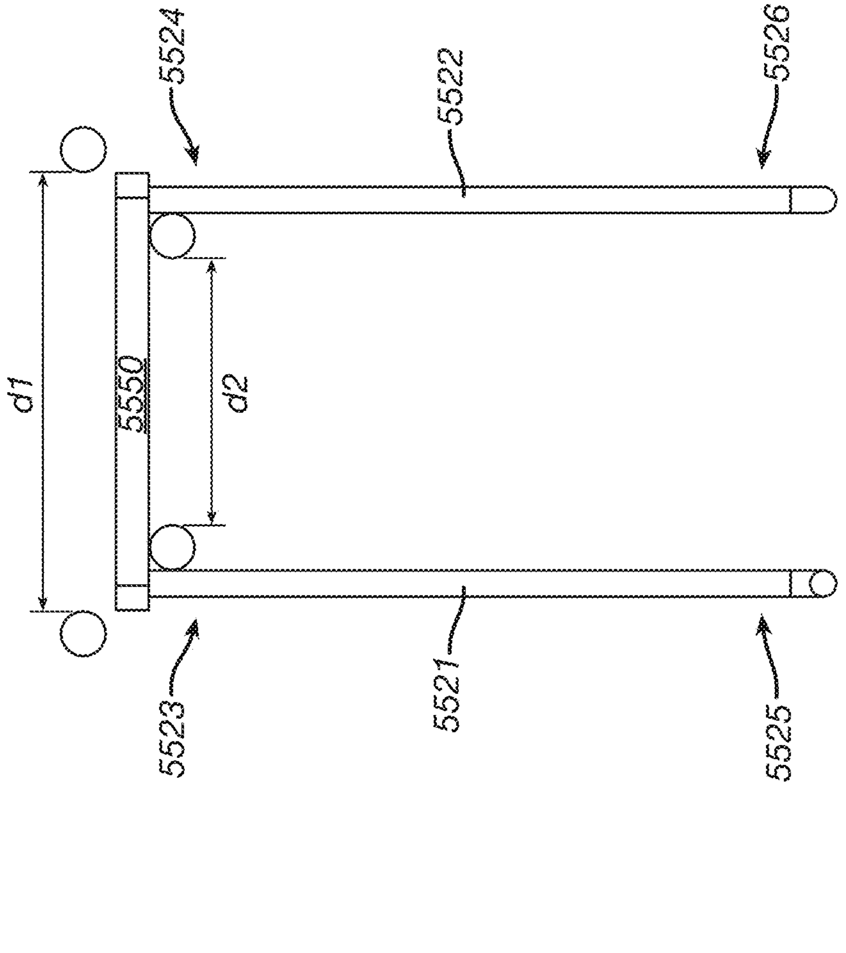
FIGS. 56A and 56B depict a side view of the set of arbors and the multi-part staple of FIG. 55 according to one embodiment.
Figure 56B:
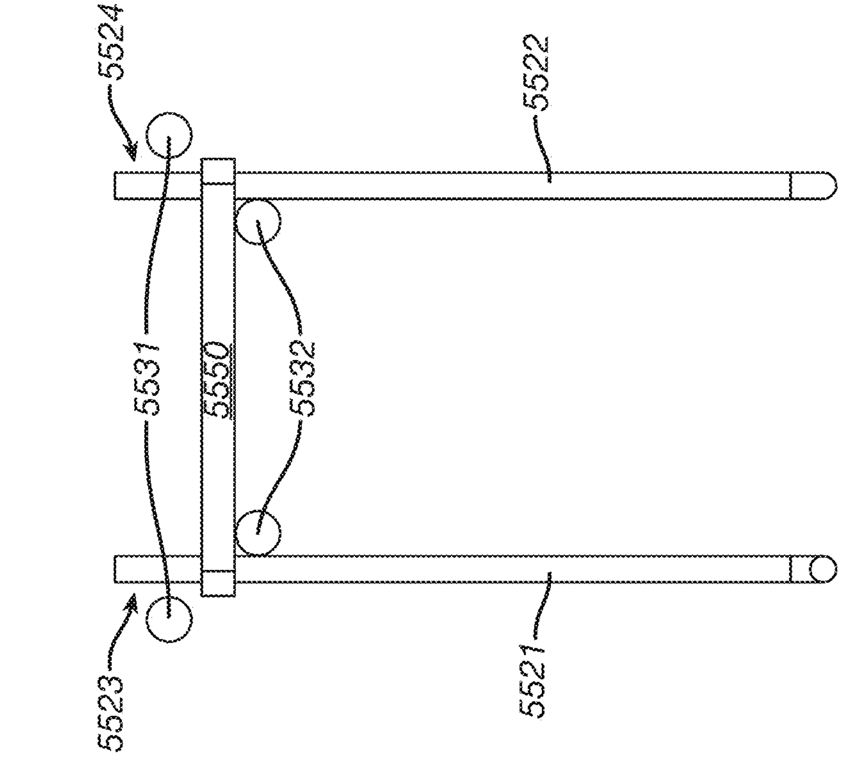

FIGS. 56A and 56B depict a side view of the set of arbors and the multi-part staple of FIG. 55 according to one embodiment. In one example, the set of arbors 5530 may be pre-formed into the staple pocket. To load the staples, the crown portion 5550 may be placed on top of the lower set of arbors 5532 and then the first staple leg portion 5521 and the second staple leg portion 5522 may be guided through the bottom of the staple pocket and into the first and second apertures 5541, 5542. Such arrangements allow the staple pockets to have two discrete paths, one for each leg. In other words, rather than a typical staple pocket that holds a traditional unformed staple, the multi-part stable described herein would only need two holes in the bottom of the staple cartridge to be received therein. In this example, the staple legs 5521, 5522 can be inserted into respective openings in the staple cartridge, where the respective openings can be configured to guide the staple legs 5521, 5522 into the apertures 5541, 5542 of the crown portion 5550.

As shown in FIG. 56A, a first end 5523 of the first staple leg portion 5521 and a first end 5524 of the second staple leg portion 5522 is configured to pass through the first aperture 5541 and the second aperture 5542 of the crown portion 5550, respectively, during the firing stroke. During the firing stroke, the first staple leg portion 5521 and the second staple leg portion 5522 are driven upwards between the lower set of arbors 5532, through the first and second apertures 5541, 5542, respectively, and then between the upper set of arbors 5531. This is shown in FIG. 56B. FIGS. 56A and 56B are drawn for illustration purposes, and the positions of the arbors, for example, are not to scale.

As shown in FIGS. 55 and 56, in one embodiment, arbors of the upper set of arbors 5531 are spaced apart by a first distance d1 and arbors of the lower set of arbors 5532 are spaced apart by a second distance d2 less than the first distance d1.

Figure 57:
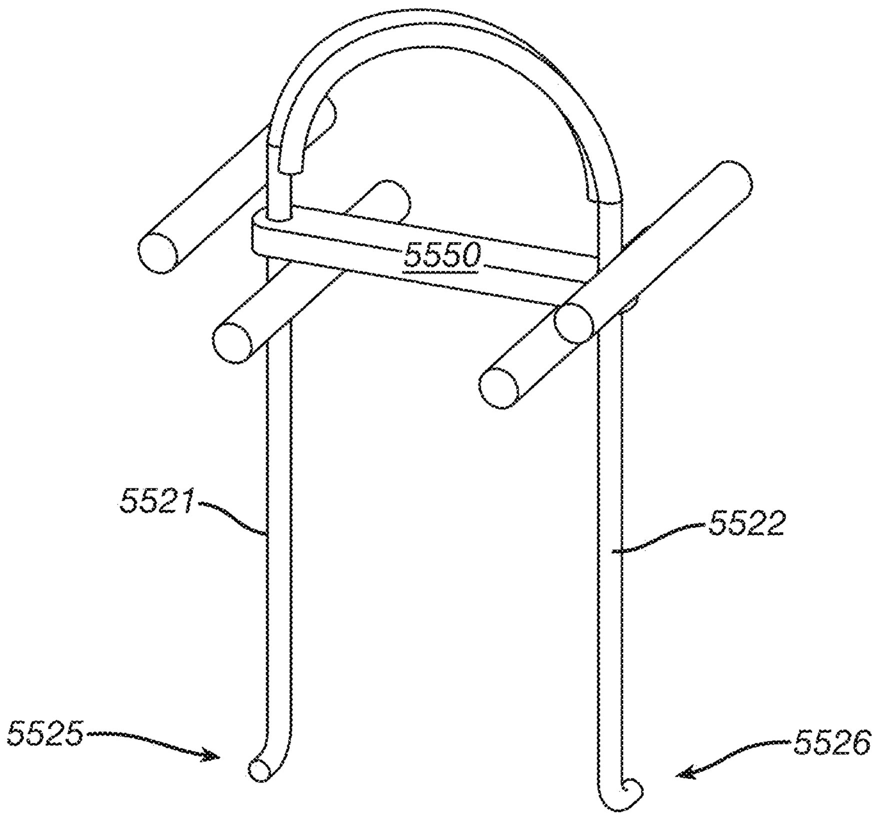
FIG. 57 depicts a perspective view of a set of arbors curling a multi-part staple according to one embodiment.

FIG. 57 depicts a perspective view of a set of arbors curling a multi-part staple according to one embodiment. As shown in FIG. 57, the set of arbors 5530 are configured to curl the first staple leg portion 5521 and the second staple leg portion 5522 as the first staple leg portion 5521 and the second staple leg portion 5522 exit the staple pocket at the opening during a firing stroke. In some cases, only one set of the set of arbors 5530 is configured to curl the staple legs 5521, 5522, such as the upper set of arbors 5531. In this case, as described in more detail below, the first and second apertures 5541, 5542 themselves may act as lower arbors, where each aperture 5541, 5542 includes surfaces able to react to load and help bend the first staple leg portion 5521 and the second staple leg portion 5522. In other words, each aperture 5541, 5542 may have a surface similar to the lower arbors 4881 shown in the cross sectional view at the bottom of FIG. 48, such that as the staple leg portions 5521, 5522 exit the apertures 5541, 5542 and contact the upper set of arbors 5531, the staple leg portions 5521, 5522 bend away from the upper set of arbors 5531 and the curl over the surfaces of the apertures 5541, 5542.

Referring back to FIG. 55, in various embodiments, a second end 5525 of the first staple leg portion 5521 includes a feature 5560 to prevent the second end 5525 (or a portion thereof) of the first staple leg portion 5521 from passing through the first aperture 5541 of the crown portion 5550 during the firing stroke. Similarly, a second end 5526 of the second staple leg portion 5522 includes a feature 5560 to prevent the second end 5526 (or a portion thereof) of the second staple leg portion 5522 from passing through the second aperture 5542 of the crown portion 5550 during the firing stroke. In this way, once the first staple leg portion 5521 and the second staple leg portion 5522 are almost completely driven out of the staple pocket, the features 5560 of the second ends 5525, 5526 of the first and second staple legs 5521, 5522 contact or engage the crown portion 5550, more specifically the bottom surface of the crown portion 5550, to facilitate interlocking between the staple legs 5521, 5522 and to ensure the crown portion 5550 is driven out of the staple pocket with the staple legs 5521, 5522. In this regard, the crown portion 5550 releases with the first staple leg portion 5521 and the second staple leg portion 5522 into tissue upon completion of the firing stroke. In other words, the crown portion 5550 or pledget 5550 is configured to release with the first leg 5521 and the second leg 5522 upon completion of the firing stroke. In this way, the lower set of arbors 5532 do not get trapped inside the formed staple.

Figure 58A:
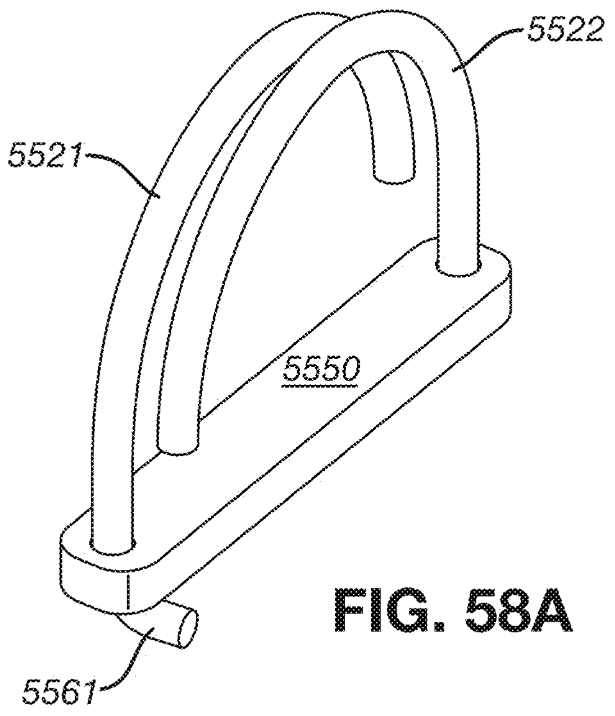
FIGS. 58A and 58B depict a front view and perspective view of a formed multi-part staple according to one embodiment.
Figure 58B:
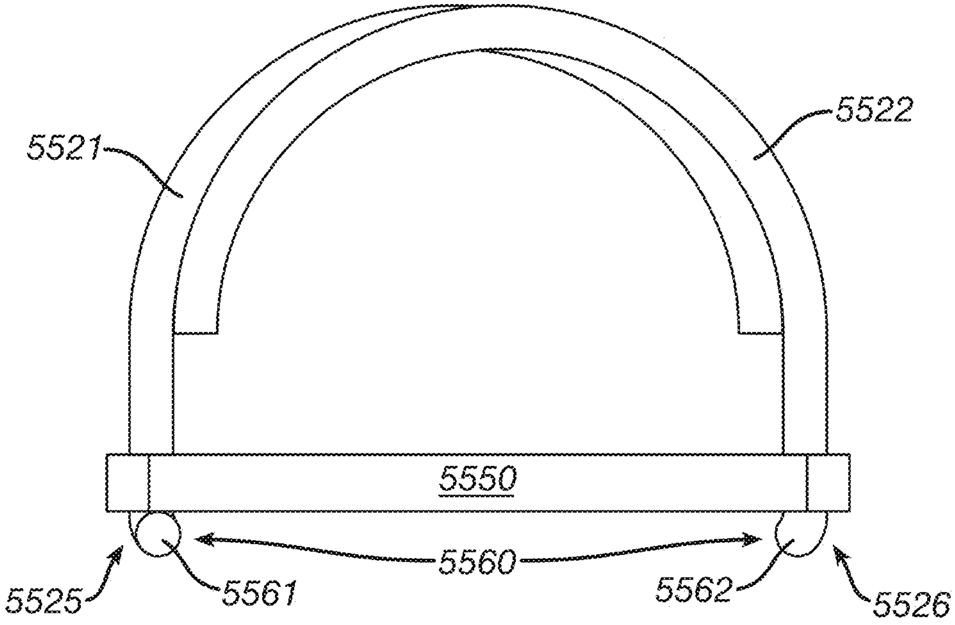
Figure 59:
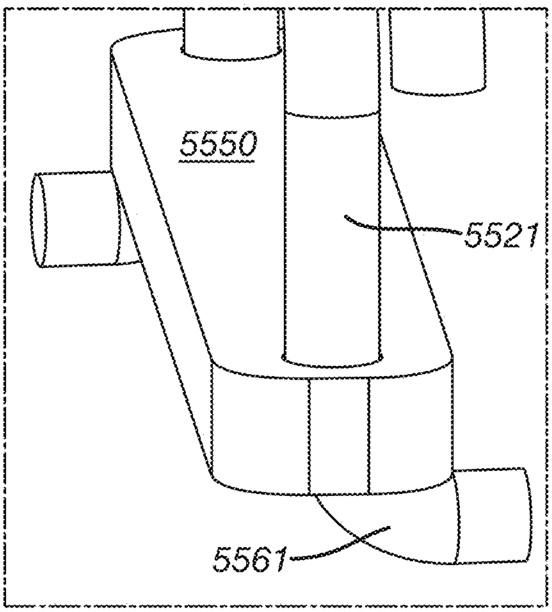
FIG. 59 depicts an enlarged perspective view of a multi-part staple according to one embodiment.

FIGS. 58A and 58B depict a perspective view and front view of a formed multi-part staple, respectively, according to one embodiment. In one embodiment, the feature 5560 includes an out of plane bend of the second end 5525, 5526 of the first and second staple leg portions 5521, 5522, as shown in FIGS. 55, 57, and 58. FIG. 59 depicts an enlarged perspective view of a multi-part staple according to one embodiment. Specifically, FIG. 59 depicts an enlarged view of the feature 5560 being an out of plane bend. As shown in FIG. 59, the out of plane bend results in the staple leg forming a "J" shape that is designed and configured to catch the crown portion 5550 and lift the crown portion 5550 up and out of the staple pocket during and upon completion of the firing stroke. While the "J" shape out of plane bend is one example of the feature, other features are contemplated. For instance, in another embodiment, the feature 5560 may include an end cap having a diameter larger than a diameter of the first and second apertures 5541, 5542. In yet another embodiment, the staple legs 5521, 5522 may taper in diameter at the second ends, such that the second ends gradually increase in diameter towards the tips of the staple legs 5521, 5522. In this case, as the staple legs 5521, 5522 advance through the apertures 5541, 5542, the larger diameter ends or tips of the staple legs 5521, 5522 do not fit through the apertures 5541, 5542 and the crown portion 5550 is released with the staple legs 5521, 5522. In other words, the crown portion 5550 and the staple legs 5521, 5522 deploy as a final, formed staple, as shown in FIGS. 58A and 58B.

In one embodiment, a staple cartridge includes a set of arbors 5530 disposed adjacent a staple pocket having an opening, the set of arbors 5530 including an upper set of arbors 5531 and a lower set of arbors 5532 disposed vertically below the upper set of arbors 5531. The staple cartridge can include a multi-part staple including a first leg 5521, a second leg 5522, and a pledget 5550, where the pledget 5550 is disposed on top of the lower set of arbors 5532. In this embodiment, at least the upper set of arbors 5531 are configured to curl the first leg 5521 and the second leg 5522 as the first leg 5521 and the second leg 5522 exit the staple pocket at the opening during a firing stroke.

The pledget 5550 can include a plurality of apertures 5541, 5542 defined therein which can be configured to slidably receive and/or guide the legs 5521, 5522 of a staple therein. For example, the pledget 5550 can include a first aperture 5541 disposed at a first end 5551 of the pledget 5550 and configured to receive the first leg 5521, and a second aperture 5542 disposed at a second end 5552 of the pledget 5550 and configured to receive the second staple leg 5522. In addition to or in lieu of the apertures 5541, 5542, a pledget 5550 can include any suitable opening such as a slot, guide, and/or groove, for example, which can be configured to slidably receive and/or guide the staple legs 5521, 5522. In certain embodiments, as illustrated in FIGS. 56A and 56B, the tips 5523, 5524 (or top portions) of the staple legs 5521, 5522 can be positioned within the apertures 5541, 5542 when the staples are in their unfired positions. In at least one such embodiment, the tips of the staple legs 5521, 5522 can protrude above the pledget 5550 when the staples are in their unfired position. In certain other embodiments, the tips of the staple legs 5523, 5524 may be positioned just below the pledget 5550 when the staples are in their unfired positions such that, when the staples are moved upwardly through the staple pocket, the staple legs 5521, 5522 can enter into the apertures 5541, 5542 of the pledget 5550 and slide therethrough. In any event, when the legs 5521, 5522 of the staples are positioned within the pledget 5550, the lateral and/or longitudinal movement of the staple legs 5521, 5522 can be limited without preventing the upward movement of the staple legs 5521, 5522 when the staples are deployed. When the staples are deployed, the staple legs 5521, 5522 can slide upwardly through the pledget 5550 to penetrate the tissue T, curl based on contact with the set of arbors 5530, and deform downwardly to form the final staple and capture the tissue therein, as shown in FIGS. 58A and 58B.

Similar to above, in this embodiment, as shown in FIGS. 58A and 58B, the first leg 5521 includes a first end 5523 configured to pass through the first aperture 5541 and a second end 5525 opposite the first end 5523, the second end 5525 including a first feature 5561 to prevent the second end 5525 from passing through the first aperture 5541 during the firing stroke. Likewise, the second leg 5522 includes a first end 5524 configured to pass through the second aperture 5542 and a second end 5526 opposite the first end 5524, the second end 5526 including a second feature 5562 to prevent the second end 5526 from passing through the second aperture 5542 during the firing stroke. The first feature 5561 and the second feature 5562 include an out of plane bend of the second end 5525, 5526 of the first and second staple leg portions 5521, 5522. In one embodiment, the out of plane bend of the second end 5525 of the first leg 5521 is in a first direction, and the out of plane bend of the second end 5526 of the second leg 5522 is in a second direction opposite the first direction. In some examples, the first feature 5561 and the second feature 5562 include an end cap having a diameter larger than a diameter of the first and second apertures 5541, 5542.

In one example, respective first ends 5523, 5524 of respective first and second legs 5521, 5522 are configured to pass through the first and second apertures 5541, 5542, respectively, during the firing stroke, and wherein respective second ends 5525, 5526 opposite respective first ends 5523, 5524 of respective first and second legs 5521, 5522 are configured to engage a bottom surface of the pledget 5550 upon completion of the firing stroke, such that the pledget 5550 is driven out of the staple pocket with the first and second legs 5521, 5522.

In yet another embodiment, the apertures 5541, 5542 in the crown portion or pledget 5550 may act as an arbor, or staple forming feature or surface. In other words, the apertures 5541, 5542 may be deforming apertures within a crown portion of pledget 5550. For example, a staple cartridge includes a staple pocket having an opening and a multi-part staple. The multi-part staple includes a first leg 5521, a second leg 5522, and a pledget 5550. In this example, the pledget 5550 includes a first aperture 5541 disposed at a first end 5551 of the pledget 5550 and configured to receive the first leg 5521, and a second aperture 5542 disposed at a second end 5552 of the pledget 5550 and configured to receive the second staple leg 5522.

In this embodiment, the first aperture 5541 is configured to curl the first leg 5521 as the first leg 5521 passes through the first aperture 5541 during a firing stroke. Similarly, the second aperture 5542 is configured to curl the second leg 5522 as the second leg 5522 passes through the second aperture 5542 during the firing stroke. Similar to above, the pledget 5550 is configured to release with the first leg 5521 and the second leg 5522 upon completion of the firing stroke.

Figure 60A:
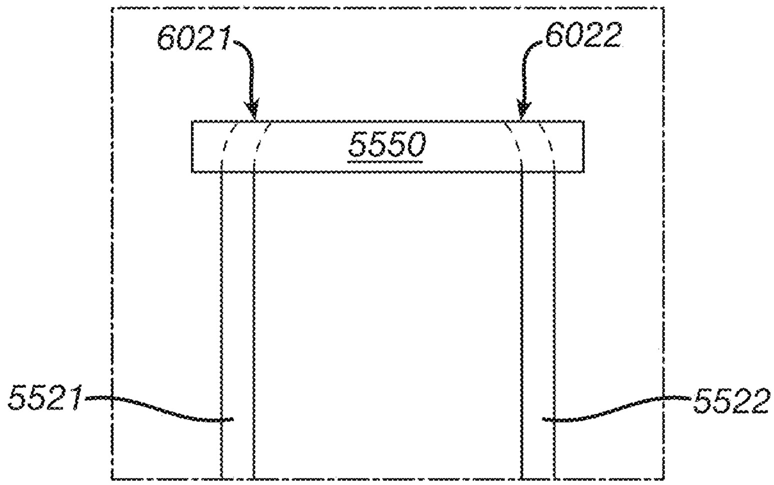
FIGS. 60A and 60B depict deforming apertures within a pledget according to one embodiment.
Figure 60B:
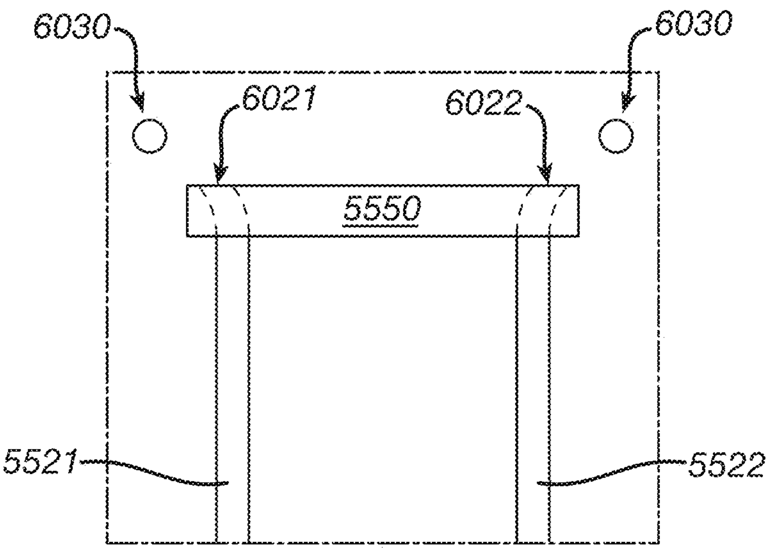

FIGS. 60A and 60B depict deforming apertures within a pledget 5550 according to one embodiment. As shown in FIGS. 60A and 60B, the first aperture 5541 comprises a first curved passageway 6021, such that the first leg 5521 plastically deforms in a first direction as the first leg 5521 passes through the first curved passageway 6021. Similarly, the second aperture 5542 comprises a second curved passageway 6022, such that the second leg 5522 plastically deforms in a second direction as the second leg 5522 passes through the second curved passageway 6022. In one example, the first direction and the second direction are opposite each other. FIGS. 60A and 60B show the curved passageways 6021, 6022 curving in different directions. Having staple forming features within a crown portion or pledget 5550 may eliminate the need for some (or all) of the arbors. However, if the lower set of arbors, such as lower set of arbors 5532, are removed, the pledget 5550 would need to be held in place by another mechanism, device, or structure, such as small pins or rods extending underneath the pledget 5550 within the staple pocket.

The passageways 6021, 6022 going through the pledget 5550 may not only curve in the x-y coordinate plane, but the passageways 6021, 6022 of the pledget 5550 may also curve or extend through the pledget 5550 in the z-coordinate direction. In other words, if the passageways 6021, 6022 extending through the pledget 5550 are angled properly, the staple legs 5521, 5522 can curl out of plane while exiting the apertures 5541, 5542 of the pledget 5550. This would result in the final staple having a 3D shape, such as shown in FIG. 58A, and as disclosed in U.S. patent application Ser. No. 18/781,566, entitled "Staple Cartridge With Static Angled Arbors To Form Three-Dimensional (3D) Staples," filed on Jul. 23, 2024, the disclosure of which is incorporated by reference herein, in its entirety.

Similar to above, the first leg 5521 includes a first end 5523 configured to pass through the first aperture 5541 and a second end 5525 opposite the first end 5523, the second end 5525 including a first feature 5561 to prevent the second end 5525 from passing through the first aperture 5541 during the firing stroke. Likewise, the second leg 5522 includes a first end 5524 configured to pass through the second aperture 5542 and a second end 5526 opposite the first end 5524, the second end 5526 including a second feature 5562 to prevent the second end 5526 from passing through the second aperture 5542 during the firing stroke. In one example, the first feature 5561 and second feature 5562 are each configured to engage a bottom surface of the pledget 5550 upon completion of the firing stroke, such that the pledget 5550 is driven out of the staple pocket with the first and second legs 5521, 5522.

Referring back to FIGS. 60A and 60B, the staple cartridge arrangement described above may also include a set of arbors 6030 disposed adjacent the opening of the staple pocket, wherein the set of arbors 6030 are configured to further deform the first leg 5521 and the second leg 5522 as first leg 5521 and the second leg 5522 exit the staple pocket at the opening. FIG. 60B shows the pledget 5550 having passageways, or channels, that also act as arbors, or staple forming surfaces, as well as the additional set of arbors 6030.

A multi-part staple having a separate crown portion or pledget 5550 such as that disclosed herein also provides the benefit of the crown portion or pledget 5550 being able to act as a carrier or delivery mechanism and deliver different types of payloads to the tissue. For example, in some embodiments, the disclosed pledget 5550 may contain an absorbable foam layer or cushion that acts as a buttress layer. The foam layer or cushion may help adjust compression on the tissue by adding compliance and allowing for varying tissue thickness. In this way, a cartridge can contain one size of staple that can handle different tissue thicknesses. The absorbable foam layer may be constructed of a foam, a matrix, a cushion, an adjunct, or other elastic construct that can densify over time, including materials described in U.S. Pat. No. 10,966,722 entitled "Adjunct Materials And Methods Of Using Same In Surgical Methods For Tissue Sealing," issued Apr. 6, 2021 or adjuncts described in U.S. Pub. No. 2023/0301674 entitled "Tissue Cushion Adjunct For Surgical Stapler End Effector," published Sep. 28, 2023. In another example, rather than a foam layer, the pledget 5550 may contain and deliver a microbial or hemostatic pad, or other medicants such as antibiotics.

The staple shape and arrangement described above includes arbors and a multi-part, or deconstructed, staple with separate legs and crown pieces to facilitate staple release from the arbors. The staple crown is located above the lower arbors so that as the staple legs curl, the lower or inner arbors do not get trapped inside the staple (or the staple crown does not get trapped under the lower arbors). This avoids the issue of having to move or deploy the arbors in order to fire a staple. Thus, the disclosed staple cartridges accommodate for spanning the tissue gap and allow staple release.

The terms "upper," "lower," "vertically," "bottom," "top" or "on top," are relative terms to provide additional clarity to the figure descriptions provided below, and may refer to a position within a staple pocket. The terms "upper," "lower," "vertically," "bottom," "top" or "on top," are thus not intended to unnecessarily limit the invention described herein.

X. EXAMPLES OF COMBINATIONS

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the examples/clauses below. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example/Clause Set No. 1

A. A method of forming staples between opposing jaws of a stapling device, the method comprising:
- positioning a set of guide surfaces over each of a plurality of staples loaded in openings of a staple cartridge of a first jaw of the opposing jaws of the stapling device, wherein each staple comprises a crown with staple legs extending therefrom, wherein ends of the staple legs opposite the crown exit through the openings; and
- bending the ends of the staple legs with the guide surfaces;
- wherein the guide surfaces are further configured to cause the staple legs to continue bending as the staples exit the openings.

B. The method of clause A, wherein the plurality of staples are loaded in the openings of the first jaw such that the ends of the staple legs extend out of the openings, and wherein bending the ends of the staple legs comprises bending, by the guide surfaces, the ends of the staple legs that extend out of the openings as the guide surfaces are positioned over the staples.

C. The method of clause B, wherein when positioning the set of guide surfaces over each of the plurality of staples, the plurality of staples are supported at the crown of the staple.

D. The method of clause A, further comprising attaching the guide surfaces to the first jaw adjacent to the openings.

E. The method of clause A, further comprising firing the stapling device with a firing force after bending the ends of the staple legs with the guide surfaces, wherein firing the stapling device causes the staples to exit the openings.

F. The method of clause E, wherein firing the stapling device causes the staple legs to continue bending by forcing the staple legs past the guide surfaces using the firing force.

G. The method of clause A, wherein the staples are retained, by the guide surfaces, in the openings of the first jaw prior to firing the stapling device.

H. The method of clause A, wherein to cause the staple legs to continue bending, the guide surfaces are configured to curl the staple legs using the guide surfaces of the first jaw only.

I. The method of clause A, wherein to cause the staple legs to continue bending, the guide surfaces are configured to curl the staple legs without buckling the staple legs.

J. The method of clause A, wherein to cause the staple legs to continue bending, the guide surfaces are configured to curl the staple legs while avoiding contact with a second jaw of the opposing jaws.

K. A staple cartridge, comprising:

a cartridge body including a staple cavity having a staple aperture in a top surface of the cartridge body, the staple cavity being configured to receive a surgical staple such that the staple is vertically movable within the staple cavity along a longitudinal axis of the staple cavity; and a staple forming plate configured to be attached to the top surface of the cartridge body, wherein the staple forming plate includes a tissue contacting top surface and a bottom surface opposite the tissue contacting top surface, the staple forming plate including a staple forming channel defined in, and extending through, the staple forming plate between the tissue contacting top surface and the bottom surface, wherein when the staple forming plate is attached to the top surface of the cartridge body, the staple forming channel is aligned with the staple aperture of the staple cavity.

L. The staple cartridge of clause K, wherein the staple includes a first staple leg and a second staple leg, wherein the staple cavity is further configured to receive the staple such that a portion of the first staple leg and a portion of the second staple leg extend out of the staple aperture in the top surface of the cartridge body.

M. The staple cartridge of clause L, wherein the staple forming channel comprises:

a first staple forming region configured to receive the portion of the first staple leg extending out of the staple aperture, wherein the first staple forming region includes a first curved surface disposed adjacent the tissue contacting top surface of the staple forming plate; and a second staple forming region configured to receive the portion of the second staple leg extending out of the staple aperture, wherein the second staple forming region includes a second curved surface disposed adjacent the tissue contacting top surface of the staple forming plate, wherein the first curved surface and the second curved surface are configured to bend a tip of the portion of the first staple leg and a tip of the portion of the second staple leg, respectively, laterally relative to the longitudinal axis of the staple cavity when the staple forming plate is attached to the top surface of the cartridge body.

N. The staple cartridge of clause M, wherein the first staple forming region further includes a first arbor offset laterally from the first curved surface towards a center of the staple forming channel, such that the portion of the first staple leg is disposed between the first arbor and the first curved surface, and the second staple forming region further includes a second arbor offset laterally from the second curved surface towards the center of the staple forming channel, such that the portion of the second staple leg is disposed between the second arbor and the second curved surface.

O. The staple cartridge of clause N, wherein when the staple is advanced out of the staple cavity and through the staple forming channel of the staple forming plate, the first staple leg and second staple leg are curled toward each other based on the first staple leg and second staple leg contacting the first curved surface and second curved surface, respectively.

P. The staple cartridge of clause M, wherein the staple cartridge is configured to be used with a surgical stapler, and wherein the first curved surface and the second curved surface are configured to retain the staple in the staple cavity prior to firing the surgical stapler.

Q. A circular surgical stapling system, comprising:

a staple cartridge comprising at least one annular row of staple cavities configured to hold staples having staple legs;

an anvil configured to be positioned opposite the staple cartridge; and an annular arbor plate configured to be coupled to the staple cartridge, wherein the annular arbor plate includes a plurality of annular channels corresponding to the staple cavities, and wherein each annular channel of the plurality of annular channels includes a feature that curls the staple legs upon a firing of the staples.

R. The circular surgical stapling system of clause Q, wherein the feature comprises a curved sidewall, an arbor, or a combination thereof.

S. The circular surgical stapling system of clause Q, wherein the feature is configured to bend a portion of the staple legs when the annular arbor plate is coupled to the staple cartridge.

T. The circular surgical stapling system of clause Q, wherein the feature curls the staple legs upon the firing of the staples without buckling the staple legs against the anvil.

Example/Clause Set No. 2

A. A staple cartridge comprising:

a cartridge body;

a staple pocket in the cartridge body, the staple pocket having an opening and containing an unformed staple comprising a first leg and a second leg, the staple pocket containing the first leg and the second leg of the unformed staple in an unfired position; and two or more guide surfaces in the staple pocket disposed adjacent the opening, wherein the guide surfaces are configured to deform the first leg of the unformed staple as the first leg exits the staple pocket at the opening during a firing of the unformed staple.

B. The staple cartridge of clause A, wherein the guide surfaces are integrally formed with a sidewall of the staple pocket.

C. The staple cartridge of clause B, wherein the guide surfaces comprise a first arbor that spans across the opening.

D. The staple cartridge of clause C, wherein the first arbor comprises an interrupted arbor having a first portion and a second portion spaced apart from, and axially aligned with, the first portion.

E. The staple cartridge of clause D, wherein the first portion and second portion of the interrupted arbor are spaced apart by a gap, and wherein a distance of the gap is less than a diameter of a crown of the unformed staple.

F. The staple cartridge of clause C, wherein the guide surfaces further comprise a second arbor disposed adjacent the opening, wherein the first arbor and the second arbor are offset from one another vertically and horizontally within the staple pocket.

G. The staple cartridge of clause F, wherein the first leg is configured to exit the staple pocket between the first arbor and the second arbor, such that the first arbor and the second arbor deform the first leg as the first leg exits the staple pocket.

H. The staple cartridge of clause A, further comprising a tissue gripping feature disposed at the opening of the staple pocket, and wherein the guide surfaces are disposed within the tissue gripping feature.

I. The staple cartridge of clause A, wherein the cartridge body is configured to interface with an end effector of a surgical stapling instrument, the end effector comprising:
  a first jaw comprising an anvil; and
  a second jaw including an elongated channel, wherein the first jaw and second jaw are relatively pivotable between an open position and a closed position,
  wherein the cartridge body is insertable into the elongated channel for assembly therewith.

J. A surgical stapler, comprising:
  a first jaw;
  a second jaw wherein at least one of the first jaw and the second jaw is movable relative to the other to grasp tissue, the second jaw containing a staple cartridge, the staple cartridge including:
    a proximal end;
    a distal end;
    a tissue supporting deck;
    a plurality of rows of staple cavities defined in the deck and configured to hold unformed staples;
    a staple forming feature disposed in the staple cavities;
    a plurality of drivers configured to drive the unformed staples out of the staple cavities toward the first jaw; and
    a sled movable from the proximal end to the distal end of the staple cartridge during a firing stroke to lift the plurality of drivers toward the first jaw,
  wherein the staple forming feature is configured to deform the unformed staples during the firing stroke to formed staples having a formed staple height.

K. The surgical stapler of clause J, wherein the unformed staples are deformed into the formed staples by the staple forming feature while avoiding contact with the first jaw.

L. The surgical stapler of clause J, wherein the unformed staples have the same height.

M. The surgical stapler of clause J, wherein the unformed staples in at least one row of staple cavities of the plurality of rows of staple cavities have different heights.

N. The surgical stapler of clause J, wherein the formed staple height of the formed staples is less than a distance between the plurality of staple drivers and the first jaw at an end of the firing stroke.

O. The surgical stapler of clause J, wherein during the firing stroke, when a tissue thickness and a distance between the first jaw and the second jaw in which the unformed staples are formed is uniform across the plurality of rows of staple cavities, and when the plurality of drivers are lifted no further than the deck of the staple cartridge, the unformed staples in different rows of the plurality of rows of staple cavities are formed to different formed staple heights.

P. The surgical stapler of clause J, wherein a width of the formed staples is the same as a width of the unformed staples.

Q. A staple cartridge comprising:
  a cartridge body;
  a staple pocket in the cartridge body and having an opening;
  a first top arbor disposed adjacent the opening at a first end of the staple pocket;
  a first bottom arbor offset a first distance from the first top arbor;
  a second top arbor disposed adjacent the opening at a second end of the staple pocket; and
  a second bottom arbor offset a second distance from the second top arbor.

R. The staple cartridge of clause Q, wherein the staple pocket contains an unformed staple having a first staple leg and a second staple leg, wherein the first top arbor and the first bottom arbor are configured to deform the first staple leg as the first staple leg exits the staple pocket at the opening, and wherein the second top arbor and the second bottom arbor are configured to deform the second staple leg as the second staple leg exits the staple pocket at the opening.

S. The staple cartridge of clause R, wherein each of the first staple leg and second staple leg have an angled tip, wherein as the unformed staple exits the staple pocket, the first staple leg is configured to pass between the first top arbor and the first bottom arbor, such that the angled tip of the first staple leg contacts the first top arbor causing the first staple leg to curl toward and over the first bottom arbor, and the second staple leg is configured to pass between the second top arbor and the second bottom arbor, such that the angled tip of the second staple leg contacts the second top arbor causing the second staple leg to curl toward and over the second bottom arbor.

T. The staple cartridge of clause R, wherein the first staple leg and the second staple leg are deformed such that the first staple leg and the second staple leg curl toward each other to form a formed staple.

U. The staple cartridge of clause R, wherein when the first distance and the second distance are equal, a curl radius and curl height of the first staple leg is equal to a curl radius and curl height of the second staple leg, respectively.

V. The staple cartridge of clause R, wherein when the first distance and the second distance are different, a curl radius and curl height of the first staple leg is different than a curl radius and curl height of the second staple leg, respectively.

Example/Clause Set No. 3

A. A surgical stapling system, comprising:
  a stapler including a first jaw having a tissue clamping surface and a second jaw operable to receive interchangeable staple cartridges having different staple patterns, the first and second jaws relatively pivotable between an open position and a closed position;
  a first staple cartridge having a first staple pattern; and
  a second staple cartridge having a second staple pattern, the second staple pattern being different from the first staple pattern, wherein the stapler is configured to perform a first firing stroke to form a first set of staples using the first staple cartridge and a second firing stroke to form a second set of staples using the second staple cartridge.

B. The surgical stapling system of clause A, wherein the first set of staples are formed by the first staple cartridge independently of the first jaw, and wherein the second set of staples are formed by the second staple cartridge independently of the first jaw.

C. The surgical stapling system of clause A, wherein the first set of staples and the second set of staples are formed by staple forming features contained in staple pockets of the first staple cartridge and the second staple cartridge, respectively.

D. The surgical stapling system of clause A, wherein the tissue clamping surface of the first jaw is flat or pocketless.

E. The surgical stapling system of clause A, wherein the first staple pattern and the second staple pattern includes rows of staple pockets configured to receive staples.

F. The surgical stapling system of clause E, wherein the tissue clamping surface of the first jaw includes one or more longitudinal grooves along a length of the tissue clamping surface, wherein the one or more longitudinal grooves accommodate the rows of staple pockets of both the first and second staple patterns of the first and second staple cartridges.

G. The surgical stapling system of clause F, wherein during the first firing stroke and the second firing stroke, the staples in the rows of staple pockets of the first staple pattern and the second staple pattern avoid contact with the one or more longitudinal grooves.

H. The surgical stapling system of clause E, wherein the first staple pattern and the second staple pattern define staple crown orientations within respective rows of staple pockets.

I. The surgical stapling system of clause E, wherein the first staple pattern and the second staple pattern define spacing of staple pockets within respective rows of staple pockets.

J. The surgical stapling system of clause E, wherein the first staple pattern and the second staple pattern define lateral spacing between respective rows of staple pockets.

K. The surgical stapling system of clause E, wherein the first staple pattern and the second staple pattern define a number of staple pockets within respective rows of staple pockets.

L. A staple cartridge, comprising:

a cartridge body including:

a proximal end;

a distal end;

a tissue supporting deck; and a plurality of rows of staple cavities defined in the deck, wherein the staple cavities are configured to hold unformed staples, wherein the unformed staples are configured to be deformed into formed staples by a staple forming feature in the staple cavities to form a first staple pattern.

M. The staple cartridge of clause L, wherein the staple cartridge is configured to be insertable into a channel of a first jaw of an end effector for assembly therewith and to be fired during a firing stroke of the end effector to form the first staple pattern independently of a second jaw of the end effector.

N. The staple cartridge of clause M, wherein the staple forming feature is configured to bend or curl the unformed staples during the firing stroke.

O. The staple cartridge of clause N, wherein the staple forming feature bends or curls the unformed staples while avoiding contact with the second jaw.

P. The staple cartridge of clause L, wherein the first staple pattern defines staple crown orientations within respective rows of staple cavities.

Q. The staple cartridge of clause L, wherein the first staple pattern defines spacing of staple cavities within respective rows of staple cavities or lateral spacing between respective rows of staple cavities.

R. The staple cartridge clause L, wherein the first staple pattern defines a number of staple cavities within respective rows of staple cavities.

S. A method of using a stapler, the stapler including a first jaw having a tissue clamping surface and a second jaw operable to receive interchangeable staple cartridges having different staple patterns, the first and second jaws relatively pivotable between an open position and a closed position, the method comprising:

inserting a first staple cartridge into the second jaw of the stapler, the first staple cartridge having a first staple pattern;

firing the stapler to form a first set of staples using the first staple cartridge;

removing the first staple cartridge from the second jaw of the stapler;

inserting a second staple cartridge into the second jaw of the stapler, the second staple cartridge having a second staple pattern different from the first staple pattern; and firing the stapler to form a second set of staples using the second staple cartridge.

T. The method of clause S, wherein the first set of staples are formed by the first staple cartridge independently of the first jaw, and wherein the second set of staples are formed by the second staple cartridge independently of the first jaw.

Example/Clause Set No. 4

A. A staple cartridge comprising:

a staple opening containing an unformed staple, the staple having a first leg portion and a second leg portion; and a set of guides disposed adjacent the staple opening, wherein, when the staple exits the staple opening, the first leg portion has a first interaction with the guides and the second leg portion has a second interaction with the guides, the second interaction being different than the first interaction, wherein the first interaction and the second interaction correspond to a degree of plastic deformation of the first leg portion and the second leg portion, respectively.

B. The staple cartridge of clause A, wherein the first leg portion is adjacent a staple tip, and wherein the second leg portion is disposed between the first leg portion and a staple crown.

C. The staple cartridge of clause A, wherein the first leg portion includes a first angle of approach to the guides and the second leg portion includes a second angle of approach to the guides, wherein the second angle of approach is greater than the first angle of approach.

D. The staple cartridge of clause A, wherein, during the first interaction with the guides, the first leg portion remains undeformed by the guides.

E. The staple cartridge of clause A, wherein, during the second interaction with the guides, the second leg portion is plastically deformed by the guides.

F. The staple cartridge of clause A, wherein, as the staple exits the staple opening, the first leg portion is formed to a first radius and the second leg portion is formed to a second radius different than the first radius.

G. The staple cartridge of clause F, wherein the second radius is tighter than first radius.

H. The staple cartridge of clause A, wherein the first leg portion is in a first plane and the second leg portion is in a second plane different from the first plane.

I. A surgical staple cartridge comprising:
- a staple pocket having an opening and containing a preformed staple, the staple having an upper leg portion, a middle leg portion, and a lower leg portion; and
- a set of arbors disposed at opposite ends of the opening and adjacent the opening,
- wherein the set of arbors are configured to plastically deform the middle leg portion of the staple as the staple exits the staple pocket at the opening along an exit path.

J. The surgical staple cartridge of clause I, wherein the upper leg portion and the lower leg portion remain undeformed as the staple exits the staple pocket at the opening.

K. The surgical staple cartridge of clause I, wherein the upper leg portion and the lower leg portion are straight and parallel to one another, and wherein the middle leg portion is angled relative to the upper leg portion and the lower leg portion.

L. The surgical staple cartridge of clause I, wherein the middle leg portion is angled in two planes.

M. The surgical staple cartridge of clause I, wherein the set of arbors comprise:
- a top arbor extending into the exit path from a first direction; and
- a bottom arbor offset vertically and horizontally from the top arbor, the bottom arbor extending into the exit path from a second direction opposite the first direction.

N. The surgical staple cartridge of clause M, wherein an end of the top arbor and an end of the bottom arbor overlap in the exit path by an overlap distance in an overlap zone.

O. The surgical staple cartridge of clause N, wherein the set of arbors plastically deform the middle leg portion of the staple as the middle leg portion passes between the top arbor and the bottom arbor in the overlap zone.

P. The surgical staple cartridge of clause N, wherein the upper leg portion is disposed in the staple pocket beyond the end of the top arbor in the first direction.

Q. The surgical staple cartridge of clause N, wherein the lower leg portion includes a staple crown and is disposed in the staple pocket beyond the end of the bottom arbor in the second direction.

R. The surgical staple cartridge of clause I, wherein the set of arbors comprise static arbors that remain in the surgical staple cartridge after the staple exits the staple pocket.

S. A staple cartridge comprising:
- a staple opening containing a preformed staple, the staple having two legs and a crown, wherein the two legs include a straight portion, a crown portion, and an angled portion between the straight portion and the crown portion; and
- arbors disposed at opposite ends of the staple opening and adjacent the staple opening,
- wherein the staple is configured to exit the staple opening during a firing stroke.

T. The staple cartridge of clause S, wherein the firing stroke comprises:
- a first stage of firing;
- a second stage of firing; and
- a third stage of firing,
- wherein during the first stage of firing, the straight portion of the two legs is configured to bypass the arbors and pierce tissue,
- wherein during the second stage of firing, the arbors are configured to curl the two legs as the angled portion of the two legs interface with the arbors, and
- wherein during the third stage of firing, the crown portion of the two legs is configured to bypass the arbors, such that the staple is releasable from the staple cartridge.

Example/Clause Set No. 5

A. A staple cartridge comprising:
- a staple channel having an opening and containing an unformed staple with staple legs and a crown; and
- a set of guide surfaces disposed adjacent the opening,
- wherein the set of guide surfaces are configured to plastically deform the staple legs of the unformed staple out of plane with one another as the staple legs exit the staple channel at the opening, and
- wherein the set of guide surfaces and the crown are angled relative to one another.

B. The staple cartridge of clause A, wherein the set of guide surfaces are integrally formed with a sidewall of the staple channel.

C. The staple cartridge of clause A, wherein the set of guide surfaces are obliquely oriented relative to a longitudinal axis of the staple channel.

D. The staple cartridge of clause A, wherein the set of guide surfaces are disposed along a length of the staple cartridge parallel to a longitudinal axis of the staple cartridge, and wherein the crown is obliquely oriented relative to the longitudinal axis.

E. The staple cartridge of clause A, wherein the unformed staple is plastically deformed into a formed staple by the set of guide surfaces.

F. The staple cartridge of clause E, wherein the formed staple has a three-dimensional (3D) shape.

G. The staple cartridge of clause E, wherein the formed staple has a B-shape.

H. The staple cartridge of clause E, wherein the set of guide surfaces are releasable with the formed staple.

I . The staple cartridge of clause A, wherein an angle between the set of guide surfaces and the crown is between 5 and 20 degrees.

J. A staple cartridge comprising:
- a set of guide surfaces disposed along a length of the staple cartridge parallel to a longitudinal axis of the staple cartridge; and
- a staple channel having an opening and containing a staple with staple legs and a crown, wherein the crown is obliquely oriented relative to the longitudinal axis,
- wherein the set of guide surfaces are configured to curl the staple legs of the staple as the staple legs exit the staple channel at the opening.

K. The staple cartridge of clause J, wherein during a firing stroke, the staple legs of the staple are curled into a formed staple by the set of guide surfaces.

L. The staple cartridge of clause K, wherein the formed staple has a three-dimensional (3D) shape.

M. The staple cartridge of clause K, wherein the staple legs of the formed staple are parallel to each other.

N. The staple cartridge of clause K, wherein the crown and the staple legs of the formed staple are angled relative to one another.

O. The staple cartridge of clause J, wherein the set of guide surfaces are parallel to a cut line and the crown is angled relative to the cut line.

P. A staple cartridge comprising:

a staple pocket having an opening and containing a staple with staple legs and a staple crown; and a set of arbors disposed adjacent the opening, wherein the set of arbors are integrally formed with a sidewall of the staple pocket and extend away from the sidewall at an angle, wherein the set of arbors are configured to bend the staple legs of the staple as the staple legs exit the staple pocket at the opening to form a formed staple.

Q. The staple cartridge of clause P, wherein the staple crown is parallel to a cutline and the set of arbors are angled relative to the cut line.

R. The staple cartridge of clause P, wherein the staple legs of the formed staple are in a first plane and the staple crown of the formed staple is in a second plane different from the first plane.

S. The staple cartridge of clause P, wherein the staple legs of the formed staple are spaced apart from each other, such that a distance between the staple legs of the formed staple is greater than a width of the staple pocket.

T . The staple cartridge of clause P, wherein the formed staple has a three-dimensional (3D) shape.

U. A staple cartridge comprising:

a staple channel containing a staple with staple legs and a crown; and a set of arbors disposed adjacent the staple channel, wherein the set of arbors are configured to bend the staple legs of the staple as the staple legs exit the staple channel.

V. The staple cartridge of clause U, wherein the set of arbors are configured to bend the staple legs perpendicularly to the crown.

Example/Clause Set No. 6

A. A staple cartridge comprising:

a proximal end;

a distal end;

a tissue supporting deck;

a staple cavity defined in the deck and configured to hold a staple;

a set of guide surfaces disposed adjacent the staple cavity;

a driver configured to drive the staple out of the staple cavity; and a sled movable from the proximal end to the distal end of the staple cartridge during a firing stroke to lift the driver, wherein a subset of the set of guide surfaces are movable relative to a remaining set of the set of guide surfaces in response to movement of a movable cartridge component during the firing stroke, the subset of the set of guide surfaces being configured to curl the staple during the firing stroke.

B. The staple cartridge of clause A, wherein a movement of the subset of the set of guide surfaces causes a change in a curl radius of the staple during the firing stroke.

C. The staple cartridge of clause B, wherein the curl radius of the staple is based on a position of the subset of the set of guide surfaces during the firing stroke.

D. The staple cartridge of clause A, wherein the movable cartridge component is the driver, and wherein a curl radius of the staple during the firing stroke is based on a vertical position of the driver in the staple cavity.

E . The staple cartridge of clause D, wherein a ramped surface is disposed on a top surface of the driver, and wherein as the driver moves vertically within the staple cavity, the ramped surface is configured to contact the subset of the set of guide surfaces and deflect the subset of the set of guide surfaces laterally within the staple cavity.

F. The staple cartridge of clause A, wherein the movable cartridge component is a compressible member spanning between the guide surfaces, and wherein a curl radius of the staple during the firing stroke is based on a compression force applied to the compressible member.

G. The staple cartridge of clause F, wherein the curl radius is tighter when a higher compression force is applied, and wherein the curl radius is looser when a lower compression force is applied.

H. A staple cartridge comprising:

a proximal end;

a distal end;

a tissue supporting deck;

a staple cavity defined in the deck and configured to hold a staple;

a set of guide surfaces disposed adjacent the staple cavity;

a driver configured to drive the staple out of the staple cavity; and a sled movable from the proximal end to the distal end of the staple cartridge during a firing stroke to lift the driver, wherein at least some of the guide surfaces are movable in response to movement of the driver and configured to curl the staple during the firing stroke at a non-constant curl radius.

I. The staple cartridge of clause H, wherein a movement of the driver causes a change in the curl radius of the staple during the firing stroke.

J. The staple cartridge of clause H, wherein the curl radius of the staple during the firing stroke is based on a vertical position of the driver in the staple cavity.

K. The staple cartridge of clause H, wherein the driver comprises a cam disposed on a top surface of the driver, and wherein as the driver moves vertically within the staple cavity, the cam is configured to contact the guide surfaces and deflect the guide surfaces laterally within the staple cavity.

L. The staple cartridge of clause K, wherein as the guide surfaces deflect laterally based on contact with the cam, the curl radius of the staple during the firing stroke tightens.

M. The staple cartridge of clause K, wherein the cam is a ramp having inclined surfaces configured to engage and deflect the guide surfaces, wherein the curl radius changes as a function of an angle of the inclined surfaces.

N. A staple cartridge comprising:

a staple cavity configured to hold a staple;

a set of guide surfaces disposed adjacent the staple cavity; and a compressible spring spanning between the guide surfaces, wherein the guide surfaces are movable in response to movement of the compressible spring and configured to curl the staple during a firing stroke at a non-constant curl radius.

O. The staple cartridge of clause N, wherein a movement of the compressible spring causes a change in the curl radius of the staple during the firing stroke.

P. The staple cartridge of clause N, wherein the curl radius of the staple during the firing stroke is based on a compression force applied to the compressible spring.

Q. The staple cartridge of clause P, wherein the curl radius is smaller when a higher compression force is applied, and wherein the curl radius is larger when a lower compression force is applied.

R. The staple cartridge of clause N, wherein the compressible spring comprises a leaf spring, and wherein as a compression force applied to the leaf spring increases, the leaf spring is configured to move the guide surfaces laterally within the staple cavity.

S. The staple cartridge of clause R, wherein as the guide surfaces move laterally based on interaction with the leaf spring, the curl radius of the staple during the firing stroke tightens.

T. The staple cartridge of clause R, wherein movement of the guide surfaces laterally allows the guide surfaces to release from the staple cartridge.

Example/Clause Set No. 7

A. A staple cartridge comprising:
- a tissue supporting deck; and
- a set of arbor inserts removably coupled to the deck adjacent a staple pocket, the staple pocket being configured to hold a staple,
- wherein the set of arbor inserts is configured to plastically deform the staple as the staple exits the staple pocket during a firing stroke.

B. The staple cartridge of clause A, wherein the set of arbor inserts comprises a frangible portion configured to removably hold the set of arbor inserts in place by a retention force, wherein the retention force is greater than a curling force needed to deform the staple and less than a driving force of a driver at the end of the firing stroke.

C. The staple cartridge of clause B, wherein the frangible portion is configured to break away from the deck of the staple cartridge when a force greater than the retention force is exerted on the set of arbor inserts, such that the set of arbor inserts is releasable upon exertion of the force.

D. The staple cartridge of clause C, wherein the force is between about 3 pound-force to about 6 pound-force.

E. The staple cartridge of clause A, wherein the set of arbor inserts is made from bioabsorbable material.

F. The staple cartridge of clause A, wherein the set of arbor inserts contains or is made from a chemical substance, such that when the set of arbor inserts releases with the staple into tissue upon completion of the firing stroke, the chemical substance reacts with the staple to influence a speed of absorption of the staple in the tissue.

G. The staple cartridge of clause F, wherein the chemical substance inhibits matrix metalloproteinase (MMP) to promote healing.

H. The staple cartridge of clause A, wherein the set of arbor inserts contains a compressible cushion or layer.

I. The staple cartridge of clause H, wherein the compressible cushion or layer is absorbable.

J. The staple cartridge of clause H, wherein the staple is plastically deformed into a formed staple as the staple exits the staple pocket during the firing stroke, wherein tissue is captured within the formed staple, and wherein the compressible cushion or layer produces at least 8 g/mm^2 to the tissue captured within the formed staple.

K. The staple cartridge of clause A, wherein the staple is plastically deformed into a formed staple as the staple exits the staple pocket during the firing stroke, and wherein the set of arbor inserts is configured to axially connect with another set of arbor inserts of an axially adjacent staple pocket, such that when both sets of arbor inserts are released with respective formed staples, the respective formed staples are connected.

L. The staple cartridge of clause A, wherein the staple comprises a magnesium staple, wherein the set of arbor inserts contains or is made from a material, such that when the set of arbor inserts releases with the staples into tissue upon completion of a firing stroke, the material produces a galvanic reaction with the magnesium staple.

M. A staple cartridge comprising:
- a tissue supporting deck; and
- a set of arbor inserts removably coupled to the deck, the set of arbor inserts including:
  - a first arbor insert disposed on the deck adjacent a first staple pocket configured to hold a first staple;
  - a second arbor insert disposed on the deck adjacent a second staple pocket configured to hold a second staple, the second staple pocket being adjacent the first staple pocket; and
  - a coupler axially connecting the first arbor insert and the second arbor insert,
- wherein the first arbor insert is configured to plastically deform a staple leg of the first staple as the first staple exits the first staple pocket during a firing stroke,
- wherein the second arbor insert is configured to plastically deform a staple leg of the second staple as the second staple exits the second staple pocket during the firing stroke.

N. The staple cartridge of clause M, wherein the first arbor insert is configured to fit within a first end of the first staple pocket, and wherein the first arbor insert is resiliently biased against sidewalls of the first staple pocket to provide a friction fit between the first arbor insert and the sidewalls of the first staple pocket.

O. The staple cartridge of clause N, wherein the second arbor insert is configured to fit within a first end of the second staple pocket, and wherein the second arbor insert is resiliently biased against sidewalls of the second staple pocket to provide a friction fit between the second arbor insert and the sidewalls of the second staple pocket.

P. The staple cartridge of clause O, wherein the friction fit between the first arbor insert and the sidewalls of the first staple pocket provides a first retention force for removably holding the first arbor insert in place, and wherein the friction fit between the second arbor insert and the sidewalls of the second staple pocket provides a second retention force for removably holding the second arbor insert in place.

Q. The staple cartridge of clause P, wherein the first arbor insert and the second arbor insert are configured to break away from the deck of the staple cartridge when a force greater than the first retention force and the second retention force is exerted on the first arbor insert and the second arbor insert, respectively.

R. The staple cartridge of clause M, wherein the first staple is plastically deformed into a first formed staple as the first staple exits the first staple pocket during the firing stroke, wherein the second staple is plastically deformed into a second formed staple as the second staple exits the second staple pocket during the firing stroke, and wherein when the first arbor insert and the second arbor insert are released with respective first and second formed staples, the respective first and second formed staples are connected via the first and second arbor inserts and the coupler.

S. A staple cartridge comprising:
- a tissue supporting deck; and
- a set of arbor inserts removably coupled within a staple pocket of the deck, the staple pocket configured to hold a staple, the set of arbor inserts including:
  - a first arbor insert disposed at a first end of the staple pocket;
  - a second arbor insert disposed at a second end of the staple pocket; and
  - a platform spanning the staple pocket and connecting the first arbor insert and the second arbor insert, wherein the first arbor insert is configured to plastically deform a first staple leg of the staple as the staple exits the staple pocket during a firing stroke, wherein the second arbor insert is configured to plastically deform a second staple leg of the staple as the staple exits the staple pocket during the firing stroke.

T. The staple cartridge of clause S, wherein the set of arbor inserts is configured to fit within the staple pocket and be resiliently biased against sidewalls of the staple pocket to provide a friction fit between the set of arbor inserts and the sidewalls of the staple pocket.

U. The staple cartridge of clause T, wherein the friction fit between the set of arbor inserts and the sidewalls of the staple pocket provides a retention force for removably holding the set of arbor inserts in place.

V. The staple cartridge of clause U, wherein the set of arbor inserts is configured to break away from the deck of the staple cartridge during the firing stroke when a force greater than the retention force is exerted on the set of arbor inserts.

W. The staple cartridge of clause V, further comprising an absorbable cushion, foam, pad, or other medicants disposed on the platform, such that when the set of arbor inserts breaks away from the deck of the staple cartridge into tissue upon completion of the firing stroke, the absorbable cushion, foam, pad, or other medicants are delivered to the tissue.

Example/Clause Set No. 8

A. A staple cartridge comprising:

a set of arbors disposed adjacent a staple pocket having an opening, the set of arbors including an upper set of arbors and a lower set of arbors; and a multi-part staple including a first staple leg portion, a second staple leg portion, and a crown portion, wherein the crown portion is disposed vertically between the upper set of arbors and the lower set of arbors, wherein the set of arbors are configured to curl the first staple leg portion and the second staple leg portion as the first staple leg portion and the second staple leg portion exit the staple pocket at the opening during a firing stroke.

B. The staple cartridge of clause A, wherein the crown portion includes a first aperture disposed at a first end of the crown portion and a second aperture disposed at a second end of the crown portion, the first aperture being configured to receive the first staple leg portion and the second aperture being configured to receive the second staple leg portion.

C. The staple cartridge of clause B, wherein a first end of the first staple leg portion and a first end of the second staple leg portion is configured to pass through the first aperture and the second aperture of the crown portion, respectively, during the firing stroke.

D. The staple cartridge of clause C, wherein a second end of the first staple leg portion includes a feature to prevent the second end of the first staple leg portion from passing through the first aperture of the crown portion during the firing stroke, and wherein a second end of the second staple leg portion includes a feature to prevent the second end of the second staple leg portion from passing through the second aperture of the crown portion during the firing stroke, such that the crown portion releases with the first staple leg portion and the second staple leg portion into tissue upon completion of the firing stroke.

E. The staple cartridge of clause D, wherein the feature includes an out of plane bend of the second end of the first and second staple leg portions.

F. The staple cartridge of clause D, wherein the feature includes an end cap having a diameter larger than a diameter of the first and second apertures.

G. The staple cartridge of clause A, wherein arbors of the upper set of arbors are spaced apart by a first distance and arbors of the lower set of arbors are spaced apart by a second distance less than the first distance.

H. A staple cartridge comprising:

a set of arbors disposed adjacent a staple pocket having an opening, the set of arbors including an upper set of arbors and a lower set of arbors disposed vertically below the upper set of arbors; and a multi-part staple including a first leg, a second leg, and a pledget, wherein the pledget is disposed on top of the lower set of arbors, wherein at least the upper set of arbors are configured to curl the first leg and the second leg as the first leg and the second leg exit the staple pocket at the opening during a firing stroke, wherein the pledget is configured to release with the first leg and the second leg upon completion of the firing stroke.

I. The staple cartridge of clause H, wherein the pledget includes a first aperture disposed at a first end of the pledget and configured to receive the first leg, and a second aperture disposed at a second end of the pledget and configured to receive the second staple leg.

J. The staple cartridge of clause I, wherein the first leg includes a first end configured to pass through the first aperture and a second end opposite the first end, the second end including a first feature to prevent the second end from passing through the first aperture during the firing stroke, and wherein the second leg includes a first end configured to pass through the second aperture and a second end opposite the first end, the second end including a second feature to prevent the second end from passing through the second aperture during the firing stroke.

K. The staple cartridge of clause J, wherein the first feature and the second feature includes an out of plane bend of the second end of the first and second staple leg portions.

L. The staple cartridge of clause K, wherein the out of plane bend of the second end of the first leg is in a first direction, and wherein the out of plane bend of the second end of the second leg is in a second direction opposite the first direction.

M. The staple cartridge of clause J, wherein the first feature and the second feature includes an end cap having a diameter larger than a diameter of the first and second apertures.

N. The staple cartridge of clause I, wherein respective first ends of respective first and second legs are configured to pass through the first and second apertures, respectively, during the firing stroke, and wherein respective second ends opposite respective first ends of respective first and second legs are configured to engage a bottom surface of the pledget upon completion of the firing stroke, such that the pledget is driven out of the staple pocket with the first and second legs.

O. A staple cartridge comprising:

a staple pocket having an opening;

a multi-part staple including a first leg, a second leg, and a pledget, wherein the pledget includes:

a first aperture disposed at a first end of the pledget and configured to receive the first leg; and a second aperture disposed at a second end of the pledget and configured to receive the second staple leg, wherein the first aperture is configured to curl the first leg as the first leg passes through the first aperture during a firing stroke, wherein the second aperture is configured to curl the second leg as the second leg passes through the second aperture during the firing stroke, and wherein the pledget is configured to release with the first leg and the second leg upon completion of the firing stroke.

P. The staple cartridge of clause O, wherein the first aperture comprises a first curved passageway, such that the first leg plastically deforms in a first direction as the first leg passes through the first curved passageway, wherein the second aperture comprises a second curved passageway, such that the second leg plastically deforms in a second direction as the second leg passes through the second curved passageway.

Q . The staple cartridge of clause P, wherein the first direction and the second direction are opposite each other.

R. The staple cartridge of clause O, wherein the first leg includes a first end configured to pass through the first aperture and a second end opposite the first end, the second end including a first feature to prevent the second end from passing through the first aperture during the firing stroke, and wherein the second leg includes a first end configured to pass through the second aperture and a second end opposite the first end, the second end including a second feature to prevent the second end from passing through the second aperture during the firing stroke.

S. The staple cartridge of clause R, wherein the first feature and second feature are each configured to engage a bottom surface of the pledget upon completion of the firing stroke, such that the pledget is driven out of the staple pocket with the first and second legs.

T. The staple cartridge of clause O, further comprising a set of arbors disposed adjacent the opening of the staple pocket, wherein the set of arbors are configured to deform the first leg and the second leg as first leg and the second leg exit the staple pocket at the opening.

XI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Patent Application Ser. No. 63/467,622, entitled “Surgical Stapler Cartridge Having Intermediate Raised Tissue Engagement Protrusions,” filed on May 19, 2023; U.S. Patent Application Ser. No. 63/467,623, entitled “Surgical Stapler Cartridge Having Tissue Engagement Protrusions with Enlarged Engagement Surface,” filed on May 19, 2023; U.S. Patent Application Ser. No. 63/467,648, entitled “Surgical Stapler Cartridge Having Raised Surface to Promote Buttress Adhesion,” filed on May 19, 2023; U.S. Patent Application Ser. No. 63/467,469, entitled “Surgical Stapler Cartridge Having Cartridge Retention Features,” filed on May 19, 2023; U.S. Patent Application Ser. No. 63/459,739, entitled “Surgical Stapler Anvil Having Staple Forming Pockets with Laterally Varying Orientations,” filed on May 19, 2023; U.S. Patent Application Ser. No. 63/467,656, entitled “Surgical Stapler With Discretely Positionable Distal Tip,” filed on May 19, 2023; and/or U.S. Patent Application Ser. No. 63/467,615, entitled “Incompatible Staple Cartridge Use Prevention Features for Surgical Stapler,” filed on May 19, 2023.

Additionally, any one or more of the teachings herein may be combined with any one or more of the teachings disclosed in U.S. Patent Application Ser. No. 63/459,739, entitled “Surgical Stapler Anvil Having Staple Forming Pockets with Laterally Varying Orientations,” filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled “Surgical Stapler with Deflectable Distal Tip,” issued Apr. 19, 2022, the disclosure of which is incorporated by reference herein, in its entirety; U.S. Pat. No. 11,317,912, entitled “Surgical Stapler with Rotatable Distal Tip,” issued May 3, 2022, the disclosure of which is incorporated by reference herein, in its entirety; and/or U.S. Pat. No. 11,439,391, entitled “Surgical Stapler with Toggling Distal Tip,” issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of forming staples between opposing jaws of a stapling device, the method comprising:

positioning a set of guide surfaces over each of a plurality of staples loaded in openings of a staple cartridge of a first jaw of the opposing jaws of the stapling device, wherein each staple comprises a crown with staple legs extending therefrom, wherein ends of the staple legs opposite the crown exit through the openings; and bending the ends of the staple legs with the guide surfaces;

wherein the guide surfaces are further configured to cause the staple legs to continue bending as the staples exit the openings.

2. The method of claim 1, wherein the plurality of staples are loaded in the openings of the first jaw such that the ends of the staple legs extend out of the openings, and wherein bending the ends of the staple legs comprises bending, by the guide surfaces, the ends of the staple legs that extend out of the openings as the guide surfaces are positioned over the staples.

3. The method of claim 2, wherein when positioning the set of guide surfaces over each of the plurality of staples, the plurality of staples are supported at the crown of the staple.

4. The method of claim 1, further comprising attaching the guide surfaces to the first jaw adjacent to the openings.

5. The method of claim 1, further comprising firing the stapling device with a firing force after bending the ends of the staple legs with the guide surfaces, wherein firing the stapling device causes the staples to exit the openings.

6. The method of claim 5, wherein firing the stapling device causes the staple legs to continue bending by forcing the staple legs past the guide surfaces using the firing force.

7. The method of claim 1, wherein the staples are retained, by the guide surfaces, in the openings of the first jaw prior to firing the stapling device.

8. The method of claim 1, wherein to cause the staple legs to continue bending, the guide surfaces are configured to curl the staple legs using the guide surfaces of the first jaw only.

9. The method of claim 1, wherein to cause the staple legs to continue bending, the guide surfaces are configured to curl the staple legs without buckling the staple legs.

10. The method of claim 1, wherein to cause the staple legs to continue bending, the guide surfaces are configured to curl the staple legs while avoiding contact with a second jaw of the opposing jaws.

11. A staple cartridge, comprising:

a cartridge body including a staple cavity having a staple aperture in a top surface of the cartridge body, the staple cavity being configured to receive a surgical staple such that the staple is vertically movable within the staple cavity along a longitudinal axis of the staple cavity; and a staple forming plate configured to be attached to the top surface of the cartridge body, wherein the staple forming plate includes a tissue contacting top surface and a bottom surface opposite the tissue contacting top surface, the staple forming plate including a staple forming channel defined in, and extending through, the staple forming plate between the tissue contacting top surface and the bottom surface, wherein when the staple forming plate is attached to the top surface of the cartridge body, the staple forming channel is aligned with the staple aperture of the staple cavity.

12. The staple cartridge of claim 11, wherein the staple includes a first staple leg and a second staple leg, wherein the staple cavity is further configured to receive the staple such that a portion of the first staple leg and a portion of the second staple leg extend out of the staple aperture in the top surface of the cartridge body.

13. The staple cartridge of claim 12, wherein the staple forming channel comprises:

a first staple forming region configured to receive the portion of the first staple leg extending out of the staple aperture, wherein the first staple forming region includes a first curved surface disposed adjacent the tissue contacting top surface of the staple forming plate; and a second staple forming region configured to receive the portion of the second staple leg extending out of the staple aperture, wherein the second staple forming region includes a second curved surface disposed adjacent the tissue contacting top surface of the staple forming plate, wherein the first curved surface and the second curved surface are configured to bend a tip of the portion of the first staple leg and a tip of the portion of the second staple leg, respectively, laterally relative to the longitudinal axis of the staple cavity when the staple forming plate is attached to the top surface of the cartridge body.

14. The staple cartridge of claim 13, wherein the first staple forming region further includes a first arbor offset laterally from the first curved surface towards a center of the staple forming channel, such that the portion of the first staple leg is disposed between the first arbor and the first curved surface, and the second staple forming region further includes a second arbor offset laterally from the second curved surface towards the center of the staple forming channel, such that the portion of the second staple leg is disposed between the second arbor and the second curved surface.

15. The staple cartridge of claim 14, wherein when the staple is advanced out of the staple cavity and through the staple forming channel of the staple forming plate, the first staple leg and second staple leg are curled toward each other based on the first staple leg and second staple leg contacting the first curved surface and second curved surface, respectively.

16. The staple cartridge of claim 13, wherein the staple cartridge is configured to be used with a surgical stapler, and wherein the first curved surface and the second curved surface are configured to retain the staple in the staple cavity prior to firing the surgical stapler.

17. A circular surgical stapling system, comprising:

a staple cartridge comprising at least one annular row of staple cavities configured to hold staples having staple legs;

an anvil configured to be positioned opposite the staple cartridge; and an annular arbor plate configured to be coupled to the staple cartridge, wherein the annular arbor plate includes a plurality of annular channels corresponding to the staple cavities, and wherein each annular channel of the plurality of annular channels includes a feature that curls the staple legs upon a firing of the staples.

18. The circular surgical stapling system of claim 17, wherein the feature comprises a curved sidewall, an arbor, or a combination thereof.

19. The circular surgical stapling system of claim 17, wherein the feature is configured to bend a portion of the staple legs when the annular arbor plate is coupled to the staple cartridge.

20. The circular surgical stapling system of claim 17, wherein the feature curls the staple legs upon the firing of the staples without buckling the staple legs against the anvil.

* * * * *